US012773443B2

(12) United States Patent
Gan et al.

(10) Patent No.: US 12,773,443 B2
(45) Date of Patent: Oct. 27, 2026

(54) INSULIN DERIVATIVE

(71) Applicant: Gan & Lee Pharmaceuticals Co., Ltd., Beijing (CN)

(72) Inventors: Zhongru Gan, Beijing (CN); Wei Chen, Beijing (CN); Yining Zhang, Beijing (CN); Fangkai Xue, Beijing (CN); Lingyu Cai, Beijing (CN); Jianghong Niu, Beijing (CN); Bin Mu, Beijing (CN)

(73) Assignee: Gan & Lee Pharmaceuticals Co., Ltd., Beijing (CN)

( * ) Notice: Subject to any disclaimer, the term of this patent is extended or adjusted under 35 U.S.C. 154(b) by 1096 days.

(21) Appl. No.: 17/758,108

(22) PCT Filed: Dec. 29, 2020

(86) PCT No.: PCT/CN2020/141056

§ 371 (c)(1),
(2) Date: Jun. 28, 2022

(87) PCT Pub. No.: WO2021/136302

PCT Pub. Date: Jul. 8, 2021

(65) Prior Publication Data

US 2024/0025957 A1 Jan. 25, 2024

(30) Foreign Application Priority Data

Dec. 30, 2019 (CN) ......................... 201911398378.0
Sep. 29, 2020 (CN) ......................... 202011057926.6

(51) Int. Cl.
*A61K 38/28* (2006.01)
*A61K 47/02* (2006.01)
(Continued)

(52) U.S. Cl.
CPC .............. *A61K 38/28* (2013.01); *A61K 47/02* (2013.01); *A61K 47/10* (2013.01); *A61P 3/10* (2018.01); *C07K 14/62* (2013.01)

(58) Field of Classification Search
CPC ........ A61K 38/28; A61K 47/02; A61K 47/10; A61K 38/00; A61P 3/10; A61P 3/00; C07K 14/62
See application file for complete search history.

(56) References Cited

U.S. PATENT DOCUMENTS 8,722,620 B2 * 5/2014 Fynbo .................... C07K 14/62 514/6.9
8,933,021 B2 * 1/2015 Hubalek ................ C07K 14/62 514/5.9
(Continued)

FOREIGN PATENT DOCUMENTS

CN 101784563 A 7/2010
CN 101842386 A 9/2010
(Continued)

OTHER PUBLICATIONS

Kurtzhals, Peter et al. "Albumin binding of insulins acylated with fatty acids: characterization of the ligand-protein interaction and correlation between binding affinity and timing of the insulin effect in vivo," Biochemical Journal, vol. 312, issue 3 (Dec. 1995) pp. 725-731.
(Continued)

*Primary Examiner* — Randall L Beane
(74) *Attorney, Agent, or Firm* — Ice Miller LLP

(57) ABSTRACT

The present invention relates to a novel insulin derivative, a pharmaceutical formulation thereof, a pharmaceutical composition thereof with a long-acting GLP-1 compound and medical use of the insulin derivative, the pharmaceutical formulation and the pharmaceutical composition. The novel acylated insulin has surprisingly and significantly increased
(Continued)

Combined male and female mice n = 9 drug effect, longer duration of action, longer in vivo half-life, good bioavailability and more satisfactory physical stability and chemical stability compared with insulin degludec or other insulin derivatives.

9 Claims, 26 Drawing Sheets

Specification includes a Sequence Listing.

(51) Int. Cl.

| | |
|---|---|
| ***A61K 47/10*** | (2017.01) |
| ***A61P 3/10*** | (2006.01) |
| ***C07K 14/62*** | (2006.01) |

(56) References Cited

U.S. PATENT DOCUMENTS

| | | | | |
|---|---|---|---|---|
| 9,481,721 | B2 | 11/2016 | Naver et al. | |
| 10,675,352 | B2 | 6/2020 | Prudent | |
| 2010/0292133 | A1 | 11/2010 | Spetzler et al. | |
| 2011/0098439 | A1* | 4/2011 | Madsen | C07K 14/62 530/303 |
| 2011/0098440 | A1 | 4/2011 | Madsen et al. | |
| 2011/0105720 | A1* | 5/2011 | Madsen | A61P 5/48 530/303 |
| 2014/0228285 | A1* | 8/2014 | Hoeg-Jensen | A61P 9/00 530/303 |
| 2015/0111820 | A1 | 4/2015 | Pridal et al. | |
| 2015/0148521 | A1 | 5/2015 | Madsen et al. | |
| 2015/0210748 | A1* | 7/2015 | Madsen | A61P 43/00 530/303 |
| 2017/0008945 | A1* | 1/2017 | Madsen | A61P 9/12 |
| 2018/0000742 | A1* | 1/2018 | Hovgaard | A61K 9/5026 |
| 2018/0169190 | A1 | 6/2018 | Norrman et al. | |
| 2018/0305431 | A1* | 10/2018 | Madsen | A61P 3/10 |
| 2019/0169257 | A1 | 6/2019 | Liu et al. | |
| 2019/0345215 | A1 | 11/2019 | Liu et al. | |
| 2023/0126068 | A1* | 4/2023 | Gan | A61K 47/02 514/5.9 |
| 2024/0025957 | A1* | 1/2024 | Gan | C07K 14/62 |
| 2024/0239859 | A1* | 7/2024 | Gan | A61K 38/26 |
| 2024/0239862 | A1* | 7/2024 | Gan | C07K 14/62 |
| 2025/0011385 | A1* | 1/2025 | Gan | A61K 9/08 |
| 2025/0032589 | A1* | 1/2025 | Gan | A61P 3/10 |
| 2025/0228919 | A1* | 7/2025 | Gan | C07K 14/62 |
| 2025/0340610 | A1* | 11/2025 | Gan | C07K 14/62 |

FOREIGN PATENT DOCUMENTS

| | | | | |
|---|---|---|---|---|
| CN | 102037008 A | | 4/2011 | |
| IN | 101784562 A | | 7/2010 | |
| WO | 2011/117416 | | 9/2011 | |
| WO | 2012171994 A1 | | 12/2012 | |
| WO | 2016/119854 | | 8/2016 | |
| WO | WO-2017032798 A1 | * | 3/2017 | A61P 3/10 |
| WO | 2018024186 A1 | | 2/2018 | |

OTHER PUBLICATIONS

International Search Report (Form PCT/ISA/210) for International Patent Application No. PCT/CN2020/141056, issued from the International Searching Authority, date of mailing Mar. 26, 2021, 16 pages.
Written Opinion of the International Searching Authority (Form PCT/ISA/237) for International Patent Application No. PCT/CN2020/141056, issued from the International Searching Authority, date of mailing Mar. 30, 2021, 16 pages.
International Preliminary Report on Patentability (Form PCT/IB/373) for International Patent Application No. PCT/CN2020/141056, issued from the International Searching Authority, date of mailing Jul. 5, 2022, 8 pages.
U.S. Appl. No. 17/758,089, entitled "Insulin Derivative," filed Jun. 28, 2022, 118 pages.
U.S. Appl. No. 17/758,101, entitled "Insulin Derivative," filed Jun. 28, 2022, 130 pages.
U.S. Appl. No. 17/758,113, entitled "Long-Acting GLP-1 Compound," filed Jun. 28, 2022, 90 pages.
Escribano O. et al. "The Role of Insulin Receptor Isoforms in Diabetes and Its Metabolic and Vascular Complications," Journal of Diabetes Research, vol. 2017, article ID: 1403206 (2017) pp. 1-12.
Acta Biochimica et Biophysica Sinica, vol. 15, Issue 6 (Dec. 31, 1983).

* cited by examiner

SEQUENCE LISTING

<160> NUMBER OF SEQ ID NOS: 17

<210> SEQ ID NO 1
<211> LENGTH: 21
<212> TYPE: PRT
<213> ORGANISM: Artificial Sequence
<220> FEATURE:
<223> OTHER INFORMATION: A chain of desB30 human insulin

<400> SEQUENCE: 1

Gly Ile Val Glu Gln Cys Cys Thr Ser Ile Cys Ser Leu Tyr Gln Leu
1 5 10 15

Glu Asn Tyr Cys Asn
20

<210> SEQ ID NO 2
<211> LENGTH: 29
<212> TYPE: PRT
<213> ORGANISM: Artificial Sequence
<220> FEATURE:
<223> OTHER INFORMATION: B chain of desB30 human insulin

<400> SEQUENCE: 2

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys
20 25

<210> SEQ ID NO 3
<211> LENGTH: 21
<212> TYPE: PRT
<213> ORGANISM: Artificial Sequence
<220> FEATURE:
<223> OTHER INFORMATION: A chain of A14E, B16H, B25H, desB30 human
insulin

<400> SEQUENCE: 3

Gly Ile Val Glu Gln Cys Cys Thr Ser Ile Cys Ser Leu Glu Gln Leu
1 5 10 15

Glu Asn Tyr Cys Asn
20

<210> SEQ ID NO 4
<211> LENGTH: 29
<212> TYPE: PRT
<213> ORGANISM: Artificial Sequence
<220> FEATURE:
<223> OTHER INFORMATION: B chain of A14E, B16H, B25H, desB30 human
insulin

<400> SEQUENCE: 4

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys

-continued

```
            20                  25


<210> SEQ ID NO 5
<211> LENGTH: 21
<212> TYPE: PRT
<213> ORGANISM: Artificial Sequence
<220> FEATURE:
<223> OTHER INFORMATION: A chain of A14E, B16E, B25H, desB30 human
      insulin

<400> SEQUENCE: 5

Gly Ile Val Glu Gln Cys Cys Thr Ser Ile Cys Ser Leu Glu Gln Leu
1               5                   10                  15

Glu Asn Tyr Cys Asn
            20


<210> SEQ ID NO 6
<211> LENGTH: 29
<212> TYPE: PRT
<213> ORGANISM: Artificial Sequence
<220> FEATURE:
<223> OTHER INFORMATION: B chain of A14E, B16E, B25H, desB30 human
      insulin

<400> SEQUENCE: 6

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys
            20                  25


<210> SEQ ID NO 7
<211> LENGTH: 21
<212> TYPE: PRT
<213> ORGANISM: Artificial Sequence
<220> FEATURE:
<223> OTHER INFORMATION: A chain of human insulin

<400> SEQUENCE: 7

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 8
<211> LENGTH: 30
<212> TYPE: PRT
<213> ORGANISM: Artificial Sequence
<220> FEATURE:
<223> OTHER INFORMATION: B chain of human insulin

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 9
<211> LENGTH: 21
<212> TYPE: PRT
<213> ORGANISM: Artificial Sequence
<220> FEATURE:
<223> OTHER INFORMATION: A chain of A21G human insulin

<400> SEQUENCE: 9

Gly Ile Val Glu Gln Cys Cys Thr Ser Ile Cys Ser Leu Tyr Gln Leu
```

-continued

```
1               5                   10                  15

Glu Asn Tyr Cys Gly
            20


<210> SEQ ID NO 10
<211> LENGTH: 30
<212> TYPE: PRT
<213> ORGANISM: Artificial Sequence
<220> FEATURE:
<223> OTHER INFORMATION: B chain of A21G human insulin

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 11
<211> LENGTH: 21
<212> TYPE: PRT
<213> ORGANISM: Artificial Sequence
<220> FEATURE:
<223> OTHER INFORMATION: A chain of A21G, desB30 human insulin

<400> SEQUENCE: 11

Gly Ile Val Glu Gln Cys Cys Thr Ser Ile Cys Ser Leu Tyr Gln Leu
1               5                   10                  15

Glu Asn Tyr Cys Gly
            20


<210> SEQ ID NO 12
<211> LENGTH: 29
<212> TYPE: PRT
<213> ORGANISM: Artificial Sequence
<220> FEATURE:
<223> OTHER INFORMATION: B chain of A21G, desB30 human insulin

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25


<210> SEQ ID NO 13
<211> LENGTH: 21
<212> TYPE: PRT
<213> ORGANISM: Artificial Sequence
<220> FEATURE:
<223> OTHER INFORMATION: A chain of B28D human insulin

<400> SEQUENCE: 13

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 14
<211> LENGTH: 30
<212> TYPE: PRT
<213> ORGANISM: Artificial Sequence
<220> FEATURE:
<223> OTHER INFORMATION: B chain of B28D human insulin

<400> SEQUENCE: 14
```

-continued

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30


<210> SEQ ID NO 15
<211> LENGTH: 31
<212> TYPE: PRT
<213> ORGANISM: Artificial Sequence
<220> FEATURE:
<223> OTHER INFORMATION: GLP-1-(7-37) peptide

<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 16
<211> LENGTH: 31
<212> TYPE: PRT
<213> ORGANISM: Artificial Sequence
<220> FEATURE:
<223> OTHER INFORMATION: [Gly8, Arg34]GLP-1-(7-37) peptide

<400> SEQUENCE: 16

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 17
<211> LENGTH: 31
<212> TYPE: PRT
<213> ORGANISM: Artificial Sequence
<220> FEATURE:
<223> OTHER INFORMATION: [Arg34]GLP-1-(7-37) peptide

<400> SEQUENCE: 17

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

INSULIN DERIVATIVE

CROSS-REFERENCE TO RELATED APPLICATIONS

This application is a Section 371 of International Application No. PCT/CN2020/141056, filed on Dec. 29, 2020, which published in the Chinese language on Jul. 8, 2021, under International Publication No. WO 2021/136302 A1 that claims priority to Chinese Patent Application No. CN 201911398378.0 filed on Dec. 30, 2019, and to Chinese Patent Application No. CN 202011057926.6 filed on Sep. 29, 2020. Each disclosure is incorporated herein by reference in its entirety.

REFERENCE TO SEQUENCE LISTING SUBMITTED ELECTRONICALLY

This application contains a sequence listing that is submitted electronically via EFS-Web as an ASCII formatted sequence listing with a file name "063038_6US1 Substitute Sequence Listing" and a creation date of Aug. 29, 2022, and having a size of 6.1 kb. The sequence listing, submitted via EFS-Web, is part of the specification and is herein incorporated by reference in its entirety.

TECHNICAL FIELD

The present invention relates to the field of therapeutic peptides, and in particular to a novel insulin derivative and a pharmaceutical formulation thereof, a pharmaceutical composition thereof with a long-acting GLP-1 compound and a pharmaceutical composition thereof with a rapid-acting insulin, and medical use of the insulin derivative, the pharmaceutical formulation and the pharmaceutical compositions.

BACKGROUND

Insulin is a polypeptide hormone secreted by R cells of the pancreas. Insulin consists of 2 polypeptide chains named as A chain and B chain, which are linked together by 2 inter-chain disulfide bonds. In human, porcine and bovine insulin, the A chain and the B chain contain 21 and 30 amino acid residues, respectively. However, from species to species, there are variations among the amino acid residues present in different positions in the 2 chains. The widespread use of genetic engineering has made it possible to prepare analogues of natural insulins by substitution, deletion and addition of one or more amino acid residues.

Insulin can be used to treat diabetes and diseases associated with or resulting from it, and it is essential in maintaining normal metabolic regulation. However, natural insulins such as human insulin have a relatively short duration of action, which necessitates frequent injections by the patient and causes a lot of injection-related discomfort in the patient. Therefore, there is continuing effort to obtain insulin derivatives or analogues that feature improved drug effect, longer duration of action, and lower frequency of injection to ameliorate the inconvenience and discomfort associated with high frequency of insulin injection.

WO1995007931A1 has disclosed insulin detemir, a commercially available long-acting insulin, which has a molecular structural feature that threonine at position 30 of the B chain of human insulin is deleted and a 14-carbon fatty monoacid is connected to lysine residue at position 29 of the B chain. WO2005012347A2 has disclosed insulin degludec, another long-acting insulin, which is a novel super long-acting insulin with longer duration of action than insulin detemir and has a molecular structural feature that threonine at position 30 of the B chain of human insulin is deleted and a 16-carbon fatty diacid side chain is connected to lysine residue at position B29 via 1 glutamic acid molecule. CN101573133B and WO2009/010428 disclose PEGylated extended insulin, which has a longer duration of action compared to a conventional unmodified insulin. WO2013086927A1 and WO2018/024186 have disclosed a long-acting acylated derivative of human insulin analogue. However, to date, no basal insulin product whose subcutaneous injection frequency is less than once daily has been approved for sale.

Thus, there is still a need for insulin derivatives or analogues with better drug effect or efficacy, longer duration of action, lower frequency of administration and superior physicochemical properties compared to the insulin already on the market (e.g., insulin degludec) or the known insulin derivatives.

SUMMARY

The present invention provides a novel insulin derivative (e.g., an acylated insulin). The inventors have surprisingly found, through extensive experiments, that the novel insulin derivative (e.g., the acylated insulin) has surprisingly and significantly increased potency, efficacy or drug effect, longer duration of action, longer in vivo half-life, good bioavailability, better safety, and more satisfactory physical stability, chemical stability and solubility compared with the commercially available insulin degludec (trade name "Tresiba") or some other insulin derivatives.

In one aspect, the present invention provides an insulin derivative comprising an insulin parent, an albumin binding residue and a linker Lin, wherein the insulin parent is a natural insulin or insulin analogue, and the albumin binding residue is linked to the insulin parent via the linker Lin, wherein,

- the linker Lin is a hydrophilic linker containing at least 10, preferably at least 15, preferably at least 20, preferably at least 25, preferably at least 30, preferably at least 36, preferably at least 40, preferably 15-200, preferably 20-200, preferably 25-180, preferably 30-180, preferably 42-180, preferably 54-180, preferably 59-180, preferably 61-180, preferably 66-180, or preferably 72-120 carbon atoms; or the linker Lin comprises at least 5 neutral and alkylene glycol-containing amino acid residues; preferably, the linker Lin comprises at least 6 neutral and alkylene glycol-containing amino acid residues; preferably, the linker Lin comprises 5-20 neutral and alkylene glycol-containing amino acid residues; or, the linker Lin comprises alkylene glycol containing at least 15, preferably at least 20, preferably at least 24, preferably at least 30, preferably at least 42, preferably 15-120, preferably 20-120, preferably 30-100, preferably 39-100 or preferably 42-80 carbon atoms; and
- the albumin binding residue contains 20-40 carbon atoms; preferably, the albumin binding residue comprises a linear or branched lipophilic a group containing 20-40 carbon atoms; preferably, the albumin binding residue is a fatty acid or a fatty diacid containing 20-26 carbon atoms (more preferably a fatty acid or a fatty diacid containing 20-24 carbon atoms), wherein formally, a hydroxyl group has been removed from the carboxyl group in the fatty acid and one of the carboxyl groups in the fatty diacid; and the insulin parent is not A14E, B16H, B25H, desB30 human insulin when the linker Lin is a hydrophilic linker containing 60 carbon atoms and the albumin binding residue is a fatty diacid containing 20 carbon atoms.

The inventors have surprisingly found, through extensive experiments, that a combination of a certain length of the albumin binding residue and a certain length of the hydrophilic linker in the insulin derivative of the present invention allows the insulin derivatives of the present invention to, as compared to existing insulin derivatives, have an equivalent or longer duration of action and meanwhile, have a surprisingly and significantly increased drug effect and a significantly increased binding capability for an insulin receptor as influence of albumin on the binding capability for the insulin receptor is remarkably reduced when the albumin is present.

In some embodiments, the insulin parent comprises at least one lysine residue, and the albumin binding residue is linked to an amino group of the lysine residue or an N-terminal amino acid residue of the insulin parent via the linker Lin.

In some embodiments, the insulin derivative further comprises one or more linkers II, wherein the linker II is an acidic amino acid residue, and the linker II is linked between the albumin binding residue and the linker Lin and/or between the linker Lin and the insulin parent, and is preferably linked between the albumin binding residue and the linker Lin.

In another aspect, the present invention provides an insulin derivative, which is an acylated insulin, wherein the insulin parent of the acylated insulin is a natural insulin or an insulin analogue and comprises at least one lysine residue, and the acyl moiety of the acylated insulin is linked to an amino group of the lysine residue or an N-terminal amino acid residue of the insulin parent, wherein the acyl moiety is shown as formula (A):

$$III\text{-}(II)_m\text{-}(I)_n\text{-} \quad (A),$$

wherein, m is 0, 1, 2, 3, 4, 5, 6, 7, 8, 9 or 10, and n is an integer equal to or greater than 5, preferably an integer from 5 to 30;

I is a neutral and alkylene glycol-containing amino acid residue;

II is an acidic amino acid residue;

III is a fatty acid or a fatty diacid containing 20-26 (preferably 20-24) carbon atoms, wherein formally, a hydroxyl group has been removed from the carboxyl group in the fatty acid and one of the carboxyl groups in the fatty diacid;

III, II and I are linked by amide bonds;

the order of II and I presented in the formula (A) can be interchanged independently; and the insulin parent is not A14E, B16H, B25H, desB30 human insulin when m is 1, n is 10, and III is a fatty diacid containing 20 carbon atoms;

or the acyl moiety is shown as formula (A'):

$$III\text{-}(II)_m\text{-}(I')_{n'}\text{-} \quad (A'),$$

wherein, m is 0, 1, 2, 3, 4, 5, 6, 7, 8, 9 or 10, and n' is an integer;

I' is a neutral and alkylene glycol-containing amino acid residue;

II is an acidic amino acid residue;

III is a fatty acid or a fatty diacid containing 20-26 (preferably 20-24) carbon atoms, wherein formally, a hydroxyl group has been removed from the carboxyl group in the fatty acid and one of the carboxyl groups in the fatty diacid;

III, II and I' are linked by amide bonds;

the order of II and I' presented in the formula (A') can be interchanged independently; and the total number of carbon atoms in $(I')_n$ is 15-200, preferably 20-200, preferably 25-180, preferably 30-180, preferably 42-180, preferably 54-180, preferably 59-180, preferably 61-180, preferably 66-180 or preferably 72-120; and the insulin parent is not A14E, B16H, B25H, desB30 human insulin when m is 1, the total number of carbon atoms in $(I')_n$ is 60, and III is a fatty diacid containing 20 carbon atoms.

In another aspect, the present invention provides an insulin derivative, which is an acylated insulin, wherein the insulin parent of the acylated insulin is a natural insulin or an insulin analogue and comprises at least one lysine residue, and the acyl moiety of the acylated insulin is linked to an amino group of the lysine residue or an N-terminal amino acid residue of the insulin parent, wherein the acyl moiety is shown as formula (A):

$$III\text{-}(II)_m\text{-}(I)_n\text{-} \quad (A),$$

wherein, m is 0, 1, 2, 3, 4, 5, 6, 7, 8, 9 or 10, and n is 5, 6, 7, 8, 9, 10, 11, 12, 13, 14, 15, 16, 17, 18, 19 or 20;

I is a neutral and alkylene glycol-containing amino acid residue;

II is an acidic amino acid residue;

III is a fatty diacid containing 20-26 (preferably 20-24) carbon atoms, wherein formally, a hydroxyl group has been removed from one of the carboxyl groups in the fatty diacid;

III, II and I are linked by amide bonds;

the order of II and I presented in the formula (A) can be interchanged independently; and the insulin parent is not A14E, B16H, B25H, desB30 human insulin when m is 1, n is 10, and III is a fatty diacid containing 20 carbon atoms;

or the acyl moiety is shown as formula (A'):

$$III\text{-}(II)_m\text{-}(I')_{n'}\text{-} \quad (A'),$$

wherein, m is 0, 1, 2, 3, 4, 5, 6, 7, 8, 9 or 10, and n' is an integer;

I' is a neutral and alkylene glycol-containing amino acid residue;

II is an acidic amino acid residue;

III is a fatty diacid containing 20-26 (preferably 20-24) carbon atoms, wherein formally, a hydroxyl group has been removed from one of the carboxyl groups in the fatty diacid;

III, II and I' are linked by amide bonds;

the order of II and I' presented in the formula (A') can be interchanged independently; and the total number of carbon atoms in $(I')_n$ is 20-200, preferably 25-180, preferably 30-180, preferably 42-180, preferably 54-180, preferably 59-180, preferably 61-180, preferably 66-180 or preferably 72-120; and the insulin parent is not A14E, B16H, B25H, desB30 human insulin when m is 1, the total number of carbon atoms in $(I')_n$ is 60, and III is a fatty diacid containing 20 carbon atoms.

In some embodiments, n is an integer from 5 to 15; preferably, n is 5, 6, 7, 8, 9, 10, 11, 12, 13 or 14; preferably, n is 5, 6, 7, 8, 9, 10, 11, or 12; preferably, n is 5, 6, 7, 8, 9 or 10; preferably, n is 5, 6, 7, 8 or 9; preferably, n is 5, 6, 7 or 8; and/or m is an integer from 1 to 6; preferably, m is 1, 2, 3 or 4; preferably, m is 1 or 2; preferably, m is 1; and/or III is a fatty diacid containing 20-26 (preferably 20-23) carbon atoms, and preferably III is a fatty diacid containing 20, 21 or 22 carbon atoms, wherein formally, a hydroxyl group has been removed from one of the carboxyl groups in the fatty diacid; and/or the insulin parent comprises one lysine residue.

In some embodiments, I is: $-HN-(CH_2)_2-O-(CH_2)_2O-CH_2-CO-$, $-HN-(CH_2)_2-O-(CH_2)_2-O-(CH_2)_2-O-(CH_2)_2-O-(CH_2)_2-CO-$, $-HN-(CH_2)_2-O-(CH_2)_2-O-(CH_2)_2-O-(CH_2)_2-O-(CH_2)_2-O-(CH_2)_2-O-(CH_2)_2-CO-$, $-HN-(CH_2)_2-O-(CH_2)_2-O-(CH_2)_2-O-(CH_2)_2-O-(CH_2)_2-O-(CH_2)_2-O-(CH_2)_2-O-(CH_2)_2-O-(CH_2)_2-CO-$, $-HN-(CH_2)_3-O-(CH_2)_4-O-(CH_2)_3-NH-CO-$, $-HN-(CH_2)_3-O-(CH_2)_4-O-(CH_2)_3-NH-CO-CH_2-O-CH_2-CO-$, $-HN-(CH_2)_3-O-(CH_2)_4-O-(CH_2)_3-NH-CO-(CH_2)_2-CO-$, $-HN-(CH_2)_2-O-(CH_2)_2O-CH_2-CO-CH_2-O-CH_2-CO-$, $-HN-(CH_2)_3-O-(CH_2)_2-O-(CH_2)_2-O-(CH_2)_3-NH-CO-(CH_2)_2-CO-$, $-HN-(CH_2)_3-O-(CH_2)_2-O-(CH_2)_2-O-(CH_2)_3-NH-CO-CH_2-O-CH_2-CO-$, $-HN-(CH_2)_2-O-(CH_2)_2-O-(CH_2)_2-NH-CO-(CH_2)_2-CO-$, $-HN-(CH_2)_2-O-(CH_2)_2-O-(CH_2)_2-NH-CO-CH_2-O-CH_2-CO-$, $-HN-(CH_2)_3-O-(CH_2)_2-O-(CH_2)_2-O-(CH_2)_3-NH-CO-CH_2-O-CH_2-CO-$, $-HN-(CH_2)_3-O-(CH_2)_3-O-CH_2-CO-$, or $-HN-(CH_2)_4-O-(CH_2)_4O-CH_2-CO-$; preferably, I is $-HN-(CH_2)_2-O-(CH_2)_2O-CH_2-CO-$; or I' is $HN-(CH_2-CH_2-O)_{10}-CH_2-CO-$, $-HN-(CH_2-CH_2-O)_{11}-CH_2-CO-$, $-HN-(CH_2-CH_2-O)_{12}-CH_2-CO-$, $-HN-(CH_2-CH_2-CH_2-O)_8-CH_2-CO-$, $-HN-(CH_2-CH_2-O)_2O-CH_2-CO-$, $-HN-(CH_2-CH_2-O)_{22}-CH_2-CO-$, $-HN-(CH_2-CH_2-O)_{24}-CH_2-CO-$, or $-HN-(CH_2-CH_2-CH_2-O)_{15}-CH_2-CO-$; and/or II is an amino acid residue selected from the group consisting of: γGlu, αGlu, βAsp, αAsp, γ-D-Glu, α-D-Glu, β-D-Asp and α-D-Asp; preferably, II is selected from γGlu and βAsp; and/or III is $HOOC-(CH_2)_{18}-CO-$, $HOOC-(CH_2)_{19}-CO-$, $HOOC-(CH_2)_{20}-CO-$, $HOOC-(CH_2)_{21}-CO-$, $HOOC-(CH_2)_{22}-CO-$, or $HOOC-(CH_2)_{24}-CO-$; preferably, III is $HOOC-(CH_2)_{18}-CO-$, $HOOC-(CH_2)_{19}-CO-$, $HOOC-(CH_2)_{20}-CO-$, $HOOC-(CH_2)_{21}-CO-$ or $HOOC-(CH_2)_{22}-CO-$; preferably, III is $HOOC-(CH_2)_{18}-CO-$, $HOOC-(CH_2)_{20}-CO-$ or $HOOC-(CH_2)_{22}-CO-$.

In some embodiments, the formula (A) is linked to the amino group of a lysine residue or the N-terminal amino acid residue of the insulin parent via the C-terminal of I, or the formula (A') is linked to the amino group of a lysine residue or the N-terminal amino acid residue of the insulin parent via the C-terminal of I'.

In some embodiments, the acyl moiety is linked to an F amino group of the lysine residue of the insulin parent.

In some embodiments, the lysine residue of the insulin parent is at position B29.

In some embodiments, the insulin parent is selected from the group consisting of: desB30 human insulin (SEQ ID NO: 1 and SEQ ID NO: 2, representing A chain and B chain, respectively); A14E, B16H, B25H, desB30 human insulin (SEQ ID NO: 3 and SEQ ID NO: 4, representing A chain and B chain, respectively); A14E, B16E, B25H, desB30 human insulin (SEQ ID NO: 5 and SEQ ID NO: 6, representing A chain and B chain, respectively); human insulin (SEQ ID NO: 7 and SEQ ID NO: 8, representing A chain and B chain, respectively); A21G human insulin (SEQ ID NO: 9 and SEQ ID NO: 10, representing A chain and B chain, respectively); A21G, desB30 human insulin (SEQ ID NO: 11 and SEQ ID NO: 12, representing A chain and B chain, respectively); and B28D human insulin (SEQ ID NO: 13 and SEQ ID NO: 14, representing A chain and B chain, respectively); preferably, the insulin parent is desB30 human insulin; A14E, B16H, B25H, desB30 human insulin; or A14E, B16E, B25H, desB30 human insulin.

In some embodiments, the acylated insulin is selected from the group consisting of B29K(N(ε)-eicosanedioyl-γGlu-5×OEG), desB30 human insulin; B29K(N(ε)-eicosanedioyl-γGlu-6×OEG), desB30 human insulin; B29K(N(ε)-eicosanedioyl-γGlu-γGlu-5×OEG), desB30 human insulin; B29K(N(ε)-eicosanedioyl-γGlu-γGlu-6×OEG), desB30 human insulin; B29K(N(ε)-eicosanedioyl-5×OEG-γGlu), desB30 human insulin; B29K(N(ε)-eicosanedioyl-6×OEG-γGlu), desB30 human insulin; B29K(N(ε)-eicosanedioyl-6×OEG-γGlu-γGlu), desB30 human insulin; B29K(N(ε)-eicosanedioyl-5×OEG-γGlu-γGlu), desB30 human insulin; B29K(N(ε)-eicosanedioyl-βAsp-5×OEG), desB30 human insulin; B29K(N(ε)-eicosanedioyl-βAsp-6×OEG), desB30 human insulin; B29K(N(ε)-eicosanedioyl-αGlu-5×OEG), desB30 human insulin; B29K(N(ε)-eicosanedioyl-αGlu-6×OEG), desB30 human insulin; B29K(N(ε)-eicosanedioyl-αGlu-αGlu-5×OEG), desB30 human insulin; B29K(N(ε)-eicosanedioyl-αGlu-αGlu-6×OEG), desB30 human insulin; B29K(N(ε)-eicosanedioyl-αAsp-5×OEG), desB30 human insulin; B29K(N(ε)-eicosanedioyl-αAsp-6×OEG), desB30 human insulin; B29K(N(ε)-eicosanedioyl-γGlu-7×OEG), desB30 human insulin; B29K(N(ε)-eicosanedioyl-γGlu-8×OEG), desB30 human insulin; B29K(N(ε)-eicosanedioyl-γGlu-γGlu-7×OEG), desB30 human insulin; B29K(N(ε)-eicosanedioyl-γGlu-γGlu-8×OEG), desB30 human insulin; B29K(N(ε)-eicosanedioyl-7×OEG-γGlu), desB30 human insulin; B29K(N(ε)-eicosanedioyl-8×OEG-γGlu), desB30 human insulin; B29K(N(ε)-eicosanedioyl-8×OEG-γGlu-γGlu), desB30 human insulin; B29K(N(ε)-eicosanedioyl-7×OEG-γGlu-γGlu), desB30 human insulin; B29K(N(ε)-eicosanedioyl-βAsp-7×OEG), desB30 human insulin; B29K(N(ε)-eicosanedioyl-βAsp-8×OEG), desB30 human insulin; B29K(N(ε)-eicosanedioyl-αGlu-7×OEG), desB30 human insulin; B29K(N(ε)-eicosanedioyl-αGlu-8×OEG), desB30 human insulin; B29K(N(ε)-eicosanedioyl-αGlu-αGlu-7×OEG), desB30 human insulin; B29K(N(ε)-eicosanedioyl-αGlu-αGlu-8×OEG), desB30 human insulin; B29K(N(ε)-eicosanedioyl-αAsp-7×OEG), desB30 human insulin; B29K(N(ε)-eicosanedioyl-αAsp-8×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-docosanedioyl-γGlu-γGlu-5×OEG), desB30 human insulin; B29K(N(ε)-docosanedioyl-γGlu-γGlu-6×OEG), desB30 human insulin; B29K(N(ε)-docosanedioyl-5×OEG- γGlu), desB30 human insulin; B29K(N(ε)-docosanedioyl-6×OEG-γGlu), desB30 human insulin; B29K(N(ε)-docosanedioyl-6×OEG-γGlu-γGlu), desB30 human insulin; B29K(N(ε)-docosanedioyl-5×OEG-γGlu-γGlu), desB30 human insulin; B29K(N(ε)-docosanedioyl-βAsp-5×OEG), desB30 human insulin; B29K(N(ε)-docosanedioyl-βAsp-6×OEG), desB30 human insulin; B29K(N(ε)-docosanedioyl-αGlu-5×OEG), desB30 human insulin; B29K(N(ε)-docosanedioyl-αGlu-6×OEG), desB30 human insulin; B29K(N(ε)-docosanedioyl-αGlu-αGlu-5×OEG), desB30 human insulin; B29K(N(ε)-docosanedioyl-αGlu-αGlu-6×OEG), desB30 human insulin; B29K(N(ε)-docosanedioyl-αAsp-5×OEG), desB30 human insulin; B29K(N(ε)-docosanedioyl-αAsp-6×OEG), desB30 human insulin; B29K(N(ε)-docosanedioyl-γGlu-7×OEG), desB30 human insulin; B29K(N(ε)-docosanedioyl-γGlu-8×OEG), desB30 human insulin; B29K(N(ε)-docosanedioyl-γGlu-γGlu-7×OEG), desB30 human insulin; B29K(N(ε)-docosanedioyl-γGlu-γGlu-8×OEG), desB30 human insulin; B29K(N(ε)-docosanedioyl-7×OEG-γGlu), desB30 human insulin; B29K(N(ε)-docosanedioyl-8×OEG-γGlu), desB30 human insulin; B29K(N(ε)-docosanedioyl-8×OEG-γGlu-γGlu), desB30 human insulin; B29K(N(ε)-docosanedioyl-7×OEG-γGlu-γGlu), desB30 human insulin; B29K(N(ε)-docosanedioyl-βAsp-7×OEG), desB30 human insulin; B29K(N(ε)-docosanedioyl-βAsp-8×OEG), desB30 human insulin; B29K(N(ε)-docosanedioyl-αGlu-7×OEG), desB30 human insulin; B29K(N(ε)-docosanedioyl-αGlu-8×OEG), desB30 human insulin; B29K(N(ε)-docosanedioyl-αGlu-αGlu-7×OEG), desB30 human insulin; B29K(N(ε)-docosanedioyl-αGlu-αGlu-8×OEG), desB30 human insulin; B29K(N(ε)-docosanedioyl-αAsp-7×OEG), desB30 human insulin; B29K(N(ε)-docosanedioyl-αAsp-8×OEG), desB30 human insulin; B29K(N(ε)-heneicosanedioyl-γGlu-5×OEG), desB30 human insulin; B29K(N(ε)-heneicosanedioyl-γGlu-6×OEG), desB30 human insulin; B29K(N(ε)-heneicosanedioyl-γGlu-7×OEG), desB30 human insulin; B29K(N(ε)-heneicosanedioyl-γGlu-8×OEG), desB30 human insulin; B29K(N(ε)-tricosanedioyl-γGlu-5×OEG), desB30 human insulin; B29K(N(ε)-tricosanedioyl-γGlu-6×OEG), desB30 human insulin; B29K(N(ε)-tricosanedioyl-γGlu-7×OEG), desB30 human insulin; B29K(N(ε)-tricosanedioyl-γGlu-8×OEG), desB30 human insulin; B29K(N(ε)-tetracosanedioyl-γGlu-5×OEG), desB30 human insulin; B29K(N(ε)-tetracosanedioyl-γGlu-6×OEG), desB30 human insulin; B29K(N(ε)-tetracosanedioyl-γGlu-7×OEG), desB30 human insulin; B29K(N(ε)-tetracosanedioyl-γGlu-8×OEG), desB30 human insulin; B29K(N(ε)-eicosanedioyl-γGlu-12×OEG), desB30 human insulin; B29K(N(ε)-docosanedioyl-γGlu-12×OEG), desB30 human insulin; B29K(N(ε)-eicosanedioyl-γGlu-9×OEG), desB30 human insulin; B29K(N(ε)-eicosanedioyl-γGlu-10×OEG), desB30 human insulin; B29K(N(ε)-eicosanedioyl-γGlu-11×OEG), desB30 human insulin; B29K(N(ε)-docosanedioyl-γGlu-9×OEG), desB30 human insulin; B29K(N(ε)-docosanedioyl-γGlu-10×OEG), desB30 human insulin; B29K(N(ε)-docosanedioyl-γGlu-11×OEG), desB30 human insulin; B29K(N(ε)-heneicosanedioyl-γGlu-12×OEG), desB30 human insulin; B29K(N(ε)-tricosanedioyl-γGlu-12×OEG), desB30 human insulin; B29K(N(ε)-tetracosanedioyl-γGlu-12×OEG), desB30 human insulin; B29K(N(ε)-docosanedioyl-γGlu-12×PEG), desB30 human insulin; B29K(N(ε)-eicosanedioyl-γGlu-12×PEG), desB30 human insulin; B29K(N(ε)-docosanedioyl-γGlu-13×PEG), desB30 human insulin; B29K(N(ε)-eicosanedioyl-γGlu-13×PEG), desB30 human insulin; B29K(N(ε)-docosanedioyl-γGlu-14×PEG), desB30 human insulin; B29K(N(ε)-eicosanedioyl-γGlu-14×PEG), desB30 human insulin; B29K(N(ε)-docosanedioyl-γGlu-15×PEG), desB30 human insulin; B29K(N(ε)-eicosanedioyl-γGlu-15×PEG), desB30 human insulin; B29K(N(ε)-docosanedioyl-γGlu-16×PEG), desB30 human insulin; B29K(N(ε)-eicosanedioyl-γGlu-16×PEG), desB30 human insulin; B29K(N(ε)-docosanedioyl-γGlu-17×PEG), desB30 human insulin; B29K(N(ε)-eicosanedioyl-γGlu-17×PEG), desB30 human insulin; B29K(N(ε)-docosanedioyl-γGlu-18×PEG), desB30 human insulin; and B29K(N(ε)-eicosanedioyl-γGlu-18×PEG), desB30 human insulin;

preferably, the acylated insulin is selected from the group consisting of B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-7×OEG), desB30 human insulin; B29K(N(ε)-eicosanedioyl-γGlu-8×OEG), desB30 human insulin; B29K(N(ε)-docosanedioyl-γGlu-7×OEG), desB30 human insulin; B29K(N(ε)-docosanedioyl-γGlu-8×OEG), desB30 human insulin; B29K(N(ε)-eicosanedioyl-γGlu-9×OEG), desB30 human insulin; B29K(N(ε)-eicosanedioyl-γGlu-10×OEG), desB30 human insulin; B29K(N(ε)-docosanedioyl-γGlu-9×OEG), desB30 human insulin; B29K(N(ε)-docosanedioyl-γGlu-10×OEG), desB30 human insulin; B29K(N(ε)-eicosanedioyl-γGlu-11×OEG), desB30 human insulin; B29K(N(ε)-eicosanedioyl-γGlu-12×OEG), desB30 human insulin; B29K(N(ε)-docosanedioyl-γGlu-11×OEG), desB30 human insulin; and B29K(N(ε)-docosanedioyl-γGlu-12×OEG), desB30 human insulin;

more preferably, the acylated insulin is selected from the group consisting of B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-8×OEG), desB30 human insulin; and B29K(N(ε)-docosanedioyl-γGlu-8×OEG), desB30 human insulin.

In another aspect, the present invention provides an insulin derivative, which is an acylated insulin, wherein the insulin parent of the acylated insulin is A14E, B16H, B25H, desB30 human insulin or A14E, B16E, B25H, desB30 human insulin, and the acyl moiety of the acylated insulin is linked to an amino group of the lysine residue or an N-terminal amino acid residue of the insulin parent, wherein the acyl moiety is shown as formula (C):

$$Y1\text{-}(Y2)_{m1}\text{-}(Y3)_{n1}\text{-} \quad (C),$$

wherein, m1 is 0, 1, 2, 3, 4, 5, 6, 7, 8, 9 or 10, and n1 is an integer of 5, 6, 7, 8, 9 or 10;

Y3 is a neutral and alkylene glycol-containing amino acid residue;

Y2 is an acidic amino acid residue;

Y1 is a fatty diacid containing 20-24 carbon atoms, wherein formally, a hydroxyl group has been removed from one of the carboxyl groups in the fatty diacid;

Y1, Y2 and Y3 are linked by amide bonds;

the order of Y2 and Y3 presented in the formula (C) can be interchanged independently; and n1 is not 10 when Y1 is a fatty diacid containing 20 carbon atoms, formally a hydroxyl group has been removed from one of the carboxyl groups in the fatty diacid and m1 is 1;

or the acyl moiety is shown as formula (C'):

$$Y1\text{-}(Y2)_{m1}\text{-}(Y3')_{n1'}\text{-} \quad (C'),$$

wherein, m1 is 0, 1, 2, 3, 4, 5, 6, 7, 8, 9 or 10, and n1' is an integer of 5, 6, 7, 8, 9 or 10;

Y3' is a neutral and alkylene glycol-containing amino acid residue;

Y2 is an acidic amino acid residue;

Y1 is a fatty diacid containing 20-24 carbon atoms, wherein formally, a hydroxyl group has been removed from one of the carboxyl groups in the fatty diacid;

Y1, Y2 and Y3' are linked by amide bonds;

the order of Y2 and Y3' presented in the formula (C') can be interchanged independently; the total number of carbon atoms in $(Y3')_{n1}$, is 15-100, preferably 20-100, preferably 25-90, preferably 30-80, preferably 30-59 or preferably 30-54; and the total number of carbon atoms in $(Y3')_{n1}$, is not 60 when Y1 is a fatty diacid containing 20 carbon atoms, wherein formally a hydroxyl group has been removed from one of the carboxyl groups in the fatty diacid and m1 is 1.

In some embodiments, n1 is 5, 6, 7, 8 or 9; preferably, n1 is 5, 6, 7 or 8; and/or m1 is an integer from 1 to 6; preferably, m1 is 1, 2, 3 or 4; preferably, m1 is 1 or 2; preferably, m1 is 1; and/or Y1 is a fatty diacid containing 20-23 carbon atoms, and preferably Y1 is a fatty diacid containing 20, 21 or 22 carbon atoms, wherein formally, a hydroxyl group has been removed from one of the carboxyl groups in the fatty diacid.

In some embodiments, Y3 is: $—HN—(CH_2)_2—O—(CH_2)_2O—CH_2—CO—$, $—HN—(CH_2)_2—O—(CH_2)_2—O—(CH_2)_2—O—(CH_2)_2—O—(CH_2)_2—CO—$, $—HN—(CH_2)_2—O—(CH_2)_2—O—(CH_2)_2—O—(CH_2)_2—O—(CH_2)_2—O—(CH_2)_2—O—(CH_2)_2—CO—$, $—HN—(CH_2)_2—O—(CH_2)_2—O—(CH_2)_2—O—(CH_2)_2—O—(CH_2)_2—O—(CH_2)_2—O—(CH_2)_2—O—(CH_2)_2—CO—$, $—HN—(CH_2)_3—O—(CH_2)_4—O—(CH_2)_3—NH—CO—$, $—HN—(CH_2)_3—O—(CH_2)_4—O—(CH_2)_3—NH—CO—CH_2—O—CH_2—CO—$, $—HN—(CH_2)_3—O—(CH_2)_4—O—(CH_2)_3—NH—CO—(CH_2)_2—CO—$, $—HN—(CH_2)_2—O—(CH_2)_2O—CH_2—CO—CH_2—O—CH_2—CO—$, $—HN—(CH_2)_3—O—(CH_2)_2—O—(CH_2)_2—O—(CH_2)_3—NH—CO—(CH_2)_2—CO—$, $—HN—(CH_2)_3—O—(CH_2)_2—O—(CH_2)_2—O—(CH_2)_3—NH—CO—CH_2—O—CH_2—CO—$, $—HN—(CH_2)_2—O—(CH_2)_2—O—(CH_2)_2—NH—CO—(CH_2)_2—CO—$, $—HN—(CH_2)_2—O—(CH_2)_2—O—(CH_2)_2—NH—CO—CH_2—O—CH_2—CO—$, $—HN—(CH_2)_3—O—(CH_2)_2—O—(CH_2)_2—O—(CH_2)_3—NH—CO—CH_2—O—CH_2—CO—$, $—HN—(CH_2)_3—O—(CH_2)_3O—CH_2—CO—$, or $—HN—(CH_2)_4—O—(CH_2)_4O—CH_2—CO—$; preferably, Y3 is $—HN—(CH_2)_2—O—(CH_2)_2O—CH_2—CO—$; or Y3' is $—HN—(CH_2—CH_2—O)_{10}—CH_2—CO—$, $—HN—(CH_2—CH_2—O)_{11}—CH_2—CO—$, $—HN—(CH_2—CH_2—O)_{12}—CH_2—CO—$, or $—HN—(CH_2—CH_2—CH_2—O)_8—CH_2—CO—$; and/or Y2 is an amino acid residue selected from the group consisting of γGlu, αGlu, βAsp, αAsp, γ-D-Glu, α-D-Glu, β-D-Asp and α-D-Asp; preferably, Y2 is selected from γGlu and βAsp; and/or Y1 is $HOOC—(CH_2)_{18}—CO—$, $HOOC—(CH_2)_{19}—CO—$, $HOOC—(CH_2)_{20}—CO—$, $HOOC—(CH_2)_{21}—CO—$, $HOOC—(CH_2)_{22}—CO—$, or $HOOC—(CH_2)_{24}—CO—$; preferably, Y1 is $HOOC—(CH_2)_{18}—CO—$, $HOOC—(CH_2)_{19}—CO—$, $HOOC—(CH_2)_{20}—CO—$, $HOOC—(CH_2)_{21}—CO—$ or $HOOC—(CH_2)_{22}—CO—$; preferably, Y1 is $HOOC—(CH_2)_{18}—CO—$, $HOOC—(CH_2)_{20}—CO—$ or $HOOC—(CH_2)_{22}—CO—$.

In some embodiments, the formula (C) is linked to an amino group of the lysine residue or an N-terminal amino acid residue of the insulin parent via the C-terminal of Y3, or the formula (C') is linked to the amino group of the lysine residue or the N-terminal amino acid residue of the insulin parent via the C-terminal of Y3'.

In some embodiments, the acyl moiety is linked to an F amino group of the lysine residue of the insulin parent.

In some embodiments, the acylated insulin is selected from the group consisting of A14E, B16H, B25H, B29K(N(ε)-eicosanedioyl-γGlu-5×OEG), desB30 human insulin; A14E, B16H, B25H, B29K(N(ε)-eicosanedioyl-γGlu-6×OEG), desB30 human insulin; A14E, B16H, B25H, B29K(N(ε)-eicosanedioyl-γGlu-γGlu-5×OEG), desB30 human insulin; A14E, B16H, B25H, B29K(N(ε)-eicosanedioyl-γGlu-γGlu-6×OEG), desB30 human insulin; A14E, B16H, B25H, B29K(N(ε)-eicosanedioyl-5×OEG-γGlu), desB30 human insulin; A14E, B16H, B25H, B29K(N(ε)-eicosanedioyl-6×OEG-γGlu), desB30 human insulin; A14E, B16H, B25H, B29K(N(ε)-eicosanedioyl-6×OEG-γGlu-γGlu), desB30 human insulin; A14E, B16H, B25H, B29K(N(ε)-eicosanedioyl-5×OEG-γGlu-γGlu), desB30 human insulin; A14E, B16H, B25H, B29K(N(ε)-eicosanedioyl-βAsp-5×OEG), desB30 human insulin; A14E, B16H, B25H, B29K(N(ε)-eicosanedioyl-βAsp-6×OEG), desB30 human insulin; A14E, B16H, B25H, B29K(N(ε)-eicosanedioyl-αGlu-5×OEG), desB30 human insulin; A14E, B16H, B25H, B29K(N(ε)-eicosanedioyl-αGlu-6×OEG), desB30 human insulin; A14E, B16H, B25H, B29K(N(ε)-eicosanedioyl-αGlu-αGlu-5×OEG), desB30 human insulin; A14E, B16H, B25H, B29K(N(ε)-eicosanedioyl-αGlu-αGlu-6×OEG), desB30 human insulin; A14E, B16H, B25H, B29K(N(ε)-eicosanedioyl-αAsp-5×OEG), desB30 human insulin; A14E, B16H, B25H, B29K(N(ε)-eicosanedioyl-αAsp-6×OEG), desB30 human insulin; A14E, B16H, B25H, B29K(N(ε)-eicosanedioyl-γGlu-7×OEG), desB30 human insulin; A14E, B16H, B25H, B29K(N(ε)-eicosanedioyl-γGlu-8×OEG), desB30 human insulin; A14E, B16H, B25H, B29K(N(ε)-eicosanedioyl-γGlu-γGlu-7×OEG), desB30 human insulin; A14E, B16H, B25H, B29K(N(ε)-eicosanedioyl-γGlu-γGlu-8×OEG), desB30 human insulin; A14E, B16H, B25H, B29K(N(ε)-eicosanedioyl-7×OEG-γGlu), desB30 human insulin; A14E, B16H, B25H, B29K(N(ε)-eicosanedioyl-8×OEG-γGlu), desB30 human insulin; A14E, B16H, B25H, B29K(N(ε)-eicosanedioyl-8×OEG-γGlu-γGlu), desB30 human insulin; A14E, B16H, B25H, B29K(N(ε)-eicosanedioyl-7×OEG-γGlu-γGlu), desB30 human insulin; A14E, B16H, B25H, B29K(N(ε)-eicosanedioyl-βAsp-7×OEG), desB30 human insulin; A14E, B16H, B25H, B29K(N(ε)-eicosanedioyl-βAsp-8×OEG), desB30 human insulin; A14E, B16H, B25H, B29K(N(ε)-eicosanedioyl-αGlu-7×OEG), desB30 human insulin; A14E, B16H, B25H, B29K(N(ε)-eicosanedioyl-αGlu-8×OEG), desB30 human insulin; A14E, B16H, B25H, B29K(N(ε)-eicosanedioyl-αGlu-αGlu-7×OEG), desB30 human insulin; A14E, B16H, B25H, B29K(N(ε)-eicosanedioyl-αGlu-αGlu-8×OEG), desB30 human insulin; A14E, B16H, B25H, B29K(N(ε)-eicosanedioyl-αAsp-7×OEG), desB30 human insulin; A14E, B16H, B25H, B29K(N(ε)-eicosanedioyl-αAsp-8×OEG), desB30 human insulin; A14E, B16H, B25H, B29K(N(ε)-docosanedioyl-γGlu-5×OEG), desB30 human insulin; A14E, B16H, B25H, B29K(N(ε)-docosanedioyl-γGlu-6×OEG), desB30 human insulin; A14E, B16H, B25H, B29K(N(ε)-docosanedioyl-γGlu-γGlu-5×OEG), desB30 human insulin; A14E, B16H, B25H, B29K(N(ε)-docosanedioyl-γGlu-γGlu-6×OEG), desB30 human insulin; A14E, B16H, B25H, B29K(N(ε)-docosanedioyl-5×OEG-γGlu), desB30 human insulin; A14E, B16H, B25H, B29K(N(ε)-docosanedioyl-6×OEG-γGlu), desB30 human insulin; A14E, B16H, B25H, B29K(N(ε)-docosanedioyl-6×OEG-γGlu-γGlu), desB30 human insulin; A14E, B16H, B25H, B29K(N(ε)-docosanedioyl-5×OEG-γGlu-γGlu), desB30 human insulin; A14E, B16H, B25H, B29K(N(ε)-docosanedioyl-βAsp-5×OEG), desB30 human insulin; A14E, B16H, B25H, B29K(N(ε)-docosanedioyl-βAsp-6×OEG), desB30 human insulin; A14E, B16H, B25H, B29K(N(ε)-docosanedioyl-αGlu-5×OEG), desB30 human insulin; A14E, B16H, B25H, B29K(N(ε)-docosanedioyl-αGlu-6×OEG), desB30 human insulin; A14E, B16H, B25H, B29K(N(ε)-docosanedioyl-αGlu-αGlu-5×OEG), desB30 human insulin; A14E, B16H, B25H, B29K(N(ε)-docosanedioyl-αGlu-αGlu-6×OEG), desB30 human insulin; A14E, B16H, B25H, B29K(N(ε)-docosanedioyl-αAsp-5×OEG), desB30 human insulin; A14E, B16H, B25H, B29K(N(ε)-docosanedioyl-αAsp-6×OEG), desB30 human insulin; A14E, B16H, B25H, B29K(N(ε)-docosanedioyl-γGlu-7×OEG), desB30 human insulin; A14E, B16H, B25H, B29K(N(ε)-docosanedioyl-γGlu-8×OEG), desB30 human insulin; A14E, B16H, B25H, B29K(N(ε)-docosanedioyl-γGlu-γGlu-7×OEG), desB30 human insulin; A14E, B16H, B25H, B29K(N(ε)-docosanedioyl-γGlu-γGlu-8×OEG), desB30 human insulin; A14E, B16H, B25H, B29K(N(ε)-docosanedioyl-7×OEG-γGlu), desB30 human insulin; A14E, B16H, B25H, B29K(N(ε)-docosanedioyl-8×OEG-γGlu), desB30 human insulin; A14E, B16H, B25H, B29K(N(ε)-docosanedioyl-8×OEG-γGlu-γGlu), desB30 human insulin; A14E, B16H, B25H, B29K(N(ε)-docosanedioyl-7×OEG-γGlu-γGlu), desB30 human insulin; A14E, B16H, B25H, B29K(N(ε)-docosanedioyl-βAsp-7×OEG), desB30 human insulin; A14E, B16H, B25H, B29K(N(ε)-docosanedioyl-βAsp-8×OEG), desB30 human insulin; A14E, B16H, B25H, B29K(N(ε)-docosanedioyl-αGlu-7×OEG), desB30 human insulin; A14E, B16H, B25H, B29K(N(ε)-docosanedioyl-αGlu-8×OEG), desB30 human insulin; A14E, B16H, B25H, B29K(N(ε)-docosanedioyl-αGlu-αGlu-7×OEG), desB30 human insulin; A14E, B16H, B25H, B29K(N(ε)-docosanedioyl-αGlu-αGlu-8×OEG), desB30 human insulin; A14E, B16H, B25H, B29K(N(ε)-docosanedioyl-αAsp-7×OEG), desB30 human insulin; A14E, B16H, B25H, B29K(N(ε)-docosanedioyl-αAsp-8×OEG), desB30 human insulin; A14E, B16H, B25H, B29K(N(ε)-heneicosanedioyl-γGlu-5×OEG), desB30 human insulin; A14E, B16H, B25H, B29K(N(ε)-heneicosanedioyl-γGlu-6×OEG), desB30 human insulin; A14E, B16H, B25H, B29K(N(ε)-heneicosanedioyl-γGlu-7×OEG), desB30 human insulin; A14E, B16H, B25H, B29K(N(ε)-heneicosanedioyl-γGlu-8×OEG), desB30 human insulin; A14E, B16H, B25H, B29K(N(ε)-tricosanedioyl-γGlu-5×OEG), desB30 human insulin; A14E, B16H, B25H, B29K(N(ε)-tricosanedioyl-γGlu-6×OEG), desB30 human insulin; A14E, B16H, B25H, B29K(N(ε)-tricosanedioyl-γGlu-7×OEG), desB30 human insulin; A14E, B16H, B25H, B29K(N(ε)-tricosanedioyl-γGlu-8×OEG), desB30 human insulin; A14E, B16H, B25H, B29K(N(ε)-tetracosanedioyl-γGlu-5×OEG), desB30 human insulin; A14E, B16H, B25H, B29K(N(ε)-tetracosanedioyl-γGlu-6×OEG), desB30 human insulin; A14E, B16H, B25H, B29K(N(ε)-tetracosanedioyl-γGlu-7×OEG), desB30 human insulin; A14E, B16H, B25H, B29K(N(ε)-tetracosanedioyl-γGlu-8×OEG), desB30 human insulin; A14E, B16H, B25H, B29K(N(ε)-docosanedioyl-γGlu-9×OEG), desB30 human insulin; A14E, B16H, B25H, B29K(N(ε)-eicosanedioyl-γGlu-9×OEG), desB30 human insulin; and A14E, B16H, B25H, B29K(N(ε)-docosanedioyl-γGlu-10×OEG), desB30 human insulin;

preferably, the acylated insulin is selected from the group consisting of A14E, B16H, B25H, B29K(N(ε)-eicosanedioyl-γGlu-5×OEG), desB30 human insulin; A14E, B16H, B25H, B29K(N(ε)-eicosanedioyl-γGlu-6×OEG), desB30 human insulin; A14E, B16H, B25H, B29K(N(ε)-docosanedioyl-γGlu-5×OEG), desB30 human insulin; A14E, B16H, B25H, B29K(N(ε)-docosanedioyl-γGlu-6×OEG), desB30 human insulin; A14E, B16H, B25H, B29K(N(s)-eicosanedioyl-γGlu-7×OEG), desB30 human insulin; A14E, B16H, B25H, B29K(N(ε)-eicosanedioyl-γGlu-8×OEG), desB30 human insulin; A14E, B16H, B25H, B29K(N(ε)-docosanedioyl-γGlu-7×OEG), desB30 human insulin; A14E, B16H, B25H, B29K(N(ε)-docosanedioyl-γGlu-8×OEG), desB30 human insulin; A14E, B16H, B25H, B29K(N(ε)-eicosanedioyl-γGlu-9×OEG), desB30 human insulin; A14E, B16H, B25H, B29K(N(ε)-docosanedioyl-γGlu-9×OEG), desB30 human insulin; and A14E, B16H, B25H, B29K(N(ε)-docosanedioyl-γGlu-10×OEG), desB30 human insulin;

preferably, the acylated insulin is selected from the group consisting of A14E, B16H, B25H, B29K(N(ε)-eicosanedioyl-γGlu-6×OEG), desB30 human insulin; and A14E, B16H, B25H, B29K(N(ε)-docosanedioyl-γGlu-6×OEG), desB30 human insulin.

In another aspect, the present invention provides an insulin derivative, which is an acylated insulin, wherein the insulin parent of the acylated insulin is A14E, B16H, B25H, desB30 human insulin or A14E, B16E, B25H, desB30 human insulin, and the acyl moiety of the acylated insulin is linked to an amino group of the lysine residue or an N-terminal amino acid residue of the insulin parent, wherein the acyl moiety is shown as formula (D):

$$W1\text{-}(W2)_{m2}\text{-}(W3)_{n2}\text{-} \quad (D),$$

wherein, m2 is 0, 1, 2, 3, 4, 5, 6, 7, 8, 9 or 10, and n2 is 11, 12, 13, 14, 15, 16, 17, 18, 19 or 20;

W3 is a neutral and alkylene glycol-containing amino acid residue;

W2 is an acidic amino acid residue;

W1 is a fatty diacid containing 20-24 carbon atoms, wherein formally, a hydroxyl group has been removed from one of the carboxyl groups in the fatty diacid;

W1, W2 and W3 are linked by amide bonds; and the order of W2 and W3 presented in the formula (D) can be interchanged independently;

or the acyl moiety is shown as formula (D'):

$$W1\text{-}(W2)_{m2}\text{-}(W3')_{n2'}\text{-} \quad (D'),$$

wherein, m2 is 0, 1, 2, 3, 4, 5, 6, 7, 8, 9 or 10, and n2' is 11, 12, 13, 14, 15, 16, 17, 18, 19 or 20;

W3' is a neutral and alkylene glycol-containing amino acid residue;

W2 is an acidic amino acid residue;

W1 is a fatty diacid containing 20-24 carbon atoms, wherein formally, a hydroxyl group has been removed from one of the carboxyl groups in the fatty diacid;

W1, W2 and W3' are linked by amide bonds; and the order W2 and W3' presented in the formula (D') can be interchanged independently; and the total number of carbon atoms in $(W3')_{n2'}$ is 30-180, 42-180, preferably 61-180, preferably 66-180 or preferably 72-120.

In some embodiments, n2 is 11, 12, 13, 14, 15, 16, 17, 18 or 19; preferably, n2 is 11, 12, 13, 14, 15, 16, 17 or 18; preferably, n2 is 11, 12, 13, 14, 15 or 16; preferably, n2 is 11, 12, 13, 14 or 15; and/or m2 is an integer from 1 to 6; preferably, m2 is 1, 2, 3 or 4; preferably, m2 is 1 or 2; preferably, m2 is 1; and/or W1 is a fatty diacid containing 20-23 carbon atoms, and preferably W1 is a fatty diacid containing 20, 21 or 22 carbon atoms, wherein formally, a hydroxyl group has been removed from one of the carboxyl groups in the fatty diacid.

In some embodiments, W3 is: —HN—$(CH_2)_2$—O—$(CH_2)_2$O—$CH_2$—CO—, —HN—$(CH_2)_2$—O—$(CH_2)_2$—O—$(CH_2)_2$—O—$(CH_2)_2$—O—$(CH_2)_2$—CO—, —HN—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—CO—, —HN—$(CH_2)_2$ —O—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—CO—, —HN—$(CH_2)_3$—O—$(CH_2)_4$—O—$(CH_2)_3$ —NH—CO—, —HN—$(CH_2)_3$—O—$(CH_2)_4$—O—$(CH_2)_3$—NH—CO—$CH_2$—O—$CH_2$—CO—, —HN—$(CH_2)_3$—O—$(CH_2)_4$—O—$(CH_2)_3$—NH—CO—$(CH_2)_2$—CO—, —HN—$(CH_2)_2$—O—$(CH_2)_2$—O—$CH_2$—CO—$CH_2$—O—$CH_2$—CO—, —HN—$(CH_2)_3$—O—$(CH_2)_2$—O—$(CH_2)_2$—O—$(CH_2)_3$—NH—CO—$(CH_2)_2$—CO—, —HN—$(CH_2)_3$—O—$(CH_2)_2$—O—$(CH_2)_2$—O—$(CH_2)_3$—NH—CO—$CH_2$—O—$CH_2$—CO—, —HN—$(CH_2)_2$—O—$(CH_2)_2$—O—$(CH_2)_2$—NH—CO—$(CH_2)_2$—CO—, —HN—$(CH_2)_2$—O—$(CH_2)_2$—O—$(CH_2)_2$—NH—CO—$CH_2$—O—$CH_2$—CO—, —HN—$(CH_2)_3$—O—$(CH_2)_2$—O—$(CH_2)_2$—O—$(CH_2)_3$—NH—CO—$CH_2$—O—$CH_2$—CO—, —HN—$(CH_2)_3$—O—$(CH_2)_3$O—$CH_2$—CO—, or —HN—$(CH_2)_4$—O—$(CH_2)_4$O—$CH_2$—CO—; preferably, W3 is —HN—$(CH_2)_2$—O—$(CH_2)_2$—O—$CH_2$—CO—; or W3' is —HN—$(CH_2$—$CH_2$—$O)_2$O—$CH_2$—CO—, —HN—$(CH_2$—$CH_2$—$O)_{22}$—$CH_2$—CO—, —HN—$(CH_2$—$CH_2$—$O)_{24}$—$CH_2$—CO—, or —HN—$(CH_2$—$CH_2$—$CH_2$—$O)_{15}$—$CH_2$—CO—; and/or W2 is an amino acid residue selected from the group consisting of γGlu, αGlu, βAsp, αAsp, γ-D-Glu, α-D-Glu, β-D-Asp and α-D-Asp; preferably, W2 is selected from γGlu and βAsp; and/or W1 is HOOC—$(CH_2)_{18}$—CO—, HOOC—$(CH_2)_{19}$—CO—, HOOC—$(CH_2)_{20}$—CO—, HOOC—$(CH_2)_{21}$—CO— or HOOC—$(CH_2)_{22}$—CO—; preferably, W1 is HOOC—$(CH_2)_{18}$—CO—, HOOC—$(CH_2)_{20}$—CO— or HOOC—$(CH_2)_{22}$—CO—.

In some embodiments, the formula (D) is linked to an amino group of the lysine residue or an N-terminal amino acid residue of the insulin parent via the C-terminal of W3, or the formula (D') is linked to the amino group of the lysine residue or the N-terminal amino acid residue of the insulin parent via the C-terminal of W3'.

In some embodiments, the acyl moiety is linked to an F amino group of the lysine residue of the insulin parent.

In some embodiments, the acylated insulin is selected from the group consisting of A14E, B16H, B25H, B29K(N(ε)-eicosanedioyl-γGlu-12×OEG), desB30 human insulin; A14E, B16H, B25H, B29K(N(ε)-docosanedioyl-γGlu-12×OEG), desB30 human insulin; A14E, B16H, B25H, B29K(N(ε)-eicosanedioyl-γGlu-11×OEG), desB30 human insulin; A14E, B16H, B25H, B29K(N(ε)-docosanedioyl-γGlu-11×OEG), desB30 human insulin; A14E, B16H, B25H, B29K(N(ε)-heneicosanedioyl-γGlu-12×OEG), desB30 human insulin; A14E, B16H, B25H, B29K(N(ε)-tricosanedioyl-γGlu-12×OEG), desB30 human insulin; A14E, B16H, B25H, B29K(N(ε)-tetracosanedioyl-γGlu-12×OEG), desB30 human insulin; A14E, B16H, B25H, B29K(N(ε)-eicosanedioyl-γGlu-13×OEG), desB30 human insulin; A14E, B16H, B25H, B29K(N(ε)-eicosanedioyl-γGlu-14×OEG), desB30 human insulin; A14E, B16H, B25H, B29K(N(ε)-eicosanedioyl-γGlu-15×OEG), desB30 human insulin; A14E, B16H, B25H, B29K(N(ε)-docosanedioyl-γGlu-13×OEG), desB30 human insulin; A14E, B16H, B25H, B29K(N(ε)-docosanedioyl-γGlu-14×OEG), desB30 human insulin; A14E, B16H, B25H, B29K(N(ε)-docosanedioyl-γGlu-15×OEG), desB30 human insulin; A14E, B16H, B25H, B29K(N(ε)-eicosanedioyl-γGlu-16×OEG), desB30 human insulin; A14E, B16H, B25H, B29K(N(ε)-eicosanedioyl-γGlu-17×OEG), desB30 human insulin; A14E, B16H, B25H, B29K(N(ε)-docosanedioyl-γGlu-16×OEG), desB30 human insulin; A14E, B16H, B25H, B29K(N(ε)-docosanedioyl-γGlu-17×OEG), desB30 human insulin; A14E, B16H, B25H, B29K(N(ε)-eicosanedioyl-γGlu-18×OEG), desB30 human insulin; A14E, B16H, B25H, B29K(N(ε)-eicosanedioyl-γGlu-19×OEG), desB30 human insulin; A14E, B16H, B25H, B29K(N(ε)-docosanedioyl-γGlu-18×OEG), desB30 human insulin; A14E, B16H, B25H, B29K(N(ε)-docosanedioyl-γGlu-19×OEG), desB30 human insulin; A14E, B16H, B25H, B29K(N(ε)-eicosanedioyl-γGlu-20×OEG), desB30 human insulin; A14E, B16H, B25H, B29K(N(ε)-docosanedioyl-γGlu-20×OEG), desB30 human insulin; A14E, B16E, B25H, B29K(N(ε)-eicosanedioyl-γGlu-16×OEG), desB30 human insulin; A14E, B16E, B25H, B29K(N(ε)-eicosanedioyl-γGlu-17×OEG), desB30 human insulin; A14E, B16E, B25H, B29K(N(ε)-docosanedioyl-γGlu-16×OEG), desB30 human insulin; A14E, B16E, B25H, B29K(N(ε)-docosanedioyl-γGlu-17×OEG), desB30 human insulin; A14E, B16E, B25H, B29K(N(ε)-eicosanedioyl-γGlu-18×OEG), desB30 human insulin; A14E, B16E, B25H, B29K(N(ε)-eicosanedioyl-γGlu-19×OEG), desB30 human insulin; A14E, B16E, B25H, B29K(N(ε)-docosanedioyl-γGlu-18×OEG), desB30 human insulin; A14E, B16E, B25H, B29K(N(ε)-docosanedioyl-γGlu-19×OEG), desB30 human insulin; A14E, B16E, B25H, B29K(N(ε)-eicosanedioyl-γGlu-20×OEG), desB30 human insulin; A14E, B16E, B25H, B29K(N(ε)-docosanedioyl-γGlu-20×OEG), desB30 human insulin; and A14E, B16H, B25H, B29K(N(ε)-docosanedioyl-γGlu-24×OEG), desB30 human insulin;

preferably, the acylated insulin is selected from the group consisting of A14E, B16H, B25H, B29K(N(ε)-eicosanedioyl-γGlu-11×OEG), desB30 human insulin; A14E, B16H, B25H, B29K(N(ε)-eicosanedioyl-γGlu-12×OEG), desB30 human insulin; A14E, B16H, B25H, B29K(N(ε)-docosanedioyl-γGlu-11×OEG), desB30 human insulin; A14E, B16H, B25H, B29K(N(ε)-docosanedioyl-γGlu-12×OEG), desB30 human insulin; and A14E, B16H, B25H, B29K(N(ε)-docosanedioyl-γGlu-18×OEG), desB30 human insulin;

preferably, the acylated insulin is selected from the group consisting of A14E, B16H, B25H, B29K(N(ε)-eicosanedioyl-γGlu-12×OEG), desB30 human insulin; and A14E, B16H, B25H, B29K(N(ε)-docosanedioyl-γGlu-12×OEG), desB30 human insulin.

In some embodiments, the acylated insulin is selected from the group consisting of A14E, B16E, B25H, B29K(N(ε)-eicosanedioyl-γGlu-5×OEG), desB30 human insulin; A14E, B16E, B25H, B29K(N(ε)-eicosanedioyl-γGlu-6×OEG), desB30 human insulin; A14E, B16E, B25H, B29K(N(ε)-eicosanedioyl-γGlu-γGlu-5×OEG), desB30 human insulin; A14E, B16E, B25H, B29K(N(ε)-eicosanedioyl-γGlu-γGlu-6×OEG), desB30 human insulin; A14E, B16E, B25H, B29K(N(ε)-eicosanedioyl-5×OEG-γGlu), desB30 human insulin; A14E, B16E, B25H, B29K(N(ε)-eicosanedioyl-6×OEG-γGlu), desB30 human insulin; A14E, B16E, B25H, B29K(N(ε)-eicosanedioyl-6×OEG-γGlu-γGlu), desB30 human insulin; A14E, B16E, B25H, B29K(N(ε)-eicosanedioyl-5×OEG-γGlu-γGlu), desB30 human insulin; A14E, B16E, B25H, B29K(N(ε)-eicosanedioyl-βAsp-5×OEG), desB30 human insulin; A14E, B16E, B25H, B29K(N(ε)-eicosanedioyl-βAsp-6×OEG), desB30 human insulin; A14E, B16E, B25H, B29K(N(ε)-eicosanedioyl-αGlu-5×OEG), desB30 human insulin; A14E, B16E, B25H, B29K(N(ε)-eicosanedioyl-αGlu-6×OEG), desB30 human insulin; A14E, B16E, B25H, B29K(N(ε)-eicosanedioyl-αGlu-αGlu-5×OEG), desB30 human insulin; A14E, B16E, B25H, B29K(N(ε)-eicosanedioyl-αGlu-αGlu-6×OEG), desB30 human insulin; A14E, B16E, B25H, B29K(N(ε)-eicosanedioyl-αAsp-5×OEG), desB30 human insulin; A14E, B16E, B25H, B29K(N(ε)-eicosanedioyl-αAsp-6×OEG), desB30 human insulin; A14E, B16E, B25H, B29K(N(ε)-eicosanedioyl-γGlu-7×OEG), desB30 human insulin; A14E, B16E, B25H, B29K(N(ε)-eicosanedioyl-γGlu-8×OEG), desB30 human insulin; A14E, B16E, B25H, B29K(N(ε)-eicosanedioyl-γGlu-γGlu-7×OEG), desB30 human insulin; A14E, B16E, B25H, B29K(N(ε)-eicosanedioyl-γGlu-γGlu-8×OEG), desB30 human insulin; A14E, B16E, B25H, B29K(N(ε)-eicosanedioyl-7×OEG-γGlu), desB30 human insulin; A14E, B16E, B25H, B29K(N(ε)-eicosanedioyl-8×OEG-γGlu), desB30 human insulin; A14E, B16E, B25H, B29K(N(ε)-eicosanedioyl-8×OEG-γGlu-γGlu), desB30 human insulin; A14E, B16E, B25H, B29K(N(ε)-eicosanedioyl-7×OEG-γGlu-γGlu), desB30 human insulin; A14E, B16E, B25H, B29K(N(ε)-eicosanedioyl-βAsp-7×OEG), desB30 human insulin; A14E, B16E, B25H, B29K(N(ε)-eicosanedioyl-βAsp-8×OEG), desB30 human insulin; A14E, B16E, B25H, B29K(N(ε)-eicosanedioyl-αGlu-7×OEG), desB30 human insulin; A14E, B16E, B25H, B29K(N(ε)-eicosanedioyl-αGlu-8×OEG), desB30 human insulin; A14E, B16E, B25H, B29K(N(ε)-eicosanedioyl-αGlu-αGlu-7×OEG), desB30 human insulin; A14E, B16E, B25H, B29K(N(ε)-eicosanedioyl-αGlu-αGlu-8×OEG), desB30 human insulin; A14E, B16E, B25H, B29K(N(ε)-eicosanedioyl-αAsp-7×OEG), desB30 human insulin; A14E, B16E, B25H, B29K(N(ε)-eicosanedioyl-αAsp-8×OEG), desB30 human insulin; A14E, B16E, B25H, B29K(N(ε)-docosanedioyl-γGlu-5×OEG), desB30 human insulin; A14E, B16E, B25H, B29K(N(ε)-docosanedioyl-γGlu-6×OEG), desB30 human insulin; A14E, B16E, B25H, B29K(N(ε)-docosanedioyl-γGlu-γGlu-5×OEG), desB30 human insulin; A14E, B16E, B25H, B29K(N(ε)-docosanedioyl-γGlu-γGlu-6×OEG), desB30 human insulin; A14E, B16E, B25H, B29K(N(ε)-docosanedioyl-5×OEG-γGlu), desB30 human insulin; A14E, B16E, B25H, B29K(N(ε)-docosanedioyl-6×OEG-γGlu), desB30 human insulin; A14E, B16E, B25H, B29K(N(ε)-docosanedioyl-6×OEG-γGlu-γGlu), desB30 human insulin; A14E, B16E, B25H, B29K(N(ε)-docosanedioyl-5×OEG-γGlu-γGlu), desB30 human insulin; A14E, B16E, B25H, B29K(N(ε)-docosanedioyl-βAsp-5×OEG), desB30 human insulin; A14E, B16E, B25H, B29K(N(ε)-docosanedioyl-βAsp-6×OEG), desB30 human insulin; A14E, B16E, B25H, B29K(N(ε)-docosanedioyl-αGlu-5×OEG), desB30 human insulin; A14E, B16E, B25H, B29K(N(ε)-docosanedioyl-αGlu-6×OEG), desB30 human insulin; A14E, B16E, B25H, B29K(N(ε)-docosanedioyl-αGlu-αGlu-5×OEG), desB30 human insulin; A14E, B16E, B25H, B29K(N(ε)-docosanedioyl-αGlu-αGlu-6×OEG), desB30 human insulin; A14E, B16E, B25H, B29K(N(ε)-docosanedioyl-αAsp-5×OEG), desB30 human insulin; A14E, B16E, B25H, B29K(N(ε)-docosanedioyl-αAsp-6×OEG), desB30 human insulin; A14E, B16E, B25H, B29K(N(ε)-docosanedioyl-γGlu-7×OEG), desB30 human insulin; A14E, B16E, B25H, B29K(N(ε)-docosanedioyl-γGlu-8×OEG), desB30 human insulin; A14E, B16E, B25H, B29K(N(ε)-docosanedioyl-γGlu-γGlu-7×OEG), desB30 human insulin; A14E, B16E, B25H, B29K(N(ε)-docosanedioyl-γGlu-γGlu-8×OEG), desB30 human insulin; A14E, B16E, B25H, B29K(N(ε)-docosanedioyl-7×OEG-γGlu), desB30 human insulin; A14E, B16E, B25H, B29K(N(ε)-docosanedioyl-8×OEG-γGlu), desB30 human insulin; A14E, B16E, B25H, B29K(N(ε)-docosanedioyl-8×OEG-γGlu-γGlu), desB30 human insulin; A14E, B16E, B25H, B29K(N(ε)-docosanedioyl-7×OEG-γGlu-γGlu), desB30 human insulin; A14E, B16E, B25H, B29K(N(ε)-docosanedioyl-βAsp-7×OEG), desB30 human insulin; A14E, B16E, B25H, B29K(N(ε)-docosanedioyl-βAsp-8×OEG), desB30 human insulin; A14E, B16E, B25H, B29K(N(ε)-docosanedioyl-αGlu-7×OEG), desB30 human insulin; A14E, B16E, B25H, B29K(N(ε)-docosanedioyl-αGlu-8×OEG), desB30 human insulin; A14E, B16E, B25H, B29K(N(ε)-docosanedioyl-αGlu-αGlu-7×OEG), desB30 human insulin; A14E, B16E, B25H, B29K(N(ε)-docosanedioyl-αGlu-αGlu-8×OEG), desB30 human insulin; A14E, B16E, B25H, B29K(N(ε)-docosanedioyl-αAsp-7×OEG), desB30 human insulin; A14E, B16E, B25H, B29K(N(ε)-docosanedioyl-αAsp-8×OEG), desB30 human insulin; A14E, B16E, B25H, B29K(N(ε)-heneicosanedioyl-γGlu-5×OEG), desB30 human insulin; A14E, B16E, B25H, B29K(N(ε)-heneicosanedioyl-γGlu-6×OEG), desB30 human insulin; A14E, B16E, B25H, B29K(N(ε)-heneicosanedioyl-γGlu-7×OEG), desB30 human insulin; A14E, B16E, B25H, B29K(N(ε)-heneicosanedioyl-γGlu-8×OEG), desB30 human insulin; A14E, B16E, B25H, B29K(N(ε)-tricosanedioyl-γGlu-5×OEG), desB30 human insulin; A14E, B16E, B25H, B29K(N(ε)-tricosanedioyl-γGlu-6×OEG), desB30 human insulin; A14E, B16E, B25H, B29K(N(ε)-tricosanedioyl-γGlu-7×OEG), desB30 human insulin; A14E, B16E, B25H, B29K(N(ε)-tricosanedioyl-γGlu-8×OEG), desB30 human insulin; A14E, B16E, B25H, B29K(N(ε)-tetracosanedioyl-γGlu-5×OEG), desB30 human insulin; A14E, B16E, B25H, B29K(N(ε)-tetracosanedioyl-γGlu-6×OEG), desB30 human insulin; A14E, B16E, B25H, B29K(N(ε)-tetracosanedioyl-γGlu-7×OEG), desB30 human insulin; A14E, B16E, B25H, B29K(N(ε)-tetracosanedioyl-γGlu-8×OEG), desB30 human insulin; A14E, B16E, B25H, B29K(N(ε)-eicosanedioyl-γGlu-12×OEG), desB30 human insulin; A14E, B16E, B25H, B29K(N(ε)-docosanedioyl-γGlu-12×OEG), desB30 human insulin; A14E, B16E, B25H, B29K(N(ε)-eicosanedioyl-γGlu-9×OEG), desB30 human insulin; A14E, B16E, B25H, B29K(N(ε)-eicosanedioyl-γGlu-10×OEG), desB30 human insulin; A14E, B16E, B25H, B29K(N(ε)-eicosanedioyl-γGlu-11×OEG), desB30 human insulin; A14E, B16E, B25H, B29K(N(ε)-docosanedioyl-γGlu-9×OEG), desB30 human insulin; A14E, B16E, B25H, B29K(N(ε)-docosanedioyl-γGlu-10×OEG), desB30 human insulin; A14E, B16E, B25H, B29K(N(ε)-docosanedioyl-γGlu-11×OEG), desB30 human insulin; A14E, B16E, B25H, B29K(N(ε)-heneicosanedioyl-γGlu-12×OEG), desB30 human insulin; A14E, B16E, B25H, B29K(N(ε)-tricosanedioyl-γGlu-12×OEG), desB30 human insulin; and A14E, B16E, B25H, B29K(N(ε)-tetracosanedioyl-γGlu-12×OEG), desB30 human insulin.

In another aspect, the present invention provides a pharmaceutical composition comprising the insulin derivatives disclosed herein or A14E, B16H, B25H, B29K(N(ε)-eicosanedioyl-γGlu-10×OEG), desB30 human insulin, and one or more pharmaceutically acceptable excipients.

In some embodiments, the pharmaceutical composition comprises at least 1.5 moles of zinc ions/6 moles of the acylated insulin; preferably at least 2.2 moles of zinc ions/6 moles of the acylated insulin; preferably at least 3.5 moles of zinc ions/6 moles of the acylated insulin; preferably at least 4.5 moles of zinc ions/6 moles of the acylated insulin; preferably 2.2-12 moles of zinc ions/6 moles of the acylated insulin; more preferably 4.5-10 moles of zinc ions/6 moles of the acylated insulin; more preferably 4.5-8 moles of zinc ions/6 moles of the acylated insulin; more preferably 4.5-7.5 moles of zinc ions/6 moles of the acylated insulin; more preferably 4.5-7.0 moles of zinc ions/6 moles of the acylated insulin; or more preferably 4.5-6.5 moles of zinc ions/6 moles of the acylated insulin; and/or the pharmaceutical composition has a pH value in the range from 6.5 to 8.5; preferably, the pH value is 6.8-8.2; preferably, the pH value is 7.0-8.2; preferably, the pH value is 7.2-7.6; more preferably, the pH value is 7.4 or 7.6.

In some embodiments, the pharmaceutical composition further comprises glycerol, phenol, m-cresol, NaCl and/or $Na_2HPO_4$; preferably, the pharmaceutical composition further comprises glycerol, phenol and NaCl; preferably, the pharmaceutical composition further comprises glycerol, phenol, m-cresol and NaCl; preferably, the pharmaceutical composition further comprises glycerol, phenol, NaCl and $Na_2HPO_4$; more preferably, the pharmaceutical composition further comprises glycerol, phenol, m-cresol, NaCl and $Na_2HPO_4$.

In some embodiments, the content of glycerol is no more than about 2.5% (w/w), preferably no more than about 2% (w/w), preferably about 0.3% to about 2% (w/w), preferably about 0.5% to about 1.8% (w/w), preferably about 0.7% to about 1.8% (w/w), or more preferably about 1% to about 1.8% (w/w); and/or the content of phenol is about 16-80 mM, preferably about 25-75 mM, preferably about 30-70 mM, 45-70 mM, preferably about 45-65 mM, preferably about 45 mM, preferably about 46 mM, about 47 mM, about 48 mM, about 49 mM, 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM or about 65 mM; and/or the content of m-cresol is about 0-35 mM, preferably about 0-19 mM, preferably about 0-15 mM, preferably about 0 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM or about 15 mM; and/or the content of NaCl is about 0-150 mM, preferably about 5-120 mM, preferably about 10-120 mM, preferably about 10-100 mM, more preferably about 10-75 mM, more preferably about 10-50 mM, or more preferably about 10-30 mM; and/or the content of $Na_2HPO_4$ is about 0-75 mM, preferably about 5-60 mM, preferably less than about 50 mM, more preferably less than about 25 mM, or more preferably less than about 15 mM; and/or the content of insulin derivative is more than about 0.3 mM, preferably more than about 0.6 mM, preferably about 0.3-12 mM, preferably about 0.6-9.0 mM, preferably about 0.6-8.4 mM, preferably about 0.6-7.2 mM, preferably about 0.6-6.0 mM, preferably about 0.6-4.2 mM, preferably about 0.6-3.6 mM, preferably about 0.6-3.0 mM, preferably about 0.6-2.4 mM, preferably about 0.6-2.1 mM, or preferably about 0.6-1.2 mM.

In some embodiments, the insulin derivative is B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-8×OEG), desB30 human insulin; B29K(N(ε)-docosanedioyl-γGlu-8×OEG), desB30 human insulin; B29K(N(ε)-docosanedioyl-γGlu-12×OEG), desB30 human insulin; A14E, B16H, B25H, B29K(N(ε)-eicosanedioyl-γGlu-6×OEG), desB30 human insulin; A14E, B16H, B25H, B29K(N(ε)-docosanedioyl-γGlu-6×OEG), desB30 human insulin; A14E, B16H, B25H, B29K(N(ε)-eicosanedioyl-γGlu-10×OEG), desB30 human insulin; A14E, B16H, B25H, B29K(N(ε)-docosanedioyl-γGlu-10×OEG), desB30 human insulin; A14E, B16H, B25H, B29K(N(ε)-eicosanedioyl-γGlu-12×OEG), desB30 human insulin; or A14E, B16H, B25H, B29K(N(ε)-docosanedioyl-γGlu-12×OEG), desB30 human insulin.

In another aspect, the present invention provides a pharmaceutical composition comprising about 0.6-4.2 mM insulin derivative of the present invention described above, about 1% to about 1.8% (w/w) glycerol, about 45-65 mM phenol, about 4.5-6.5 moles of zinc ions/6 moles of the insulin derivative, about 10-120 mM sodium chloride and about 0-15 mM m-cresol and having a pH value of about 7.0-8.2, wherein preferably, the insulin derivative is B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-8×OEG), desB30 human insulin; B29K(N(ε)-docosanedioyl-γGlu-8×OEG), desB30 human insulin; B29K(N(ε)-docosanedioyl-γGlu-12×OEG), desB30 human insulin; A14E, B16H, B25H, B29K(N(ε)-eicosanedioyl-γGlu-6×OEG), desB30 human insulin; A14E, B16H, B25H, B29K(N(ε)-docosanedioyl-γGlu-6×OEG), desB30 human insulin; A14E, B16H, B25H, B29K(N(ε)-docosanedioyl-γGlu-10×OEG), desB30 human insulin; A14E, B16H, B25H, B29K(N(ε)-eicosanedioyl-γGlu-10×OEG), desB30 human insulin; A14E, B16H, B25H, B29K(N(ε)-eicosanedioyl-γGlu-12×OEG), desB30 human insulin; or A14E, B16H, B25H, B29K(N(ε)-docosanedioyl-γGlu-12×OEG), desB30 human insulin.

In another aspect, the present invention provides a pharmaceutical composition comprising about 0.6 mM or 1.2 mM insulin derivative of the present invention described above, 1.7% (w/w) glycerol, about 45 mM phenol, about 10 mM m-cresol, about 6.5 moles of zinc ions/6 moles of the insulin derivative and about 20 mM sodium chloride and having a pH value of about 7.0-8.0, wherein preferably, the insulin derivative is B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-8×OEG), desB30 human insulin; B29K(N(ε)-docosanedioyl-γGlu-8×OEG), desB30 human insulin; B29K(N(ε)-docosanedioyl-γGlu-12×OEG), desB30 human insulin; A14E, B16H, B25H, B29K(N(ε)-eicosanedioyl-γGlu-6×OEG), desB30 human insulin; A14E, B16H, B25H, B29K(N(ε)-docosanedioyl-γGlu-6×OEG), desB30 human insulin; A14E, B16H, B25H, B29K(N(ε)-docosanedioyl-γGlu-10×OEG), desB30 human insulin; A14E, B16H, B25H, B29K(N(ε)-eicosanedioyl-γGlu-10×OEG), desB30 human insulin; A14E, B16H, B25H, B29K(N(ε)-eicosanedioyl-γGlu-12×OEG), desB30 human insulin; or A14E, B16H, B25H, B29K(N(ε)-docosanedioyl-γGlu-12×OEG), desB30 human insulin.

In another aspect, the present invention provides a pharmaceutical composition comprising about 0.6-4.2 mM insulin derivative of the present invention described above, about 1% to about 2% (preferably about 1.5%-1.7%) (w/w) glycerol, about 15-60 mM (preferably about 30-60 mM, more preferably about 45-60 mM) phenol, about 1.5-7.0 (preferably about 2.2-4.5) moles of zinc ions/6 moles of the insulin derivative, about 10-120 mM (preferably about 20-50 mM) sodium chloride and about 0-25 mM (preferably about 0-15 mM or 0-10 mM) m-cresol and having a pH value of about 7.0-8.2, wherein preferably, the insulin derivative is B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-8×OEG), desB30 human insulin; B29K(N(ε)-docosanedioyl-γGlu-8×OEG), desB30 human insulin; B29K(N(ε)-docosanedioyl-γGlu-12×OEG), desB30 human insulin; A14E, B16H, B25H, B29K(N(ε)-eicosanedioyl-γGlu-6×OEG), desB30 human insulin; A14E, B16H, B25H, B29K(N(ε)-docosanedioyl-γGlu-6×OEG), desB30 human insulin; A14E, B16H, B25H, B29K(N(ε)-docosanedioyl-γGlu-10×OEG), desB30 human insulin; A14E, B16H, B25H, B29K(N(ε)-eicosanedioyl-γGlu-10×OEG), desB30 human insulin; A14E, B16H, B25H, B29K(N(ε)-eicosanedioyl-γGlu-12×OEG), desB30 human insulin; or A14E, B16H, B25H, B29K(N(ε)-docosanedioyl-γGlu-12×OEG), desB30 human insulin.

In another aspect, the present invention provides a pharmaceutical composition comprising about 0.6-4.2 mM insulin derivative of the present invention described above, about 1.5%-1.7% (w/w) glycerol, about 45-60 mM phenol, about 0-10 mM m-cresol, about 2.2-2.5 moles of zinc ions/6 moles of the insulin derivative and about 20 mM sodium chloride and having a Ph value of about 7.0-8.0, wherein the insulin derivative is A14E, B16H, B25H, B29K(N(ε)-eicosanedioyl-γGlu-6×OEG), desB30 human insulin; A14E, B16H, B25H, B29K(N(ε)-docosanedioyl-γGlu-6×OEG), desB30 human insulin; A14E, B16H, B25H, B29K(N(ε)-docosanedioyl-γGlu-10×OEG), desB30 human insulin; A14E, B16H, B25H, B29K(N(ε)-eicosanedioyl-γGlu-10×OEG), desB30 human insulin; A14E, B16H, B25H, B29K(N(ε)-eicosanedioyl-γGlu-12×OEG), desB30 human insulin; or A14E, B16H, B25H, B29K(N(ε)-docosanedioyl-γGlu-12×OEG), desB30 human insulin.

In some embodiments, the pharmaceutical composition further comprises an insulinotropic GLP-1 compound; preferably, the pharmaceutical composition further comprises an insulinotropic GLP-1 compound selected from the group consisting of N-$\varepsilon^{26}$-(17-carboxyheptadecanoylamino)-4(S)-carboxybutanoyl-[Arg34]GLP-1-(7-37) peptide, N-$\varepsilon^{26}$-(17-carboxyheptadecanoylamino)-4(S)-carboxybutanoyl-[Gly8, Arg34]GLP-1-(7-37) peptide, N-$\varepsilon^{26}$-[2-(2-[2-(2-[2-(2-[4-(17-carboxyheptadecanoylamino)-4(S)-carboxybutanoylamino]ethoxy)ethoxy]acetylamino)ethoxy]ethoxy)acetyl][Aib8, Arg34]GLP-1-(7-37) peptide, and N-$\varepsilon^{26}$-[2-(2-[2-(2-[2-(2-[4-(17-carboxyheptadecanoylamino)-4(S)-carboxybutanoylamino]ethoxy)ethoxy]acetylamino)ethoxy]ethoxy)acetyl][Gly8, Arg34]GLP-1-(7-37) peptide.

In some embodiments, the pharmaceutical composition further comprises an insulinotropic GLP-1 compound shown as formula (B) or a pharmaceutically acceptable salt, amide or ester thereof:

$$[\text{Acy-(L1)}_r\text{-(L2)}_q]\text{-G1} \qquad \text{(B)},$$

wherein G1 is a GLP-1 analogue having Arg and Ala or Gly, respectively, at positions corresponding to position 34 and position 8, respectively, of GLP-1(7-37) (SEQ ID NO: 15), and [Acy-(L1)$_r$-(L2)$_q$] is a substituent linked to an F amino group of the Lys residue at position 26 of the GLP-1 analogue, wherein r is an integer from 1 to 10, and q is 0 or an integer from 1 to 10;

Acy is a fatty diacid containing 20-24 carbon atoms, wherein formally, a hydroxyl group has been removed from one of the carboxyl groups in the fatty diacid;

L1 is an amino acid residue selected from the group consisting of γGlu, αGlu, βAsp, αAsp, γ-D-Glu, α-D-Glu, β-D-Asp and α-D-Asp;

L2 is a neutral and alkylene glycol-containing amino acid residue;

Acy, L1 and L2 are linked by amide bonds; and the order of L1 and L2 presented in the formula (B) can be interchanged independently.

In some embodiments, G1 is a [Gly8, Arg34]GLP-1-(7-37) peptide (SEQ ID NO: 16) or a [Arg34]GLP-1-(7-37) peptide (SEQ ID NO: 17), and preferably is a [Gly8, Arg34]GLP-1-(7-37) peptide; and/or r is 1, 2, 3, 4, 5 or 6; preferably, r is 1, 2, 3 or 4; preferably, r is 1 or 2; preferably, r is 1; and/or q is 0, 1, 2, 3, 4, 5, 6, 7 or 8; preferably, q is 0, 1, 2, 3 or 4; more preferably, q is 0, 1 or 2; and/or Acy is a fatty diacid containing 20-23 carbon atoms, and preferably Acy is a fatty diacid containing 20, 21 or 22 carbon atoms, wherein formally, a hydroxyl group has been removed from one of the carboxyl groups in the fatty diacid.

In some embodiments, L2 is: —HN—$(CH_2)_2$—O—$(CH_2)_2$O—$CH_2$—CO—, —HN—$(CH_2)_2$—O—$(CH_2)_2$—O—$(CH_2)_2$—O—$(CH_2)_2$—O—$(CH_2)_2$—CO—, —HN—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—CO—, —HN—$(CH_2)_2$ —O—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—CO—, —HN—$(CH_2)_3$—O—$(CH_2)_4$—O—$(CH_2)_3$ —NH—CO—, —HN—$(CH_2)_3$—O—$(CH_2)_4$—O—$(CH_2)_3$—NH—CO—$CH_2$—O—$CH_2$—CO—, —HN—$(CH_2)_3$—O—$(CH_2)_4$—O—$(CH_2)_3$—NH—CO—$(CH_2)_2$—CO—, —HN—$(CH_2)_2$—O—$(CH_2)_2$O—$CH_2$—CO—$CH_2$—O—$CH_2$—CO—, —HN—$(CH_2)_3$—O—$(CH_2)_2$—O—$(CH_2)_2$—O—$(CH_2)_3$—NH—CO—$(CH_2)_2$—CO—, —HN—$(CH_2)_3$—O—$(CH_2)_2$—O—$(CH_2)_2$—O—$(CH_2)_3$—NH—CO—$CH_2$—O—$CH_2$—CO—, —HN—$(CH_2)_2$—O—$(CH_2)_2$—O—$(CH_2)_2$—NH—CO—$(CH_2)_2$—CO—, —HN—$(CH_2)_2$—O—$(CH_2)_2$—O—$(CH_2)_2$—NH—CO—$CH_2$—O—$CH_2$—CO—, —HN—$(CH_2)_3$—O—$(CH_2)_2$—O—$(CH_2)_2$—O—$(CH_2)_3$—NH—CO—$CH_2$—O—$CH_2$—CO—, —HN—$(CH_2)_3$—O—$(CH_2)_3$O—$CH_2$—CO—, or —HN—$(CH_2)_4$—O—$(CH_2)_4$O—$CH_2$—CO—; preferably, L2 is —HN—$(CH_2)_2$—O—$(CH_2)_2$O—$CH_2$—CO—; and/or L1 is selected from γGlu and βAsp; preferably, L1 is γGlu; and/or Acy is HOOC—$(CH_2)_{18}$—CO—, HOOC—$(CH_2)_{19}$—CO—, HOOC—$(CH_2)_{20}$—CO—, HOOC—$(CH_2)_{21}$—CO— or HOOC—$(CH_2)_{22}$—CO—; preferably, Acy is HOOC—$(CH_2)_{18}$—CO—, HOOC—$(CH_2)_{20}$—CO— or HOOC—$(CH_2)_{22}$—CO—.

In some embodiments, the Acy, L1 and L2 in the formula (B) are sequentially linked by amide bonds, and the C-terminal of L2 is linked to the F amino group of the Lys residue at position 26 of the GLP-1 analogue.

In some embodiments, the insulinotropic GLP-1 compound is selected from the group consisting of N-ε$^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide, N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[21-carboxyheneicosanoylamino]-4(S)-carboxybutanoylamino)ethoxy]ethoxy)acetyl][Gly8, Arg34]GLP-1-(7-37) peptide, N-ε$^{26}$-[2-(2-[2-(2-[2-(2-[4-(23-carboxytricosanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[23-carboxytricosanoylamino]-4(S)-carboxybutanoylamino)ethoxy]ethoxy)acetyl][Gly8, Arg34]GLP-1-(7-37) peptide, N-ε$^{26}$-(23-carboxytricosanoylamino)-4(S)-carboxybutanoyl-[Gly8, Arg34]GLP-1-(7-37) peptide, N-ε$^{26}$-(19-carboxynonadecanoylamino)-4(S)-carboxybutanoyl-[Gly8, Arg34]GLP-1-(7-37) peptide, N-ε$^{26}$-(21-carboxyheneicosanoylamino)-4(S)-carboxybutanoyl-[Gly8, Arg34]GLP-1-(7-37) peptide, N-ε$^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Arg34]GLP-1-(7-37) peptide, N-ε$^{26}$-[2-(2-[2-(4-[19-carboxynonadecanoylamino]-4(S)-carboxybutanoylamino)ethoxy]ethoxy)acetyl][Arg34]GLP-1-(7-37) peptide, N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Arg34]GLP-1-(7-37) peptide, N-ε$^{26}$-[2-(2-[2-(4-[21-carboxyheneicosanoylamino]-4(S)-carboxybutanoylamino)ethoxy]ethoxy)acetyl][Arg34]GLP-1-(7-37) peptide, N-ε$^{26}$-[2-(2-[2-(2-[2-(2-[4-(23-carboxytricosanoylamino)-4(S)-carboxybutanoylamino]ethoxy)ethoxy]acetylamino)ethoxy]ethoxy)acetyl][Arg34]GLP-1-(7-37) peptide, N-ε$^{26}$-[2-(2-[2-(4-[23-carboxytricosanoylamino]-4(S)-carboxybutanoylamino)ethoxy]ethoxy)acetyl][Arg34]GLP-1-(7-37) peptide, N-ε$^{26}$-(23-carboxytricosanoylamino)-4(S)-carboxybutanoyl-[Arg34]GLP-1-(7-37) peptide, N-ε$^{26}$-(19-carboxynonadecanoylamino)-4(S)-carboxybutanoyl-[Arg34]GLP-1-(7-37) peptide, N-ε$^{26}$-(21-carboxyheneicosanoylamino)-4(S)-carboxybutanoyl-[Arg34]GLP-1-(7-37) peptide, N-ε$^{26}$-[2-(2-[2-(2-[2-(2-[4-(20-carboxyeicosanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[20-carboxyeicosanoylamino]-4(S)-carboxybutanoylamino)ethoxy]ethoxy)acetyl][Gly8, Arg34]GLP-1-(7-37) peptide, N-ε$^{26}$-[2-(2-[2-(2-[2-(2-[4-(22-carboxydocosanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[22-carboxydocosanoylamino]-4(S)-carboxybutanoylamino)ethoxy]ethoxy)acetyl][Gly8, Arg34]GLP-1-(7-37) peptide, N-ε$^{26}$-(20-carboxyeicosanoylamino)-4(S)-carboxybutanoyl-[Gly8, Arg34]GLP-1-(7-37) peptide, N-ε$^{26}$-(22-carboxydocosanoylamino)-4(S)-carboxybutanoyl-[Gly8, Arg34]GLP-1-(7-37) peptide, N-ε$^{26}$-[2-(2-[2-(2-[2-(2-[4-(20-carboxyeicosanoylamino)-4(S)-carboxybutanoylamino]ethoxy)ethoxy]acetylamino)ethoxy]ethoxy)acetyl][Arg34]GLP-1-(7-37) peptide, N-ε$^{26}$-[2-(2-[2-(4-[20-carboxyeicosanoylamino]-4(S)-carboxybutanoylamino)ethoxy]ethoxy)acetyl][Arg34]GLP-1-(7-37) peptide, N-ε$^{26}$-[2-(2-[2-(2-[2-(2-[4-(22-carboxydocosanoylamino)-4(S)-carboxybutanoylamino]ethoxy)ethoxy]acetylamino)ethoxy]ethoxy)acetyl][Arg34]GLP-1-(7-37) peptide, N-ε$^{26}$-[2-(2-[2-(4-[22-carboxydocosanoylamino]-4(S)-carboxybutanoylamino)ethoxy]ethoxy)acetyl][Arg34]GLP-1-(7-37) peptide, N-ε$^{26}$-(20-carboxyeicosanoylamino)-4(S)-carboxybutanoyl-[Arg34]GLP-1-(7-37) peptide, and N-ε$^{26}$-(22-carboxydocosanoylamino)-4(S)-carboxybutanoyl-[Arg34]GLP-1-(7-37) peptide.

In some embodiments, the insulinotropic GLP-1 compound is selected from the group consisting of N-ε$^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide, N-ε$^{26}$-(19-carboxynonadecanoylamino)-4(S)-carboxybutanoyl-[Gly8, Arg34]GLP-1-(7-37) peptide, N-ε$^{26}$-(19-carboxynonadecanoylamino)-4(S)-carboxybutanoyl-[Arg34]GLP-1-(7-37) peptide, N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide, and N-ε$^{26}$-[2-(2-[2-(4-[21-carboxyheneicosanoylamino]-4(S)-carboxybutanoylamino)ethoxy]ethoxy)acetyl][Gly8, Arg34]GLP-1-(7-37) peptide; preferably, the insulinotropic GLP-1 compound is:

N-ε$^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide, or N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide.

The inventors have surprisingly found that the pharmaceutical composition or the combo formulation of an insulin derivative (e.g., an acylated insulin) and an insulinotropic GLP-1 compound disclosed herein does not impair the physical stability of the insulin derivative (e.g., the acylated insulin); instead, the combo formulation has a better physical stability than the mono formulation. The physical stability of the combo formulation of the present invention is beyond expectation compared to combo formulations of other long-acting insulin derivatives (e.g., insulin degludec and liraglutide). Furthermore, the combo formulation also allows for an increase in the chemical stability of the insulin derivative (e.g., the acylated insulin) compared to a mono formulation.

In some embodiments, the pharmaceutical composition further comprises a rapid-acting insulin.

In some embodiments, the rapid-acting insulin is one or more selected from Asp$^{B28}$ human insulin, Lys$^{B28}$Pro$^{B29}$ human insulin, Lys$^{B3}$Glu$^{B29}$ human insulin, human insulin and desB30 human insulin; preferably, the rapid-acting insulin is $Asp^{B28}$ human insulin, $Lys^{B28}Pro^{B29}$ human insulin, $Lys^{B3}Glu^{B29}$ human insulin, human insulin or desB30 human insulin.

The inventors have surprisingly found that a pharmaceutical composition comprising dual insulin components of the insulin derivative (e.g. acylated insulin) of the present invention and insulin aspart, after being administered, has a surprisingly increased hypoglycemic effect compared to a pharmaceutical composition comprising dual insulin components of insulin degludec and insulin aspart, and it can still achieve a better or comparable hypoglycemic effect when the dose ratio of the insulin derivative (e.g., the acylated insulin) disclosed herein to insulin aspart is far less than that of insulin degludec to insulin aspart.

In some embodiments, the molar ratio of the insulin derivative to the rapid-acting insulin is about 60:3 to about 0.5:3, preferably about 57:3 to about 1:3, preferably about 55:3 to about 1.2:3, preferably about 50:3 to about 1.5:3, preferably about 40:3 to about 1.5:3, preferably about 30:3 to about 1.5:3, preferably about 27:3 to about 1.5:3, preferably about 25:3 to about 1.5:3, preferably about 22:3 to about 1.5:3, preferably about 20:3 to about 1.5:3, preferably about 17:3 to about 1.5:3, preferably about 15:3 to about 1.5:3, preferably about 12:3 to about 1.5:3, preferably about 10:3 to about 1.5:3, preferably about 9:3 to about 1.5:3, preferably about 8:3 to about 1.5:3, preferably about 7:3 to about 1.5:3, preferably about 6.9:3 to about 1.5:3, preferably about 6.8:3 to about 1.5:3, preferably about 6.5:3 to about 1.5:3, preferably about 6.3:3 to about 1.5:3, preferably about 6:3 to about 1.5:3, preferably about 5.8:3 to about 1.5:3, preferably about 5.5:3 to about 1.5:3, preferably about 5.3:3 to about 1.5:3, preferably about 5:3 to about 1.5:3, preferably about 4.8:3 to about 1.5:3, preferably about 4.5:3 to about 1.5:3, preferably about 4.2:3 to about 1.5:3, preferably about 4:3 to about 1.5:3, preferably about 3.9:3 to about 1.5:3, preferably about 3.8:3 to about 1.5:3, preferably about 3.5:3 to about 1.5:3, preferably about 3.2:3 to about 1.5:3, preferably about 3:3 to about 1.5:3, preferably about 2.8:3 to about 1.5:3, preferably about 2.5:3 to about 1.5:3, preferably about 15:3 to about 2:3, preferably about 12:3 to about 2:3, preferably about 10:3 to about 2:3, preferably about 9:3 to about 2:3, preferably about 8:3 to about 2:3, preferably about 7:3 to about 2:3, preferably about 6.9:3 to about 2:3, preferably about 6.8:3 to about 2:3, preferably about 6.5:3 to about 2:3, preferably about 6.3:3 to about 2:3, preferably about 6:3 to about 2:3, preferably about 5.8:3 to about 2:3, preferably about 5.5:3 to about 2:3, preferably about 5.3:3 to about 2:3, preferably about 5:3 to about 2:3, preferably about 4.8:3 to about 2:3, preferably about 4.5:3 to about 2:3, preferably about 4.2:3 to about 2:3, preferably about 4:3 to about 2:3, preferably about 3.9:3 to about 2:3, preferably about 3.8:3 to about 2:3, preferably about 3.5:3 to about 2:3, preferably about 3.2:3 to about 2:3, preferably about 3:3 to about 2:3, preferably about 15:3 to about 2.4:3, preferably about 12:3 to about 2.4:3, preferably about 10:3 to about 2.4:3, preferably about 9:3 to about 2.4:3, preferably about 8:3 to about 2.4:3, preferably about 7:3 to about 2.4:3, preferably about 6.9:3 to about 2.4:3, preferably about 6.8:3 to about 2.4:3, preferably about 6.5:3 to about 2.4:3, preferably about 6.3:3 to about 2.4:3, preferably about 6:3 to about 2.4:3, preferably about 5.8:3 to about 2.4:3, preferably about 5.5:3 to about 2.4:3, preferably about 5.3:3 to about 2.4:3, preferably about 5:3 to about 2.4:3, preferably about 4.8:3 to about 2.4:3, preferably about 4.5:3 to about 2.4:3, preferably about 4.2:3 to about 2.4:3, preferably about 4:3 to about 2.4:3, preferably about 3.9:3 to about 2.4:3, preferably about 3.8:3 to about 2.4:3, preferably about 3.5:3 to about 2.4:3, preferably about 3.2:3 to about 2.4:3, preferably about 3:3 to about 2.4:3, more preferably about 1.5:3, more preferably about 2:3, more preferably about 2.5:3, more preferably about 2.75:3, or more preferably about 3:3.

In some embodiments, the insulin derivative is B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-7×OEG), desB30 human insulin; B29K(N(ε)-eicosanedioyl-γGlu-8×OEG), desB30 human insulin; B29K(N(ε)-docosanedioyl-γGlu-7×OEG), desB30 human insulin; B29K(N(ε)-docosanedioyl-γGlu-8×OEG), desB30 human insulin; B29K(N(ε)-eicosanedioyl-γGlu-9×OEG), desB30 human insulin; B29K(N(ε)-eicosanedioyl-γGlu-10×OEG), desB30 human insulin; B29K(N(ε)-docosanedioyl-γGlu-9×OEG), desB30 human insulin; B29K(N(ε)-docosanedioyl-γGlu-10×OEG), desB30 human insulin; B29K(N(ε)-eicosanedioyl-γGlu-11×OEG), desB30 human insulin; B29K(N(ε)-eicosanedioyl-γGlu-12×OEG), desB30 human insulin; or B29K(N(ε)-docosanedioyl-γGlu-12×OEG), desB30 human insulin.

In some embodiments, the pharmaceutical composition comprises about 0.09-0.36 mM insulin derivative, about 0.18 mM $Asp^{B28}$ human insulin, about 0.85% to about 2.0% (w/w) glycerol, about 15-70 mM phenol, about 8-14 moles of zinc ions/6 moles of the insulin derivative, about 10-120 mM sodium chloride and about 0-15 mM m-cresol, and has a pH value of about 7.0-8.2, wherein the insulin derivative is B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-8×OEG), desB30 human insulin; B29K(N(ε)-docosanedioyl-γGlu-8×OEG), desB30 human insulin; A14E, B16H, B25H, B29K(N(ε)-eicosanedioyl-γGlu-6×OEG), desB30 human insulin; A14E, B16H, B25H, B29K(N(ε)-docosanedioyl-γGlu-6×OEG), desB30 human insulin; B29K(N(ε)-eicosanedioyl-γGlu-12×OEG), desB30 human insulin; or B29K(N(ε)-docosanedioyl-γGlu-12×OEG), desB30 human insulin.

In some embodiments, the pharmaceutical composition comprises about 0.165-0.18 mM insulin derivative, about 0.18 mM $Asp^{B28}$ human insulin, about 1.5%-1.7% (w/w) glycerol, about 20-30 mM phenol, about 9-12 moles of zinc ions/6 moles of the insulin derivative, about 20-75 mM sodium chloride and about 10-15 mM m-cresol, and has a pH value of about 7.0-8.2, wherein the insulin derivative is B29K(N(ε)-eicosanedioyl-γGlu-5×OEG), desB30 human insulin; B29K(N(ε)-eicosanedioyl-γGlu-6×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-eicosanedioyl-γGlu-8×OEG), desB30 human insulin; or B29K(N(ε)-docosanedioyl-γGlu-8×OEG), desB30 human insulin.

In another aspect of the present invention, provided is the insulin derivative or the pharmaceutical composition disclosed herein for use as a medicament.

In another aspect, the present invention provides the insulin derivative or the pharmaceutical composition disclosed herein for use as a medicament for treating or preventing diabetes, hyperglycemia, and/or impaired glucose tolerance.

In another aspect, the present invention provides the insulin derivative or the pharmaceutical composition disclosed herein for use in treating or preventing diabetes, hyperglycemia, and/or impaired glucose tolerance.

In another aspect, the present invention provides the use of the insulin derivative or the use of the pharmaceutical composition disclosed herein in preparing a medicament; preferably, the medicament is used for treating or preventing diabetes, hyperglycemia, and/or impaired glucose tolerance.

In some embodiments, the medicament is used for treating diabetes; the insulin derivative is administered to the same patient every other day or at a lower frequency, and on average, the insulin derivative is not administered to the same patient at a higher frequency during a period of at least 1 month, 6 months or 1 year.

In some embodiments, the medicament is used for treating diabetes; the insulin derivative is administered twice a week or at a lower frequency, and on average, the acylated insulin is not administered to the same patient at a higher frequency during a period of at least 1 month, 6 months or 1 year.

In another aspect, the present invention provides a method for treating or preventing diabetes, hyperglycemia, and/or impaired glucose tolerance, which includes administering a therapeutically effective amount of the insulin derivative or the pharmaceutical composition of the present invention described above.

The inventors have surprisingly found that the insulin derivative (e.g., the acylated insulin) of the present invention has a long pharmacokinetic (hereinafter also referred to as PK) profile, which makes possible a subcutaneous treatment of diabetic patients at twice a week, once a week or at a lower frequency.

In another aspect, the present invention provides a method for increasing capability of an insulin derivative to bind to an insulin receptor in the presence of albumin, which comprises: linking an albumin binding residue to a natural insulin or an insulin analogue via a linker Lin to obtain the insulin derivative, wherein the linker Lin is a hydrophilic linker having at least 10, preferably at least 15, preferably at least 20, preferably at least 25, preferably at least 30, preferably at least 36, preferably at least 40, preferably 15-200, preferably 20-200, preferably 25-180, preferably 30-180, preferably 42-180, preferably 54-180, preferably 59-180, preferably 61-180, preferably 66-180 or preferably 72-120 carbon atoms; the albumin binding residue contains 20-40 carbon atoms; preferably, the albumin binding residue comprises a linear or branched lipophilic group containing 20-40 carbon atoms; preferably, the albumin binding residue is a fatty acid or a fatty diacid containing 20-26 carbon atoms (more preferably a fatty acid or a fatty diacid containing 20-24 carbon atoms), wherein formally, a hydroxyl group has been removed from the carboxyl group in the fatty acid or one of the carboxyl groups in the fatty diacid; or

- modifying a natural insulin or insulin analogue with formula (A) or formula (A') to obtain the insulin derivative, III-$(II)_m$-$(I)_n$- (A), wherein,
- m is 0, 1, 2, 3, 4, 5, 6, 7, 8, 9 or 10, and n is an integer equal to or greater than 5, preferably an integer from 5 to 30;
- I is a neutral and alkylene glycol-containing amino acid residue;
- II is an acidic amino acid residue;
- III is an albumin binding residue comprising a linear or branched lipophilic group containing 20-40 carbon atoms; preferably, III is a fatty acid or a fatty diacid containing 20-26 carbon atoms (more preferably a fatty acid or a fatty diacid containing 20-24 carbon atoms), wherein formally, a hydroxyl group has been removed from the carboxyl group in the fatty acid and one of the carboxyl groups in the fatty diacid;
- III, II and I are linked by amide bonds; and
- the order of II and I presented in the formula (A) can be interchanged independently;

(A') is III-$(II)_m$-$(I')_{n'}$- (A'), wherein,

- m is 0, 1, 2, 3, 4, 5, 6, 7, 8, 9 or 10, and n' is an integer;
- I' is a neutral and alkylene glycol-containing amino acid residue;
- II is an acidic amino acid residue;
- III is an albumin binding residue comprising a linear or branched lipophilic group containing 20-40 carbon atoms; preferably, III is a fatty acid or a fatty diacid containing 20-26 carbon atoms (more preferably a fatty acid or a fatty diacid containing 20-24 carbon atoms), wherein formally, a hydroxyl group has been removed from the carboxyl group in the fatty acid and one of the carboxyl groups in the fatty diacid;
- III, II and I' are linked by amide bonds;
- the order of II and I' presented in the formula (A') can be interchanged independently; and the total number of carbon atoms of $(I')_n$ is 15-200, preferably 20-200, preferably 25-180, preferably 30-180, preferably 42-180, preferably 54-180, preferably 59-180, preferably 61-180, preferably 66-180 or preferably 72-120.

In another aspect, the present invention provides a method for increasing potency of an insulin derivative, which includes:

- linking an albumin binding residue to a natural insulin or an insulin analogue via a linker Lin to obtain the insulin derivative, wherein the linker Lin is a hydrophilic linker containing at least 10, preferably at least 15, preferably at least 20, preferably at least 25, preferably at least 30, preferably at least 36, preferably at least 40, preferably 15-200, preferably 20-200, preferably 25-180, preferably 30-180, preferably 42-180, preferably 54-180, preferably 59-180, preferably 61-180, preferably 66-180 or preferably 72-120 carbon atoms; the albumin binding residue contains 20-40 carbon atoms; preferably, the albumin binding residue contains a linear or branched lipophilic group containing 20-40 carbon atoms; preferably, the albumin binding residue is a fatty acid or a fatty diacid containing 20-26 carbon atoms (more preferably a fatty acid or a fatty diacid containing 20-24 carbon atoms), wherein formally, a hydroxyl group has been removed from the carboxyl groups in the fatty acid or one of the carboxyl groups in the fatty diacid; or
- modifying a natural insulin or an insulin analogue with formula (A) or formula (A') to obtain the insulin derivative, III-$(II)_m$-$(I)_n$- (A), wherein,
- m is 0, 1, 2, 3, 4, 5, 6, 7, 8, 9 or 10, and n is an integer equal to or greater than 5, preferably an integer from 5 to 30;
- I is a neutral and alkylene glycol-containing amino acid residue;
- II is an acidic amino acid residue;
- III is an albumin binding residue comprising a linear or branched lipophilic group containing 20-40 carbon atoms; preferably, III is a fatty acid or a fatty diacid containing 20-26 carbon atoms (more preferably a fatty acid or a fatty diacid containing 20-24 carbon atoms), wherein formally, a hydroxyl group has been removed from the carboxyl group in the fatty acid and one of the carboxyl groups in the fatty diacid;

III, II and I are linked by amide bonds; and the order of II and I presented in the formula (A) can be interchanged independently; or III-(II)$_m$-(I')$_{n'}$- (A'), wherein, m is 0, 1, 2, 3, 4, 5, 6, 7, 8, 9 or 10, and n' is an integer equal to or greater than 5;

I' is a neutral and alkylene glycol-containing amino acid residue;

II is an acidic amino acid residue;

III is an albumin binding residue comprising a linear or branched lipophilic group containing 20-40 carbon atoms; preferably, III is a fatty acid or a fatty diacid containing 20-26 carbon atoms (more preferably a fatty acid or a fatty diacid containing 20-24 carbon atoms), wherein formally, a hydroxyl group has been removed from the carboxyl group in the fatty acid and one of the carboxyl groups in the fatty diacid;

III, II and I' are linked by amide bonds;

the order of II and I' presented in the formula (A') can be interchanged independently; and the total number of carbon atoms of (I')$_n$ is 15-200, preferably 20-200, preferably 25-180, preferably 30-180, preferably 42-180, preferably 54-180, preferably 59-180, preferably 61-180, preferably 66-180 or preferably 72-120.

In some embodiments, the natural insulin or the insulin analogue comprises at least one lysine residue, and the linker Lin, the formula (A) or the formula (A') is linked to an amino group of the lysine residue or an N-terminal amino acid residue of the insulin parent.

In some embodiments, n is an integer from 5 to 18; preferably, n is an integer from 5 to 15; preferably, n is 5, 6, 7, 8, 9, 10, 11, 12, 13 or 14; preferably, n is 5, 6, 7, 8, 9, 10, 11 or 12; preferably, n is 5, 6, 7, 8, 9 or 10; preferably, n is 5, 6, 7, 8 or 9; preferably, n is 5, 6, 7 or 8; and/or m is an integer from 1 to 6; preferably, m is 1, 2, 3 or 4; preferably, m is 1 or 2; preferably, m is 1; and/or III is a fatty diacid containing 20-26 (preferably 20-23) carbon atoms, and preferably III is a fatty diacid containing 20, 21 or 22 carbon atoms, wherein formally, a hydroxyl group has been removed from one of the carboxyl groups in the fatty diacid; and/or the insulin parent comprises one lysine residue.

In some embodiments, I is: —HN—$(CH_2)_2$—O—$(CH_2)_2$—O—$CH_2$—CO—, —HN—$(CH_2)_2$—O—$(CH_2)_2$—O—$(CH_2)_2$—O—$(CH_2)_2$—O—$(CH_2)_2$—CO—, —HN—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—CO—, —HN—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—O—$(CH_2)_2$—CO—, —HN—$(CH_2)_3$—O—$(CH_2)_4$—O—$(CH_2)_3$—NH—CO—, —HN—$(CH_2)_3$—O—$(CH_2)_4$—O—$(CH_2)_3$—NH—CO—$CH_2$—O—$CH_2$—CO—, —HN—$(CH_2)_3$—O—$(CH_2)_4$—O—$(CH_2)_3$—NH—CO—$(CH_2)_2$—CO—, —HN—$(CH_2)_2$—O—$(CH_2)_2$O—$CH_2$—CO—$CH_2$—O—$CH_2$—CO—, —HN—$(CH_2)_3$—O—$(CH_2)_2$—O—$(CH_2)_2$—O—$(CH_2)_3$—NH—CO—$(CH_2)_2$—CO—, —HN—$(CH_2)_3$—O—$(CH_2)_2$—O—$(CH_2)_2$—O—$(CH_2)_3$—NH—CO—$CH_2$—O—$CH_2$—CO—, —HN—$(CH_2)_2$—O—$(CH_2)_2$—O—$(CH_2)_2$—NH—CO—$(CH_2)_2$—CO—, —HN—$(CH_2)_2$—O—$(CH_2)_2$—O—$(CH_2)_2$—NH—CO—$CH_2$—O—$CH_2$—CO—, —HN—$(CH_2)_3$—O—$(CH_2)_2$—O—$(CH_2)_2$—O—$(CH_2)_3$—NH—CO—$CH_2$—O—$CH_2$—CO—, —HN—$(CH_2)_3$—O—$(CH_2)_3$O—$CH_2$—CO—, or —HN—$(CH_2)_4$—O—$(CH_2)_4$O—$CH_2$—CO—; preferably, I is —HN—$(CH_2)_2$—O—$(CH_2)_2$O—$CH_2$—CO—; or I' is —HN—$(CH_2$—$CH_2$—$O)_{10}$—$CH_2$—CO—, —HN—$(CH_2$—$CH_2$—$O)_{11}$—$CH_2$—CO—, —HN—$(CH_2$—$CH_2$—$O)_{12}$—$CH_2$—CO—, —HN—$(CH_2$—$CH_2$—$CH_2$—$O)_8$—$CH_2$—CO—, —HN—$(CH_2$—$CH_2$—$O)_2$O—$CH_2$—CO—, —HN—$(CH_2$—$CH_2$—$O)_{22}$—$CH_2$—CO—, —HN—$(CH_2$—$CH_2$—$O)_{24}$—$CH_2$—CO—, or —HN—$(CH_2$—$CH_2$—$CH_2$—$O)_{15}$—$CH_2$—CO—; and/or II is an amino acid residue selected from the group consisting of γGlu, αGlu, βAsp, αAsp, γ-D-Glu, α-D-Glu, β-D-Asp and α-D-Asp; preferably, II is selected from γGlu and βAsp; and/or III is HOOC—$(CH_2)_{18}$—CO—, HOOC—$(CH_2)_{19}$—CO—, HOOC—$(CH_2)_{20}$—CO—, HOOC—$(CH_2)_{21}$—CO—, HOOC—$(CH_2)_{22}$—CO— or HOOC—$(CH_2)_{24}$—CO—; preferably, III is HOOC—$(CH_2)_{18}$—CO—, HOOC—$(CH_2)_{20}$—CO— or HOOC—$(CH_2)_{22}$—CO—.

In some embodiments, the formula (A) is linked to an amino group of the lysine residue or an N-terminal amino acid residue of the natural insulin or insulin analogue via the C-terminal of I, or the formula (A') is linked to the amino group of the lysine residue or the N-terminal amino acid residue of the natural insulin or insulin analogue via the C-terminal of I'.

In some embodiments, the formula (A) or the formula (A') is linked to an F amino group of the lysine residue of the insulin parent.

In some embodiments, the lysine residue of the natural insulin or insulin analogue is at position B29.

The natural insulin or insulin analogue is selected from the group consisting of desB30 human insulin; A14E, B16H, B25H, desB30 human insulin; A14E, B16E, B25H, desB30 human insulin; human insulin; A21G human insulin; A21G, desB30 human insulin; and B28D human insulin; preferably, the insulin parent is desB30 human insulin or A14E, B16H, B25H, desB30 human insulin.

DETAILED DESCRIPTION

Definitions

Figure 1A:
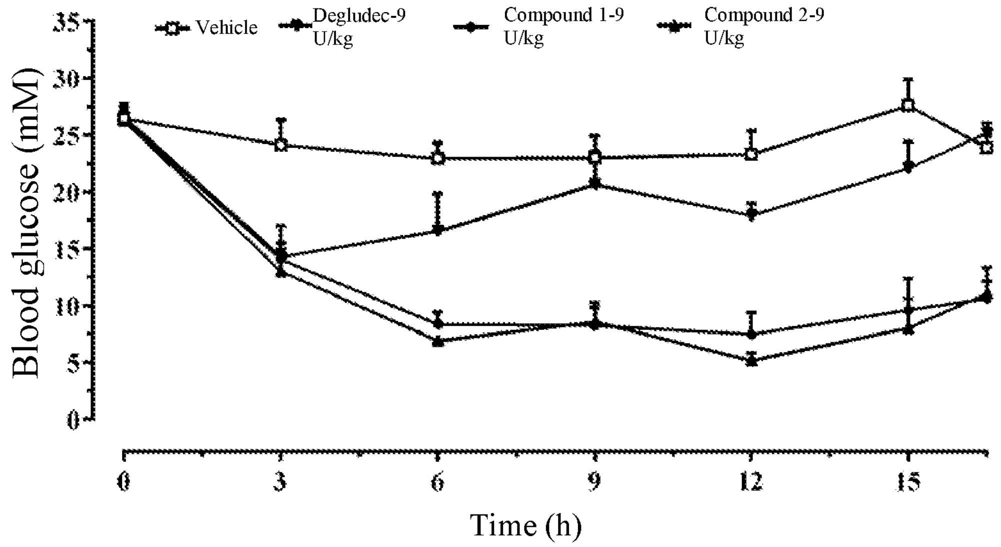
FIG. 1*a* shows the hypoglycemic effect of the compounds of Examples 1 and 2 in the present invention, insulin degludec and vehicle on db/db mice.

Herein, the term "insulin" encompasses natural insulins, such as human insulin, and insulin analogues and insulin derivatives thereof.

The term "insulin analogue" covers a polypeptide having a molecular structure which may be formally derived from the structure of a natural insulin (e.g., human insulin) by deletion and/or substitution (replacement) of one or more amino acid residues presented in the natural insulin and/or by addition of one or more amino acid residues. The amino acid residues for addition and/or substitution may be encodable amino acid residues, or other natural amino acid residues, or purely synthetic amino acid residues. Preferably, the amino acid residues for addition and/or substitution are encodable amino acid residues.

Herein, the term "insulin derivative" refers to a natural insulin or insulin analogue which has been chemically modified, and the modification may be, for example, introducing a side chain at one or more positions of the insulin backbone, oxidizing or reducing groups of amino acid residues on the insulin, converting a free carboxyl group into an ester group, or acylating a free amino group or a hydroxyl group. The acylated insulins of the present invention are insulin derivatives.

The term "insulin parent" refers to an insulin moiety of an insulin derivative or an acylated insulin (also referred to herein as parent insulin), and, for example, refers to a moiety of an insulin derivative or an acylated insulin without a linking side chain or an added acyl group in the present invention. The insulin parent may be a natural insulin, such as human insulin or porcine insulin.

In another aspect, the parent insulin may be an insulin analogue.

Herein, the term "amino acid residue" encompasses amino acids from which a hydrogen atom has been removed from an amino group and/or a hydroxyl group has been removed from a carboxyl group and/or a hydrogen atom has been removed from a mercapto group. Imprecisely, an amino acid residue may be referred to as an amino acid.

Unless otherwise stated, all amino acids referred to herein are L-amino acids.

The term "albumin binding residue" refers to a residue that is capable of non-covalently binding to human serum albumin. The albumin binding residues linked to an insulin typically have a binding affinity for human serum albumin of less than, for example, about 10 μM or even less than about 1 μM. Albumin binding properties can be measured by surface plasmon resonance as described in: J. Biol. Chem. 277(38), 35035-35042, (2002).

Herein, "hydrophilic linker" refers to a linker that comprises at least 6 non-hydrogen atoms, 30-50% of which are N or O, and separates the insulin parent from the albumin binding residue.

"Lipophicity" refers to the ability of a group to dissolve in fats, oils, lipids, and lipophilic non-polar solvents (such as hexane or toluene). Lipophilic groups, including but not limited to, for example, fats, fatty acids or fatty diacids, typically have a "lipid tail", and the lipid tail present in these lipophilic groups can be saturated and unsaturated, depending on whether the lipid tail comprises a double bond. The lipid tail may also comprise different lengths, such as a tail having 7-12 carbons (e.g., $C_{7-12}$ alkyl or $C_{7-12}$ alkenyl), a tail having 13-22 carbons (e.g., $C_{13-22}$ alkyl or $C_{13-22}$ alkenyl), or a tail having 23-30 carbons (e.g., C23-30 alkyl or C23-30 alkenyl).

Herein, the term "alkylene glycol" comprises oligo- and poly-alkylene glycol moieties and monoalkylene glycol moieties. Monoalkylene glycols and polyalkylene glycols include, for example, chains based on monoethylene and polyethylene glycols, monopropylene and polypropylene glycols, and monotetramethylene and polytetramethylene glycols, i.e., chains based on the repeating unit $—CH_2CH_2O—$, $—CH_2CH_2CH_2O—$ or $—CH_2CH_2CH_2CH_2O—$. The alkylene glycol moiety can be monodisperse (with well-defined length/molecular weight) and polydisperse (with less well-defined length/average molecular weight). The monoalkylene glycol moiety includes $—OCH_2CH_2O—$, $—OCH_2CH_2CH_2O—$ or $—OCH_2CH_2CH_2CH_2O—$ comprising different groups at each end.

The term "fatty acid" includes linear or branched fatty carboxylic acids having at least two carbon atoms and being saturated or unsaturated. Non-limiting examples of fatty acids are, for example, myristic acid, palmitic acid, stearic acid, and eicosanoic acid.

Herein, the term "fatty diacid" includes linear or branched fatty dicarboxylic acids having at least two carbon atoms and being saturated or unsaturated. Non-limiting examples of fatty diacids are hexanedioic acid, octanedioic acid, decanedioic acid, dodecanedioic acid, tetradecanedioic acid, hexadecanedioic acid, heptadecanedioic acid, octadecanedioic acid, eicosanedioic acid, docosanedioic acid and tetracosanedioic acid.

As used herein, rapid-acting insulins include rapid-acting natural insulins, insulin analogues and insulin derivatives. Rapid-acting insulin typically begins to act within, for example, 1 to 20 minutes, peaks after about one hour, and continues to act for three to five hours.

The term "basal insulin" refers to an insulin having a longer duration of action than conventional or normal human insulin.

Herein, the term "chemical stability" means that the insulin derivatives disclosed in the present invention are chemically sufficiently stable in a desired formulation. That is, chemical degradation products are formed in just an amount that does not impair the shelf life of the final drug product.

Chemical degradation products include deamidation products, products from the formation of isoaspartic ester, the formation of dimer, the racemization, the dehydration process and the like.

Chemical stability can be determined by HPLC analysis of aged samples or formulations.

As used herein, "binding capacity to an insulin receptor" refers to the interaction between an insulin and an insulin receptor, the magnitude or strength of which can be measured by, for example, surface plasmon resonance (SPR). For example, in SPR measurements, when a solution containing insulin flows over a chip coated with an insulin receptor, the resulting interaction between the insulin and the insulin receptor causes a change in the SPR deflection angle, which is usually expressed as a relative response value, and a greater relative response value generally indicates a higher binding capacity to the insulin receptor.

High physical stability means that the fibrillation tendency is less than 50% of that of human insulin. Fibrillation can be described by the lag time before fibrillation starts to form under given conditions.

Polypeptides having affinity for an insulin receptor and an IGF-1 receptor are polypeptides that are capable of interacting with the insulin receptor and the human IGF-1 receptor in a suitable binding assay. Such receptor assays are well known in the art.

As used herein, "drug effect" or "potency" refers to the ability of a drug or an active compound to result in a certain function or effect (e.g., lowering blood glucose). For example, compared with insulin degludec or other existing insulin derivatives, administration of the same dose of an insulin derivative of the present invention will result in a better blood glucose lowering effect or function.

The term "diabetes" includes type 1 diabetes, type 2 diabetes, gestational diabetes (during pregnancy) and other conditions that cause hyperglycemia. The term is used for metabolic disorders in which the pancreas produces insufficient amount of insulin or in which cells of the body fail to respond appropriately to insulin, thereby preventing the cells from taking up glucose.

As a result, glucose accumulates in the blood.

Type 1 diabetes, also known as insulin-dependent diabetes mellitus (IDDM) and juvenile onset diabetes, is caused by β-cell destruction and often results in absolute insulin deficiency. Type 2 diabetes, also known as non-insulin dependent diabetes mellitus (NIDDM) and adult onset diabetes, is associated with major insulin resistance and thus major defects in insulin secretion featuring relative insulin deficiency and/or insulin resistance.

As used herein, the term "GLP-1 analogue" or "analogue of GLP-1" refers to a peptide or compound that is a variant of human glucagon-like peptide-1 (GLP-1(7-37)), wherein one or more amino acid residues of GLP-1(7-37) are replaced, and/or one or more amino acid residues are deleted, and/or one or more amino acid residues are added. Specifically, the sequence of GLP-1(7-37) is shown in SEQ ID NO: 15 in the sequence listing. A peptide having the sequence shown in SEQ ID NO: 15 may also be referred to as "natural" GLP-1 or "natural" GLP-1(7-37).

In the sequence listing, the first amino acid residue (His) in SEQ ID NO: 15 is numbered 1. However, in the following, according to established practice in the art, the histidine residue is numbered 7 and the following amino acid residues are numbered sequentially, ending with glycine as No. 37. Thus, in general, based on the numbering for amino acid residues or positions, the GLP-1(7-37) sequence referred to herein is a sequence starting with His at position 7 and ending with Gly at position 37.

[Gly8, Arg34]GLP-1-(7-37) peptide is a GLP-1 analogue having Gly and Arg at positions corresponding to position 8 and position 34, respectively, of GLP-1(7-37) (SEQ ID NO: 15).

[Arg34]GLP-1-(7-37) peptide is a GLP-1 analogue having Arg at a position corresponding to position 34 of GLP-1(7-37) (SEQ ID NO: 15). Specifically, the amino acid sequences of [Gly8, Arg34]GLP-1-(7-37) peptide and [Arg34]GLP-1-(7-37) peptide are shown in SEQ ID NO: 16 and SEQ ID NO: 17 in the sequence listing, respectively.

In the case of a GLP-1 peptide or an analogue thereof, the term "derivative" as used herein refers to a chemically modified GLP-1 peptide or analogue, wherein one or more substituents have been covalently linked to the peptide. Substituents may also be referred to as side chains.

As used herein, the naming of insulin or GLP-1 compounds follows the following principle: the names are given according to mutations and modifications (e.g., acylation) relative to human insulin, or mutations and modifications (e.g., acylation) of natural GLP-1(7-37). The naming of the acyl moieties is based on the IUPAC nomenclature and, in other cases, the peptide nomenclature. For example, the following acyl moiety:

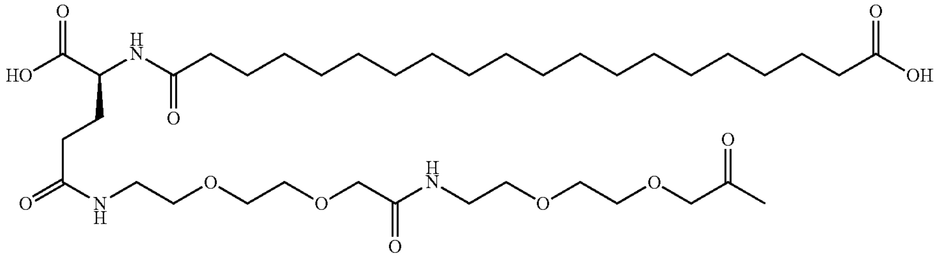 [SMILES: CC(=O)COCCOCCNC(=O)COCCOCCNC(=O)CC[C@H](NC(=O)CCCCCCCCCCCCCCCCCCC(=O)O)C(=O)O]

can be named, for example, as "eicosanedioyl-γGlu-OEG-OEG", "eicosanedioyl-γGlu-2xOEG" or "eicosanedioyl-gGlu-2xOEG", or "19-carboxynonadecanoyl-γGlu-OEG-OEG", wherein OEG is the shorthand for the group —NH$(CH_2)_2O(CH_2)_2OCH_2CO$— (i.e., 2-[2-(2-aminoethoxy)ethoxy]acetyl) and γGlu (or gGlu) is a shorthand for the amino acid 7-glutamic acid in the L configuration. Alternatively, the acyl moieties may be named according to IUPAC nomenclature (OpenEye, IUPAC format). According to this nomenclature, the above acyl moiety of the present invention is referred to as the following name: [2-(2-[2-(2-[2-(2-[4-(19-carboxynonadecanoylamino)-4(S)-carboxybutanoylamino]ethoxy)ethoxy]acetylamino)ethoxy]ethoxy)acetyl], or [2-[2-[2-[2-[2-[2-[(4S)-4-carboxy-4-(19-carboxynonadecanoylamino)butanoyl]-amino]-ethoxy]-ethoxy]acetyl]amino]ethoxy]ethoxy]acetyl].

For example, the insulin of Comparative Example 2 of the present invention (having the sequence/structure given below) is referred to as "B29K(N(ε)-eicosanedioyl-γGlu-2×OEG), desB30 human insulin", "B29K ($N^ε$-eicosanedioyl-γGlu-2×OEG), desB30 human insulin", or "B29K($N^ε$-eicosanedioyl-gGlu-2×OEG), desB30 human insulin", which indicates that the amino acid K at position B29 in human insulin has been modified by acylation with the residue eicosanedioyl-gGlu-2×OEG on the ε nitrogen (referred to as $N^ε$ or (N(ε)) of the lysine residue at position B29, and that the amino acid T at position B30 in human insulin has been deleted. For another example, the insulin of Comparative Example 5 (having the sequence/structure given below) is referred to as "A14E, B16H, B25H, B29K($N^ε$-eicosanedioyl-gGlu-2×OEG), desB30 human insulin" or "A14E, B16H, B25H, B29K(N(s)-eicosanedioyl-γGlu-2×OEG), desB30 human insulin", which indicates that amino acid Y at position A14 in human insulin has been mutated to E, amino acid Y at position B16 in human insulin has been mutated to H, amino acid F at position B25 in human insulin has been mutated to H, amino acid K at position B29 in human insulin has been modified by acylation with the residue eicosanedioyl-gGlu-2×OEG on the E nitrogen (referred to as $N^E$) of the lysine residue at position B29, and amino acid T at position B30 in human insulin has been deleted.

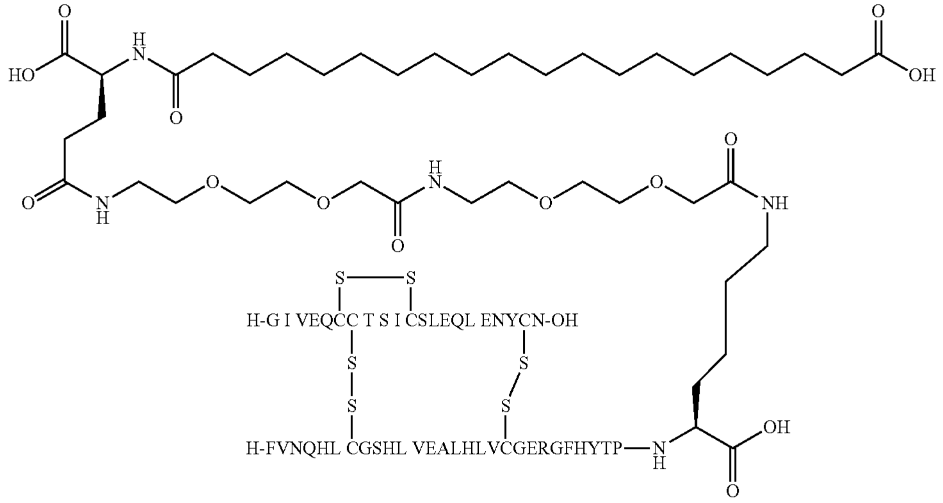

As used herein, "n×PEG" refers to the group —NH$(CH_2CH_2O)_nCH_2CO$—, where n is an integer. For example, "12×PEG" refers to the group —NH$(CH_2CH_2O)_{12}CH_2CO$—.

Insulin is a polypeptide hormone secreted by 3 cells in the pancreas and is composed of two polypeptide chains, namely A chain and B chain, linked by two inter-chain disulfide bonds. In addition, the A chain is characterized by having an intra-chain disulfide bond.

There are three main methods for preparing human insulin in microorganisms. Two of those methods involve *E. coli*, one by expressing fusion proteins in the cytoplasm (Frank et al. (1981) in Peptides: Proceedings of the 7th American Peptide Chemistry Symposium (Rich & Gross, eds.), Pierce Chemical Co., Rockford, III, pp. 729-739), and the other by enabling the secretion of a signal peptide into the periplasmic space (Chan et al. (1981) PNAS 78:5401-5404). The third method involves enabling the secretion of an insulin precursor into the medium by means of *Saccharomyces cerevisiae* (Thim et al. (1986) PNAS 83:6766-6770). A number of methods for the expression of insulin precursors in *E. coli* or *Saccharomyces cerevisiae* have been disclosed in the prior art. See, e.g., U.S. Pat. No. 5,962,267, WO95/16708, EP0055945, EP0163529, EP0347845 and EP0741188.

Construction of a vector, expression, processing and purification of an insulin analogue can be carried out using techniques well known to those skilled in the art. For example, the insulin analogue can be prepared by expressing a DNA sequence encoding the insulin analogue of interest in a suitable host cell by well-known techniques disclosed in U.S. Pat. No. 6,500,645. For example, insulin analogues can also be prepared by methods reported in the following paper: Glendorf T, Ssrensen A R, Nishimura E, Pettersson I, & Kjeldsen T: Importance of the Solvent-Exposed Residues of the Insulin B Chain α-Helix for Receptor Binding; *Biochemistry,* 2008, 47:4743-4751. In this paper, mutations are introduced into an insulin-encoding vector using overlap extension PCR. Insulin analogues are expressed in *Saccharomyces cerevisiae* strain MT663 as proinsulin-like fusion proteins with an Ala-Ala-Lys mini C-peptide. The single-chain precursors are enzymatically converted into two-chain desB30 analogues using *A. lyticus* endoprotease.

Isolated insulin analogues can be acylated at the desired position by acylation methods well known in the art, and examples of such insulin analogues are described in, for example, Chinese Patent Application Publication Nos. CN1029977C, CN1043719A and CN1148984A.

Nucleic acid sequences encoding polypeptides of the insulin analogues can be prepared synthetically by established standard methods, for example, by the method described in Beaucage et al. (1981) *Tetrahedron Letters* 22:1859-1869 or Matthes et al. (1984) *EMBO Journal* 3:801-805.

The term "excipient" broadly refers to any component other than the active therapeutic ingredient.

The excipient may be inert substances, inactive substances and/or non-pharmaceutically active substances.

The excipient may be used for various purposes, for example as carriers, vehicles, diluents, tablet aids, and/or for improving administration and/or absorption of the active substances, depending on the pharmaceutical composition. Examples of excipients include, but are not limited to, diluents, buffers, preservatives, tonicity modifiers (also known as tonicity agents or isotonic agents), chelating agents, surfactants, protease inhibitors, wetting agents, emulsifiers, antioxidants, fillers, metal ions, oily vehicles, proteins, and/or zwitterions, and stabilizers.

Pharmaceutical compositions of pharmaceutically active ingredients with various excipients are known in the art, see, e.g., Remington: The Science and Practice of Pharmacy (e.g., 19th edition (1995), and any later versions).

For the convenience of the patient, it is assumed that the time intervals (time delays) from the administration of the acylated insulin of the present invention to the next administration of the acylated insulin of the present invention are preferred by the patient to have the same length or approximately the same length in days. It can even be expected that a patient will prefer that administration of the acylated insulin occur once a week, i.e. on the same day of a week, e.g., every Sunday. This would be that the acylated insulin is administered, on average over a period of 1 month, 6 months or 1 year, every 6 days and not at a higher frequency. For some patients, it may be desirable to administer the acylated insulin, on average over a period of 1 month, 6 months or 1 year, every 5 days or approximately every 5 days and not at a higher frequency. For other patients, it may be desirable to administer the acylated insulin, on average over a period of 1 month, 6 months or 1 year, every 4 days or approximately every 4 days and not at a higher frequency. For other patients, it may be desirable to administer the acylated insulin, on average over a period of 1 month, 6 months or 1 year, every 3 days or approximately every 3 days and not at a higher frequency. Other patients may even find it advantageous to administer the acylated insulin twice a week on average over a period of 1 month, 6 months or 1 year, e.g., at intervals of about 3-4 days between administrations. For some patients, it may be desirable to administer the acylated insulin, on average over a period of 1 month, 6 months or 1 year, every 2 days or approximately every 2 days and not at a higher frequency. For other patients, it may be desirable to administer the acylated insulin, on average over a period of 1 month, 6 months or 1 year, every other day or approximately every other day and not at a higher frequency. For some patients, it may be desirable to administer the acylated insulin, on average over a period of 1 month, 6 months or 1 year, every 7 days or approximately every 7 days and not at a higher frequency. Other patients may even not administer the acylated insulin at intervals of exactly the same length of time (in days) weekly, monthly or yearly. On average over a period of 1 month, 6 months or 1 year, some patients may sometimes administer the acylated insulin at intervals of 5-7 days and not at a higher frequency. On average over a period of 1 month, 6 months or 1 year, other patients may sometimes administer the acylated insulin at intervals of 4-6 days and not at a higher frequency. On average over a period of 1 month, 6 months or 1 year, other patients may even sometimes administer the acylated insulin at intervals of 3-7 days and not at a higher frequency.

Diseases and conditions that are the primary targets of the present invention are diabetes (type 1 or type 2) or other conditions characterized by hyperglycemia, but mostly metabolic diseases and conditions in which the metabolic action of insulin has clinical relevance or benefits, such as pre-diabetes, impaired glucose tolerance, metabolic syndrome, obesity, cachexia, in vivo 3-cell damage/death, bulimia and inflammation. All of these types of conditions are known or believed to benefit from a stable metabolic state in a subject suffering from the disease or condition. In any event, any treatment regimen which comprises the administration of insulin can be varied by practicing the teachings of the present invention; that is, such therapy will comprise the administration of insulin with prolonged duration of action provided herein.

EXAMPLES

The following examples are provided by way of illustration but not limitation.

Abbreviations used herein are as follows:

- OEG: the amino acid residue —$NH(CH_2)_2O(CH_2)_2OCH_2CO$—;
- OSu: succinimidyl-1-yloxy-2,5-dioxo-pyrrolidin-1-yloxy;
- OtBu: oxy-tert-butyl;
- HCl: hydrogen chloride;
- γGlu or gGlu: γL-glutamoyl;
- NHS: N-hydroxysuccinimide;
- DCC: dicyclohexylcarbodiimide;
- AEEA: 2-(2-(2-aminoethoxy)ethoxy)acetic acid;
- OH: hydroxyl;
- $CH_3CN$: acetonitrile;
- Gly: glycine;
- Arg: arginine;
- TFA: trifluoroacetic acid;
- HbA1c: glycated hemoglobin;
- AUC: the area under the curve of the time-blood glucose curve;
- RU: response unit.

The following examples and general methods are directed to intermediate compounds and final products determined in the specification and synthetic schemes. The preparation of the compounds of the present invention is described in detail using the following examples, but the chemical reactions described are disclosed in terms of their general applicability to the preparation of the compounds of present the invention. Sometimes, the reaction may not be applicable to every compound within the scope of the present invention as described. Those skilled in the art will readily recognize compounds for which this will occur. In these cases, the reaction can be successfully carried out by conventional modifications known to those skilled in the art, that is, by suitable protection of interfering groups, by change into other conventional reagents, or by conventional modifications of the reaction conditions. In all preparation methods, all starting materials are known or can be readily prepared using known starting materials. All temperatures are given in degrees celsius and, unless otherwise explicitly stated; all parts and percentages are by weight when referring to yield, and all parts are by volume when referring to a solvent and an eluent.

Example 1

B29K(N(ε)-eicosanedioyl-γGlu-5×OEG), desB30 Human Insulin (Compound 1)

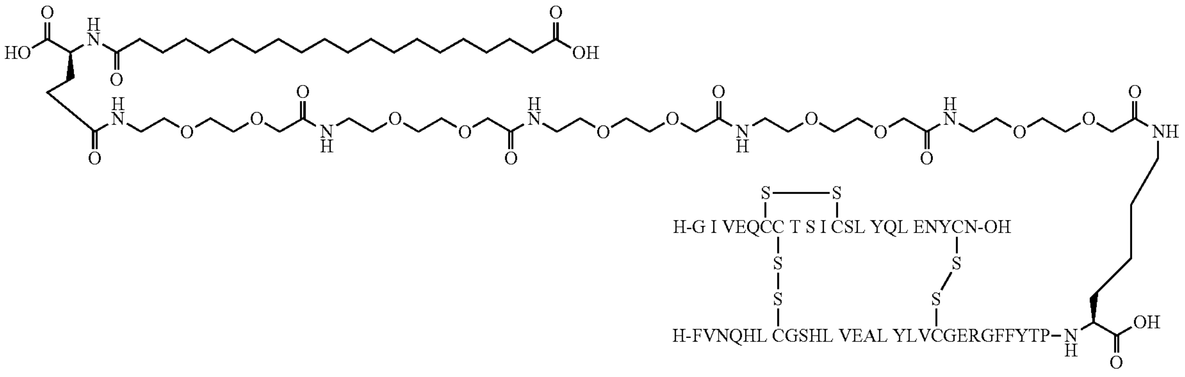

1. Synthesis of Des(B30) Human Insulin

Des(B30) human insulin was prepared according to the method described in Example 11 of Chinese patent CN1056618C.

2. Preparation of Insulin of Interest

DesB30 human insulin (5 g, 0.876 mmol) was dissolved in 100 mM aqueous $Na_2HPO_4$ solution (150 mL) and acetonitrile (100 mL) was added. The pH was adjusted to 10-12.5 with 1 N NaOH.

Tert-butyl eicosanedioyl-γGlu-(5×OEG-OSu)-OtBu (1.36 g, 0.964 mmol) was dissolved in acetonitrile (50 mL), and the solution was slowly added to the insulin solution. The pH was maintained at 10-12.5. After 120 min, the reaction mixture was added to water (150 mL), and the pH was adjusted to 5.0 with 1 N aqueous HCl solution. The precipitate was separated out by centrifugation and lyophilized. The crude product was added to a mixed solution of trifluoroacetic acid (60 mL) and dichloromethane (60 mL), and the mixture was stirred at room temperature for 30 min. The mixture was then concentrated to about 30 mL and poured into ice-cold n-heptane (300 mL), and the precipitated product was isolated by filtration and washed twice with n-heptane. The resulting precipitate was dried in vacuum and purified by ion exchange chromatography (Resource Q, 0.25%-1.25% ammonium acetate gradient in 42.5% ethanol, pH 7.5) and reverse phase chromatography (acetonitrile, water, TFA). The purified fractions were combined, adjusted to pH 5.2 with 1 N HCl, and separated to obtain the precipitate, which was lyophilized to obtain the title compound 1.

LC-MS (ESI): m/z=1377.53$[M+5H]^{5+}$

3. Preparation of Intermediate tert-butyl eicosanedioyl-γGlu-(5×OEG-OSu)-OtBu 3.1 Tert-butyl eicosanedioyl-OSu Eicosanedioic acid mono-tert-butyl ester (20 g, 50.17 mmol) and NHS (5.77 g, 50.17 mmol) were mixed in dichloromethane under nitrogen atmosphere, and triethylamine (13.95 mL) was added.

The resulting turbid mixture was stirred at room temperature, added with DCC (11.39 g, 55.19 mmol) and further stirred overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-OSu (24.12 g, yield 97%).

LC-MS (Sciex100API): m/z=496.36 $(M+1)^+$ 3.2 Tert-butyl eicosanedioyl-γGlu-OtBu Tert-butyl eicosanedioyl-OSu (24.12 g, 48.66 mmol) was dissolved in dichloromethane (250 mL), and the solution was stirred and added with H-Glu-OtBu (10.88 g, 53.53 mmol), triethylamine (12.49 mL) and water sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-OtBu (27.27 g, yield 96%).

LC-MS (Sciex100API): m/z=584.44 $(M+1)^+$ 3.3 Tert-butyl eicosanedioyl-γGlu-(OSu)-OtBu Tert-butyl eicosanedioyl-γGlu-OtBu (27.27 g, 46.71 mmol) was dissolved in dichloromethane (300 mL) under nitrogen atmosphere, and triethylamine (11.99 mL) was added. The mixture was stirred for 10 min, and NHS (5.38 g, 50.17 mmol) was added, followed by addition of DCC (10.60 g, 51.38 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure. Tert-butyl methyl ether was added, and the mixture was stirred for 30 min and filtered in vacuum. The filter cake was dried in vacuum overnight to obtain tert-butyl eicosanedioyl-γGlu-(OSu)-OtBu (25.76 g, yield 81%).

LC-MS (Sciex100API): m/z=681.46 $(M+1)^+$ 3.4 Tert-butyl eicosanedioyl-γGlu-(2×OEG-OH)-OtBu Tert-butyl eicosanedioyl-γGlu-(OSu)-OtBu (25.76 g, 37.83 mmol) was dissolved in dichloromethane (250 mL), and the solution was stirred and added with 2×AEEA (11.66 g, 37.83 mmol), triethylamine (9.71 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OH)-OtBu (30.75 g, yield 93%).

LC-MS (Sciex100API): m/z=874.59 $(M+1)^+$ 3.5 Tert-butyl eicosanedioyl-γGlu-(2×OEG-OSu)-OtBu Tert-butyl eicosanedioyl-γGlu-(2×OEG-OH)-OtBu (30.75 g, 35.18 mmol) was dissolved in dichloromethane (300 mL) under nitrogen atmosphere, and triethylamine (9.03 mL) was added. The mixture was stirred for 10 min, and NHS (4.05 g, 35.18 mmol) was added, followed by the addition of DCC (7.98 g, 38.70 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OSu)-OtBu (31.09 g, yield 91%).

LC-MS (Sciex100API): m/z=971.61 $(M+1)^+$

3.6 Tert-butyl eicosanedioyl-γGlu-(5×OEG-OH)-OtBu

Tert-butyl eicosanedioyl-γGlu-(2×OEG-OSu)-OtBu (31.09 g, 32.01 mmol) was dissolved in dichloromethane (350 mL), and the solution was stirred, and added with 3×AEEA (14.52 g, 32.01 mmol), triethylamine (8.90 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-(5×OEG-OH)-OtBu (38.99 g, yield 93%).

LC-MS (Sciex100API): m/z=1309.81 $(M+1)^+$

3.7 Tert-butyl eicosanedioyl-γGlu-(5×OEG-OSu)-OtBu

Tert-butyl eicosanedioyl-γGlu-(5×OEG-OH)-OtBu (38.99 g, 29.77 mmol) was dissolved in dichloromethane (400 mL) under nitrogen atmosphere, and triethylamine (8.28 mL) was added. The mixture was stirred for 10 min, and NHS (3.43 g, 29.77 mmol) was added, followed by the addition of DCC (6.76 g, 32.75 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(5×OEG-OSu)-OtBu (38.11 g, yield 91%).

LC-MS (Sciex100API): m/z=1406.83 $(M+1)^+$

Example 2

B29K(N(ε)-eicosanedioyl-γGlu-6×OEG), desB30 Human Insulin (Compound 2)

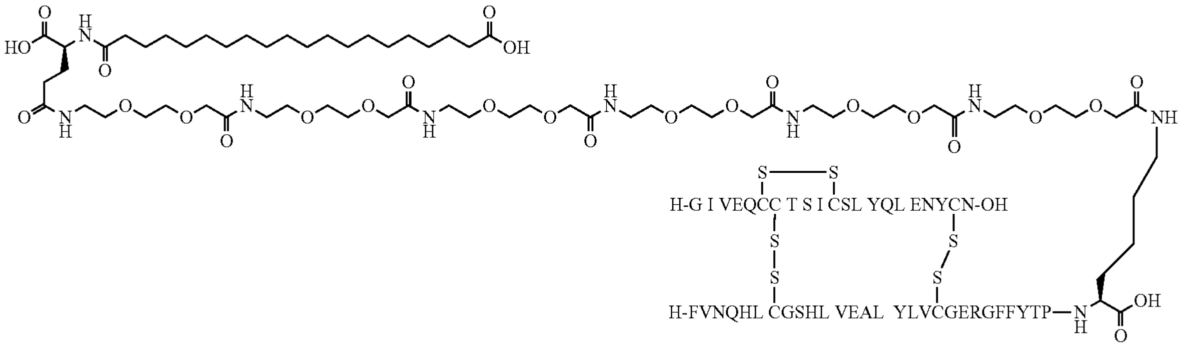

Compound 2 was prepared by procedures similar to those described in section 2 of Example 1.

LC-MS (ESI): m/z=1406.28$[M+5H]^{5+}$

The intermediate tert-butyl eicosanedioyl-γGlu-(6×OEG-OSu)-OtBu was prepared by procedures similar to those described in section 3 of Example 1.

LC-MS (Sciex100API): m/z=1551.90 $(M+1)^+$

Example 3

B29K(N(ε)-eicosanedioyl-γGlu-8×OEG1 desB30 Human Insulin (Compound 3)

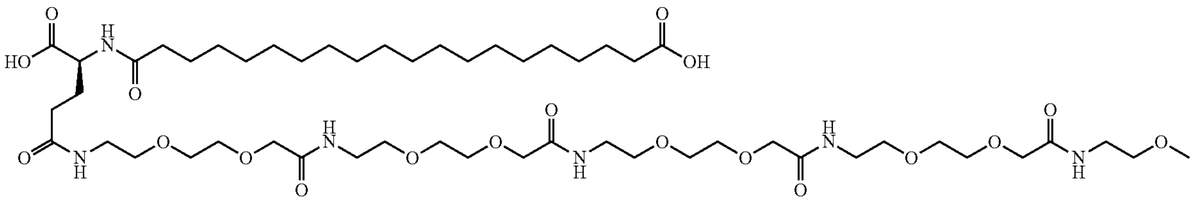

-continued

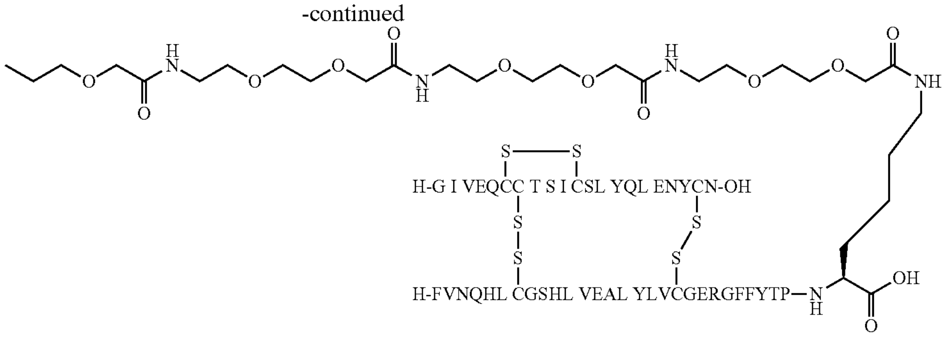

Compound 3 was prepared by procedures similar to those described in section 2 of Example 1.

LC-MS (ESI): m/z=1464.30[M+5H]$^{5+}$

The intermediate tert-butyl eicosanedioyl-γGlu-(8×OEG-OSu)-OtBu was prepared by procedures similar to those described in section 3 of Example 1.

LC-MS (Sciex100API): m/z=1814.02 (M+1)$^{+}$

Example 4

B29K(N(ε)-docosanedioyl-γGlu-6×OEG), desB30 Human Insulin (Compound 4)

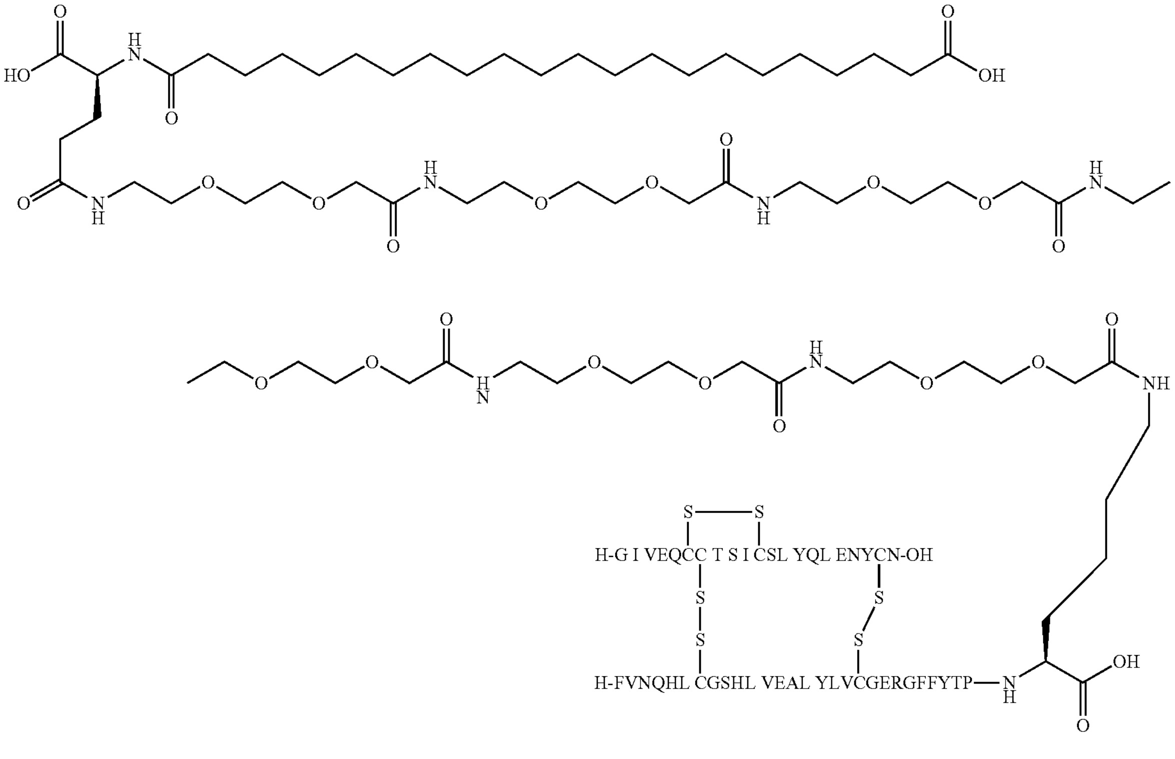

Compound 4 was prepared by procedures similar to those described in section 2 of Example 1.

LC-MS (ESI): m/z=1411.88[M+5H]$^{5+}$

The intermediate tert-butyl docosanedioyl-γGlu-(6×OEG-OSu)-OtBu was prepared by procedures similar to those described in section 3 of Example 1.

LC-MS (Sciex100API): m/z=1579.94 (M+1)$^{+}$

Example 5

B29K(N(ε)-docosanedioyl-γGlu-8×OEG), desB30 Human Insulin (Compound 5)

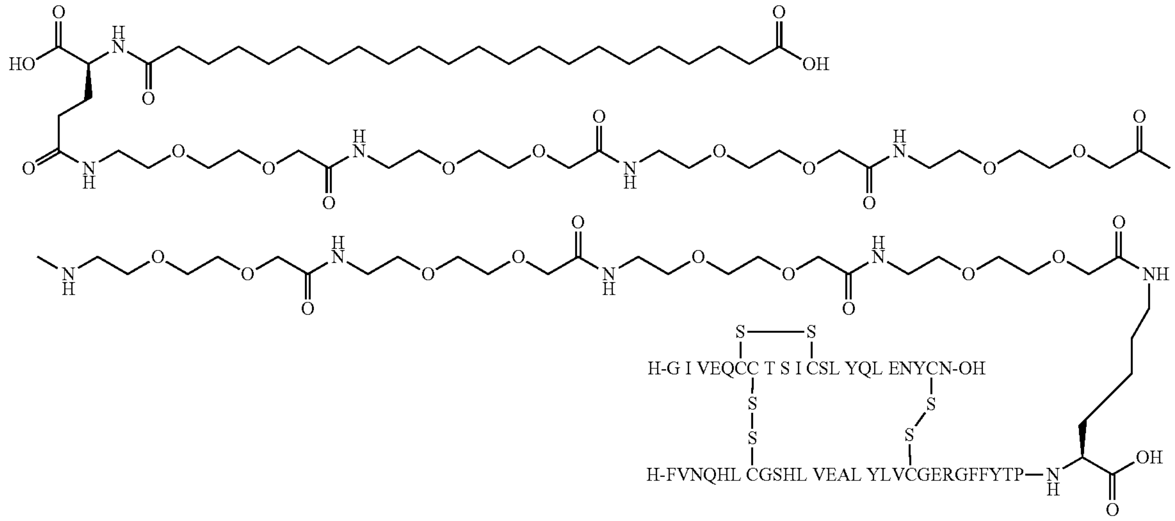

Compound 5 was prepared by procedures similar to those described in section 2 of Example 1.

LC-MS (ESI): m/z=1469.91[M+5H]$^{5+}$

The intermediate tert-butyl docosanedioyl-γGlu-(8×OEG-OSu)-OtBu was prepared by procedures similar to those described in section 3 of Example 1.

LC-MS (Sciex100API): m/z=1870.08 $(M+1)^+$

Comparative Example 1

B29K(N(ε)-hexadecanedioyl-γGlu), desB30 Human Insulin (Insulin Degludec, Control Compound 1)

The control compound insulin degludec was prepared according to Example 4 of patent CN105820233A.

Comparative Example 2

B29K(N(ε)-eicosanedioyl-γGlu-2×OEG), desB30 Human Insulin (Control Compound 2)

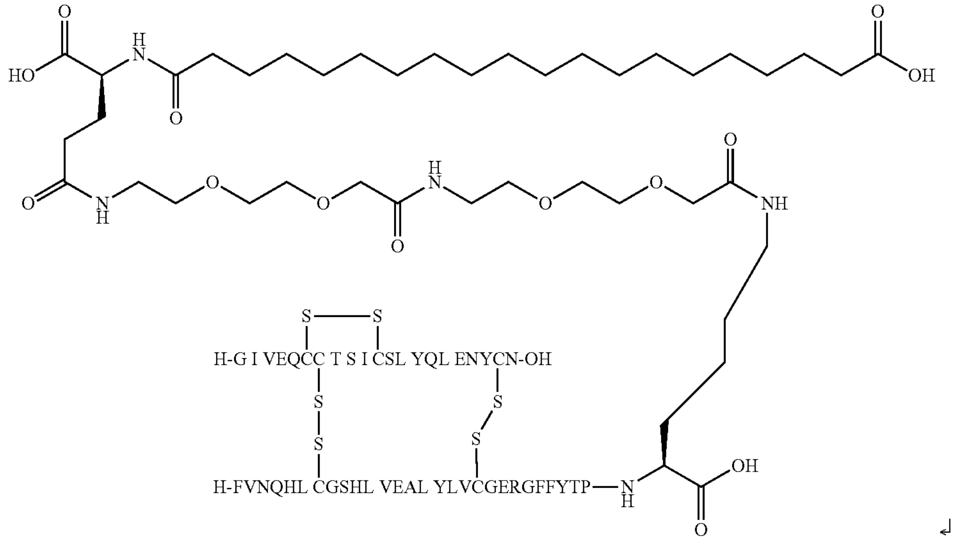

Control compound 2 was prepared by procedures similar to those described in section 2 of Example 1

LC-MS (ESI): m/z=1290.22[M+5H]5+

The intermediate tert-butyl eicosanedioyl-γGlu-(2×OEG-OSu)-OtBu was prepared by procedures similar to those described in section 3 of Example 1.

LC-MS (Sciex100API): m/z=971.61 $(M+1)^+$

Comparative Example 3

B29K(N(ε)-octadecanedioyl-γGlu-2×OEG), desB30 Human Insulin (Control Compound 3)

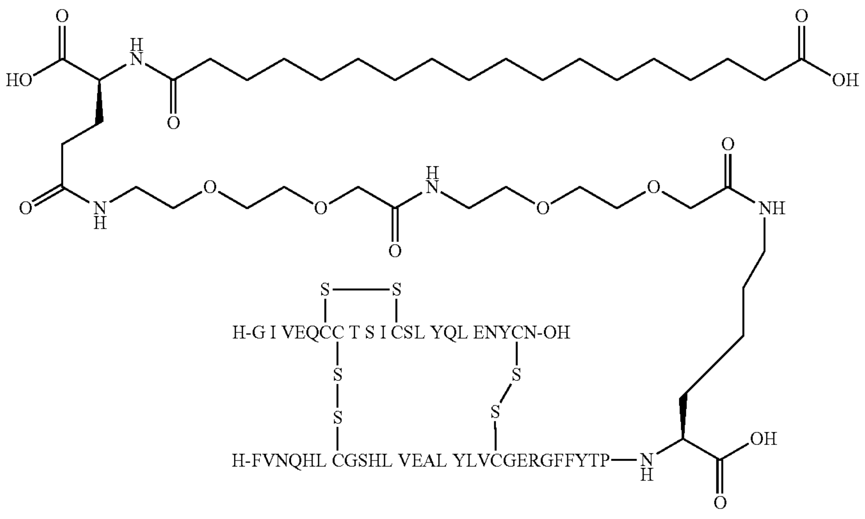

Control compound 3 was prepared by procedures similar to those described in section 2 of Example 1.

LC-MS (ESI): m/z=1284.61$[M+5H]^{5+}$

Comparative Example 4

B29K(N(ε)-octadecanedioyl-γGlu-6×OEG), desB30 Human Insulin (Control Compound 4)

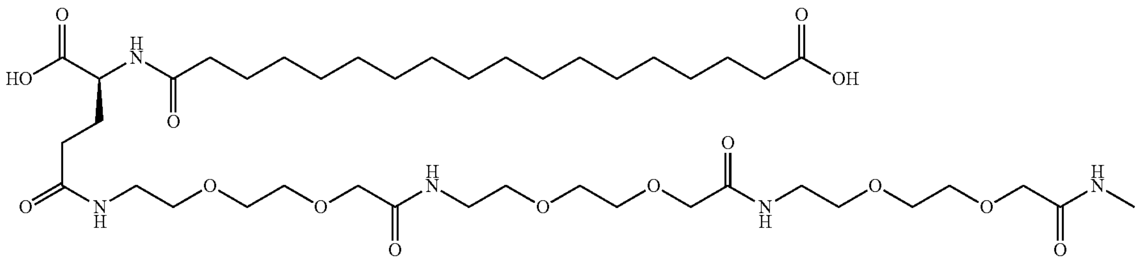

-continued

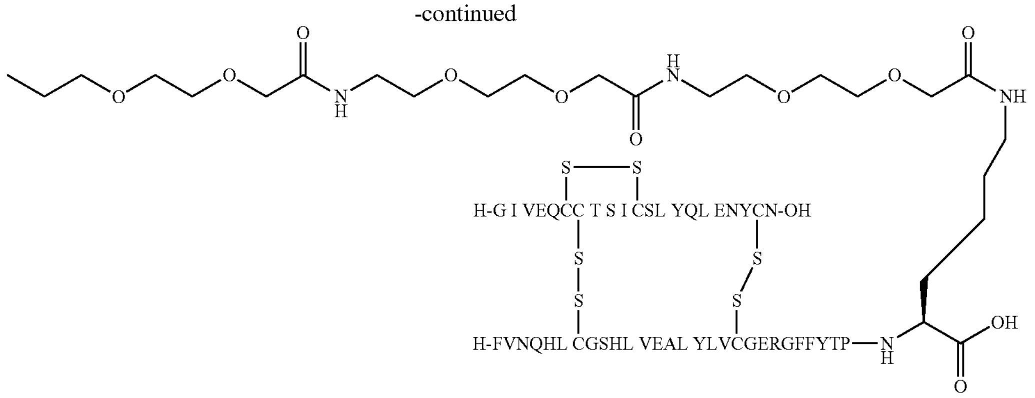

Control compound 4 was prepared by procedures similar to those described in section 2 of Example 1.

LC-MS (ESI): m/z=1400.68$[M+5H]^{5+}$

Example 6

Pharmacodynamic Study in db/db Mice

This study was intended to demonstrate the regulatory effect of the acylated insulins disclosed herein on blood glucose (BG) in a diabetic setting.

The acylated insulins of Examples 1-5 and control compounds of Comparative Examples 1-4 were tested in a single dose study in an obese, diabetic mouse model (db/db mice). The hypoglycemic effect of the acylated insulins was tested at a dose of 9 U/kg or 10 U/kg.

Male db/db (BKS/Lepr) mice aged 8-9 weeks were housed in appropriately sized feeding cages in a barrier environment with free access to standard food and purified water, with environmental conditions controlled at 40%-60% relative humidity (RH) and 22-24° C. After an adaptation period of 1-2 weeks, the mice were used in the experiment.

Before the start of the experiment on the day, the mice were evaluated for baseline blood glucose at time −1/1 h (9:30 a.m.) and weighed. Mice were each distributed to either the vehicle group or the treatment group based on random blood glucose and body weight, and subjected to the following treatments: subcutaneous injection of the vehicle or the acylated insulins (9 U/kg or 10 U/kg), wherein the vehicle contained: 19.6 mg/mL glycerol, 1.5 mg/mL phenol, 1.72 mg/mL m-cresol and 55 μg/mL zinc ions, with a pH value of 7.6.

The acylated insulins were each dissolved in the vehicle to an administration concentration of 1.8 U/mL or 2 U/mL, and the administration volume was 5 mL/kg (i.e., 50 μL/10 g body weight). The administration was performed once by subcutaneous injection (s.c.) at back of the neck. The acylated insulins were administered at about 10:30 a.m. (time 0), and during the treatment, the mice were fasted but had free access to water, and the blood glucose of the mice was evaluated at times 3 h, 6 h, 9 h, 12 h and 15 h after the administration. To simulate meals, oral glucose tolerance test (OGTT) was started after measurement of blood glucose at 15-h time point, and blood glucose was measured at times 30 min, 60 min, 120 min and 180 min after intragastric administration of a glucose solution (100 mg/mL, 10 mL/kg). The OGTT test was performed three times in a row, and according to the result of a pretest, the drug effect of the test compounds almost wore off at the last OGTT test, and the test was terminated after the blood glucose at 30-h time point was evaluated.

The tail of each mouse was cleaned with an alcohol cotton ball, and blood drops were collected from the tail using a disposable blood collection needle and measured with a glucometer and accompanying testing strips (Roche). The dose-response curve of blood glucose versus time was plotted for each single dose of acylated insulin.

In order to illustrate the effect of the acylated insulins disclosed herein on blood glucose, the area under the blood glucose-time curve (AUC) from time 0 to the monitoring endpoint was calculated for each individual dose-response curve. The smaller the AUC value, the better the hypoglycemic effect, and the better the drug effect.

Figure 1B:
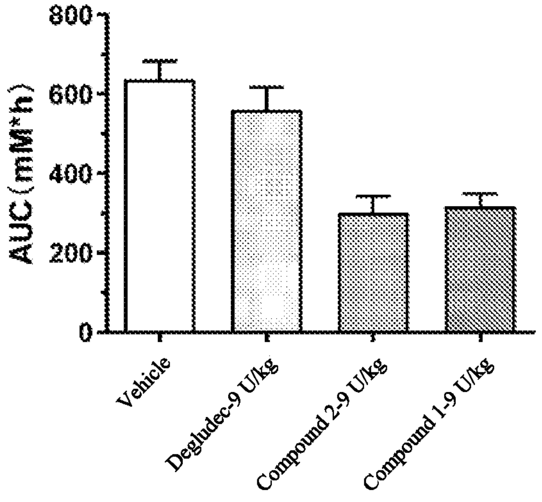
FIG. 1*b* shows, in correspondence with FIG. 1*a*, the AUC of the hypoglycemic effect of the compounds of Examples 1 and 2 in the present invention, insulin degludec and vehicle on db/db mice.

Test results: The hypoglycemic effect of the acylated insulins disclosed herein and the control compounds in db/db mice is shown in FIGS. 1a-6b and table 1, wherein specifically: FIGS. 1a and 1b show that the acylated insulins disclosed herein, such as compound 1 and compound 2, have significantly superior hypoglycemic effect in db/db mice compared to insulin degludec, and have prolonged the effective duration of action compared to insulin degludec.

Figure 2A:
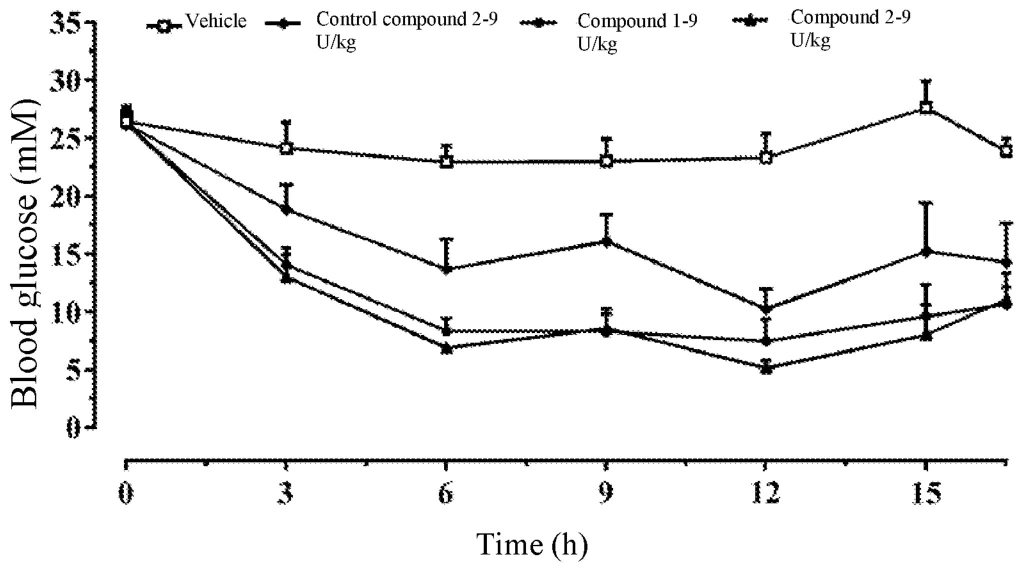
FIG. 2*a* shows the hypoglycemic effect of the compounds of Examples 1 and 2 and the compound of Comparative Example 2 in the present invention and vehicle on db/db mice.
Figure 2B:
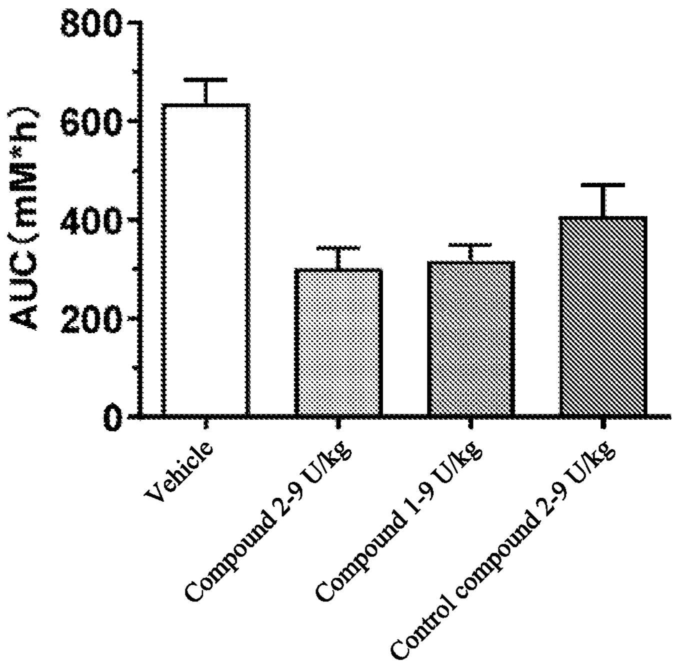
FIG. 2*b* shows, in correspondence with FIG. 2*a*, the AUC of the hypoglycemic effect of the compounds of Examples 1 and 2 and the compound of Comparative Example 2 in the present invention and vehicle on db/db mice.

FIGS. 2a and 2b show that the acylated insulins disclosed herein, such as compound 1 and compound 2, have significantly superior hypoglycemic effect in db/db mice compared to the control compound 2, and the drug effect of the compound 1 and compound 2 disclosed herein is increased by 39.5% and 45.1%, respectively, within a time range of 0-16.5 h after administration relative to the control compound 2, as shown in Table 1:

TABLE 1

Increase in drug effect of acylated insulins disclosed herein relative to control compound 2

| Compound/control compound | Example | Increase in drug effect relative to control compound 2 (%) |
|---|---|---|
| Compound 1 | Example 1 | 39.5% |
| Compound 2 | Example 2 | 45.1% |
| Control compound 2 | Comparative Example 2 | 0% |

Figure 3A:
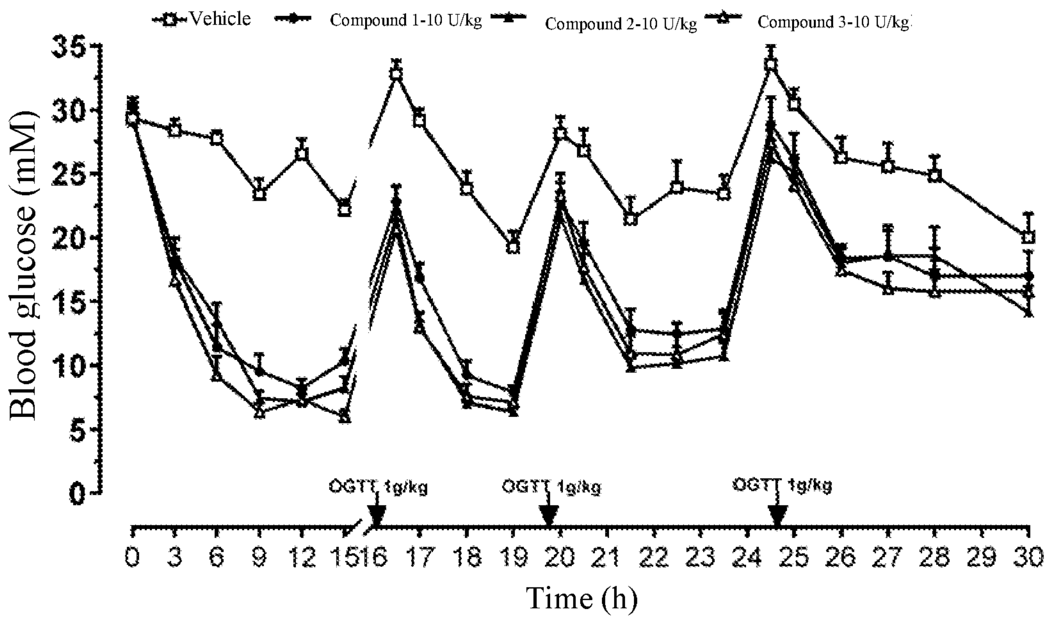
FIG. 3*a* shows the hypoglycemic effect and duration of action of the compounds of Examples 1-3 in the present invention and vehicle on db/db mice.
Figure 3B:
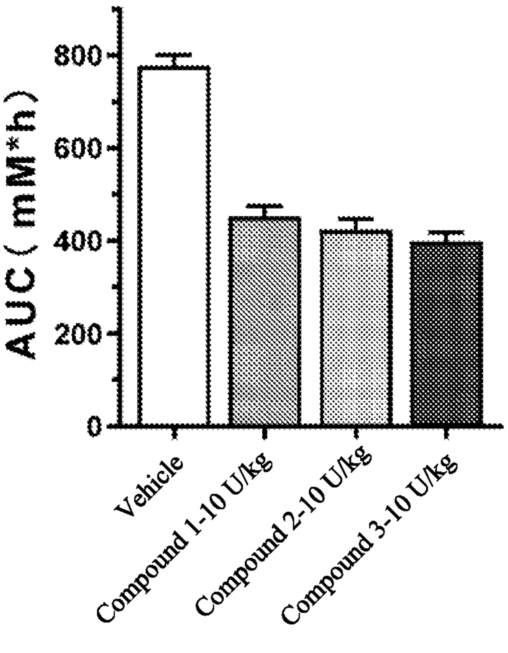
FIG. 3*b* shows, in correspondence with FIG. 3*a*, the AUC of the hypoglycemic effect of the compounds of Examples 1-3 in the present invention and vehicle on db/db mice.
Figure 4A:
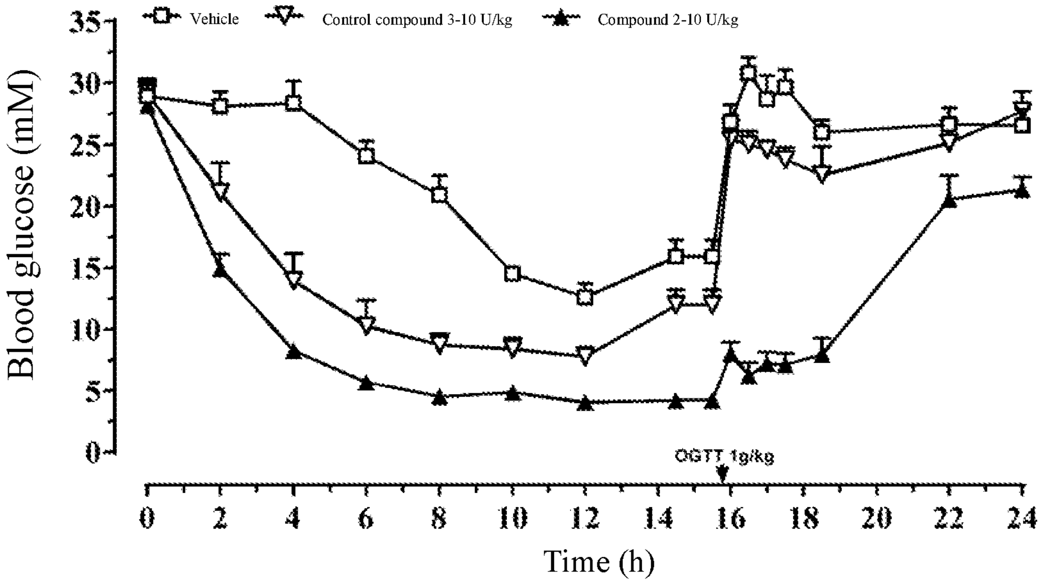
FIG. 4*a* shows the hypoglycemic effect and duration of action of the compound of Example 2 and the compound of Comparative Example 3 in the present invention and vehicle on db/db mice.
Figure 4B:
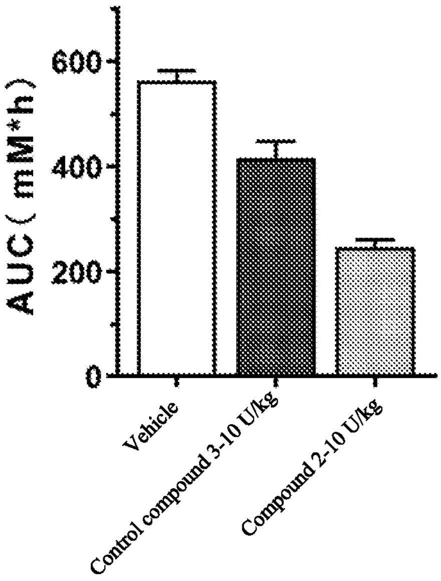
FIG. 4*b* shows, in correspondence with FIG. 4*a*, the AUC of the hypoglycemic effect of the compound of Example 2 and the compound of Comparative Example 3 in the present invention and vehicle on db/db mice.
Figure 5A:
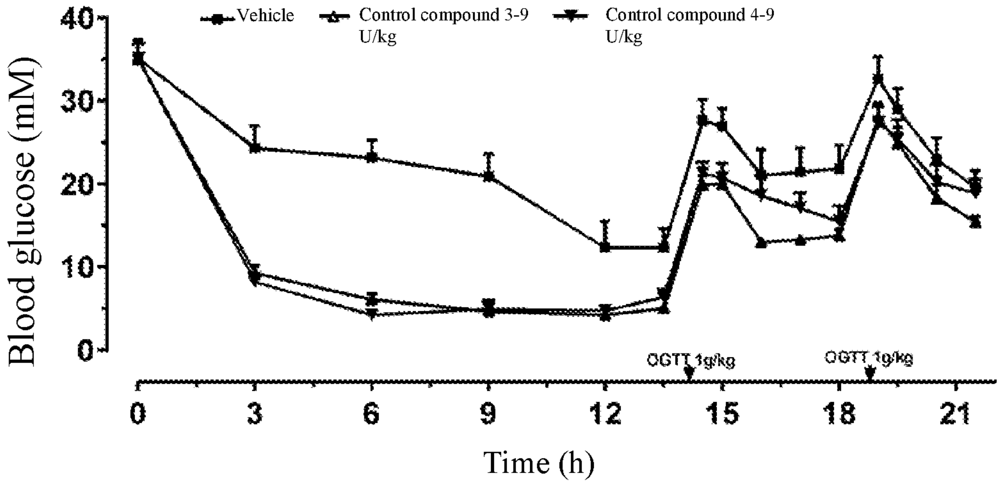
FIG. 5*a* shows the hypoglycemic effect and duration of action of the compounds of Comparative Examples 3-4 in the present invention and vehicle on db/db mice.
Figure 5B:
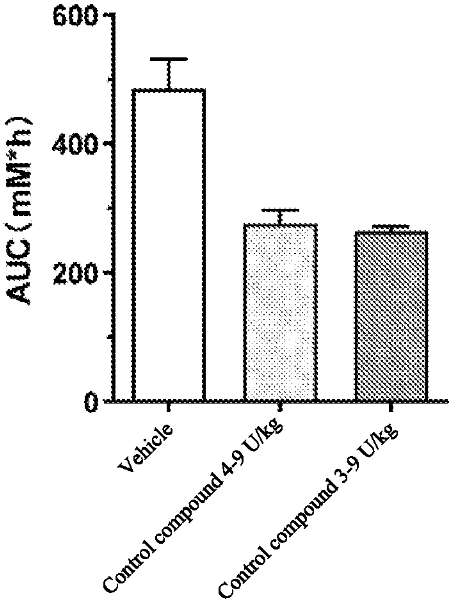
FIG. 5*b* shows, in correspondence with FIG. 5*a*, the AUC of the hypoglycemic effect of the compounds of Comparative Examples 3-4 in the present invention and vehicle on db/db mice.

Increase in drug effect relative to control compound 2(%)=[(AUC (test compound)−AUC (vehicle))/(AUC (control compound 2)−AUC (vehicle))−1]×100%, wherein the test compound refers to the acylated insulin disclosed herein FIGS. 3*a*-3*b* show that the compound 1, compound 2 and compound 3 disclosed herein all have very good drug effect and also have significantly prolonged duration of hypoglycemic effect as they are still effective in db/db mice when monitored at 30-h time point.

FIGS. 4*a*-5*b* show that the acylated insulins disclosed herein, such as compound 2, have a significantly superior hypoglycemic effect in db/db mice compared to the control compound 3 and control compound 4.

Figure 6A:
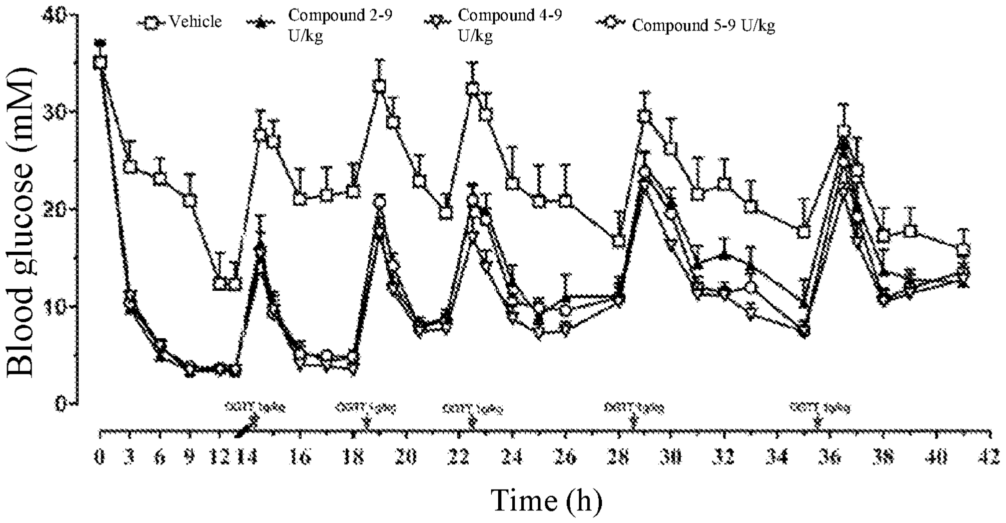
FIG. 6*a* shows the hypoglycemic effect and duration of action of the compounds of Example 2 and Examples 4-5 in the present invention and vehicle on db/db mice.
Figure 6B:
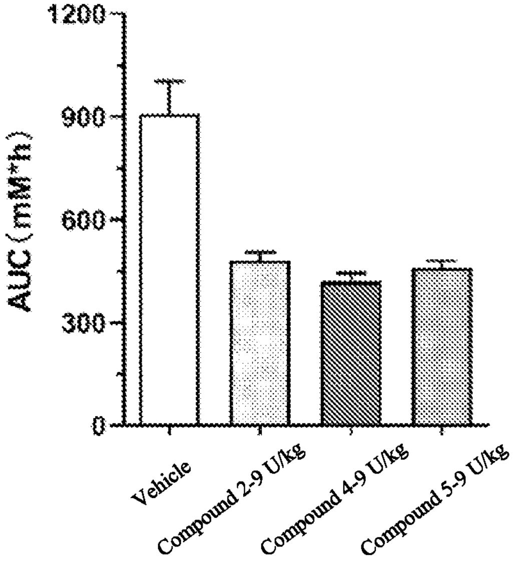
FIG. 6*b* shows, in correspondence with FIG. 6*a*, the AUC of the hypoglycemic effect of the compounds of Example 2 and Examples 4-5 in the present invention and vehicle on db/db mice.

FIGS. 6*a*-6*b* show that the compound 4, compound 5 and compound 2 disclosed herein all have very good drug effect and also have significantly prolonged duration of hypoglycemic effect as they are still effective in db/db mice when monitored at 41-h time point.

Example 7

Pharmacodynamic Study in Rats with Streptozotocin (STZ)-Induced Type 1 Diabetes (T1DM) Male wistar rats aged 8 weeks and weighed 180-220 g were housed in appropriately sized feeding cages (5 rats/cage) in a barrier environment with free access to standard food and purified water, with environmental conditions controlled at 40%-60% RH and 22-24° C. After an adaptation period of 4 days, the rats were fasted for 12 h and injected intraperitoneally gastric administration of glucose solution (100 mg/mL or 200 mg/mL, 10 mL/kg), and then the blood glucose was determined at times 30 min, 60 min, 120 min and 180 min after glycemic load.

The tail of each rat was cleaned with an alcohol cotton ball, and blood drops were collected from the tail using a disposable blood collection needle and measured with a glucometer (Roche) and accompanying testing strips.

The dose-response curve of blood glucose versus time was plotted for each single dose of acylated insulin. In order to illustrate the effect of the acylated insulins on blood glucose, the area under the blood glucose-time curve (AUC) from time 0 to the monitoring endpoint was calculated for each individual dose-response curve.

Figure 7A:
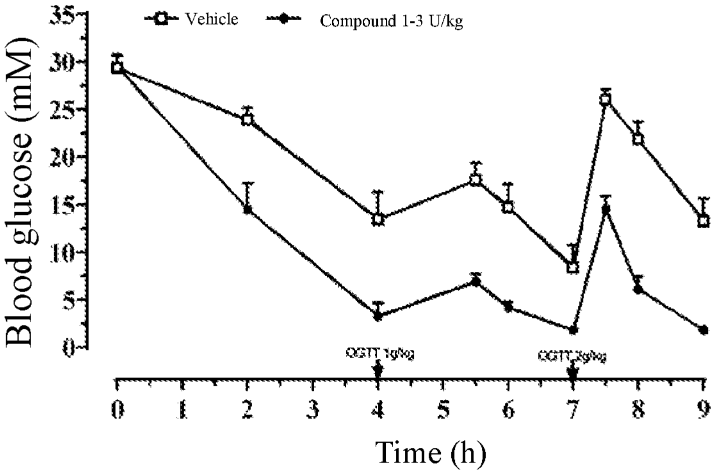
FIG. 7*a* shows the hypoglycemic effect of the compound of Example 1 in the present invention and vehicle on rats with streptozotocin (STZ)-induced type 1 diabetes (T1DM).
Figure 7B:
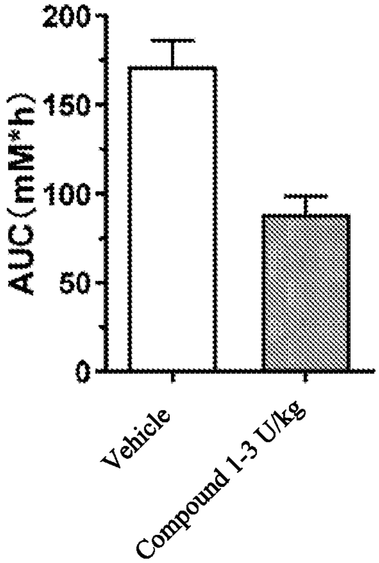
FIG. 7*b* shows, in correspondence with FIG. 7*a*, the AUC of the hypoglycemic effect of the compound of Example 1 in the present invention and vehicle on rats with STZ-induced type 1 diabetes (T1DM).

FIGS. 7*a*-7*b* show that the acylated insulin disclosed herein also has very good hypoglycemic effect, i.e., very good drug effect, in rats with type 1 diabetes (T1DM).

Example 8

N-$\varepsilon^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) peptide (Compound 6)

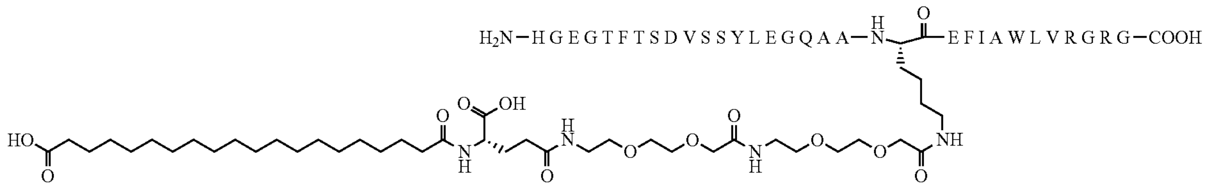

with streptozotocin (Sigma) solution (10 mg/mL, in 0.1 M citrate buffer) at 60 mg/kg. After administration, the drinking water was supplemented with glucose (20%) properly to prevent the rats from sudden hypoglycemia, and the glucose supplementation was removed 12 h later. 4 days after the administration of streptozotocin, random blood glucose detection was carried out, and rats with a blood glucose value higher than 20 mmol/L were selected as T1DM model rats for subsequent experiment.

Before the start of the experiment on the day, the rats were evaluated for baseline blood glucose at time −1/1 h (9:30 a.m.) and weighed. Rats were each distributed to either the vehicle group or the treatment group based on random blood glucose and body weight, and subjected to the following treatments: subcutaneous injection of the vehicle or the acylated insulin (3 U/kg), wherein the vehicle contained: 19.6 mg/mL glycerol, 1.5 mg/mL phenol, 1.72 mg/mL m-cresol and 55 μg/mL zinc ions, with a pH value of 7.6.

The acylated insulin was dissolved in the vehicle to an administration concentration of 1.5 U/mL, and the administration volume was 2 mL/kg (i.e., 0.2 mL/100 g body weight). The administration was performed once by subcutaneous injection (s.c.) at back of the neck. The acylated insulin was administered at about 9:30 a.m. (time 0), and the blood glucose of the rats was evaluated at times 2 h and 4 h after the administration. Oral glucose tolerance tests (OGTTs) were performed at 4-h and 7-h time points, respectively (see below for details).

Oral glucose tolerance test (OGTT) Detection time: blood was collected from the tail tip at the indicated time point to determine fasting blood glucose (0 min), followed by intra-

1. Preparation of N-$\varepsilon^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) peptide

[Gly8, Arg34]GLP-1-(7-37) peptide was prepared by a general protein recombinant expression method (for details, see Molecular Cloning: A Laboratory Manual (Fourth Edition), Michael R. Green, Cold Spring Harbor Press, 2012). [Gly8, Arg34]GLP-1-(7-37) peptide (5 g, 1.48 mmol) was dissolved in 100 mM aqueous $Na_2HPO_4$ solution (150 mL) and acetonitrile (100 mL) was added. The pH was adjusted to 10-12.5 with 1 N NaOH. Tert-butyl eicosanedioyl-γGlu (2×OEG-OSu)-OtBu (1.59 g, 1.63 mmol) was dissolved in acetonitrile (50 mL), and the solution was slowly added to a [Gly8, Arg34]GLP-1-(7-37) peptide solution. The pH was maintained at 10-12.5. After 120 min, the reaction mixture was added to water (150 mL), and the pH was adjusted to 5.0 with 1 N aqueous HCl. The precipitate was separated out by centrifugation and lyophilized. The crude product was added to a mixed solution of trifluoroacetic acid (60 mL) and dichloromethane (60 mL), and the mixture was stirred at room temperature for 30 min. The mixture was then concentrated to about 30 mL and poured into ice-cold n-heptane (300 mL), and the precipitated product was isolated by filtration and washed twice with n-heptane. The resulting precipitate was dried in vacuum and purified by ion exchange chromatography (Resource Q, 0.25%-1.25% ammonium acetate gradient in 42.5% ethanol, pH 7.5) and reverse phase chromatography (acetonitrile, water, TFA). The purified fractions were combined, adjusted to pH 5.2 with 1 N HCl, and separated to obtain the precipitate, which was lyophilized to obtain the title compound.

LC-MS (ESI): m/z=1028.79$[M+4H]^{4+}$

2. Preparation of intermediate tert-butyl eicosanedioyl-γGlu-(2×OEG-OSu)-OtBu 2.1 Tert-butyl eicosanedioyl-OSu Eicosanedioic acid mono-tert-butyl ester (20 g, 50.17 mmol) and NHS (5.77 g, 50.17 mmol) were mixed in dichloromethane (400 mL) under nitrogen atmosphere, and triethylamine (13.95 mL) was added. The resulting turbid mixture was stirred at room temperature, added with DCC (11.39 g, 55.19 mmol) and further stirred overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-OSu (24.12 g, yield 97%).

LC-MS (Sciex100API): m/z=496.36 $(M+1)^+$ 2.2 Tert-butyl eicosanedioyl-γGlu-OtBu Tert-butyl eicosanedioyl-OSu (24.12 g, 48.66 mmol) was dissolved in dichloromethane (250 mL), and the solution was stirred and added with H-Glu-OtBu (10.88 g, 53.53 mmol), triethylamine (12.49 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-OtBu (27.27 g, yield 96%).

LC-MS (Sciex100API): m/z=584.44 $(M+1)^+$ 2.3 Tert-butyl eicosanedioyl-γGlu-(OSu)-OtBu Tert-butyl eicosanedioyl-γGlu-OtBu (27.27 g, 46.71 mmol) was dissolved in dichloromethane (300 mL) under nitrogen atmosphere, and triethylamine (11.99 mL) was added. The mixture was stirred for 10 min, and NHS (5.38 g, 50.17 mmol) was added, followed by the addition of DCC (10.60 g, 51.38 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure. Tert-butyl methyl ether was added, and the mixture was stirred for 30 min and filtered in vacuum. The filter cake was dried in vacuum overnight to obtain tert-butyl eicosanedioyl-γGlu-(OSu)-OtBu (25.76 g, yield 81%).

LC-MS (Sciex100API): m/z=681.46 $(M+1)^+$ 2.4 Tert-butyl eicosanedioyl-γGlu-(2×OEG-OH)-OtBu Tert-butyl eicosanedioyl-γGlu-(OSu)-OtBu (25.76 g, 37.83 mmol) was dissolved in dichloromethane (250 mL), and the solution was stirred and added with 2×AEEA (11.66 g, 37.83 mmol), triethylamine (9.71 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OH)-OtBu (30.75 g, yield 93%).

LC-MS (Sciex100API): m/z=874.59 $(M+1)^+$ 2.5 Tert-butyl eicosanedioyl-γGlu-(2×OEG-OSu)-OtBu Tert-butyl eicosanedioyl-γGlu-(2×OEG-OH)-OtBu (30.75 g, 35.18 mmol) was dissolved in dichloromethane (300 mL) under nitrogen atmosphere, and triethylamine (9.03 mL) was added. The mixture was stirred for 10 min, and NHS (4.05 g, 35.18 mmol) was added, followed by the addition of DCC (7.98 g, 38.70 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OSu)-OtBu (31.09 g, yield 91%).

LC-MS (Sciex100API): m/z=971.61 $(M+1)^+$

Example 9

N-ε26-[2-(2-[2-(4-[19-carboxynonadecanoylamino]-4(S)-carboxybutanoylamino)ethoxy]ethoxy)acetyl][Gly8, Arg34]GLP-1-(7-37) Peptide (Compound 7)

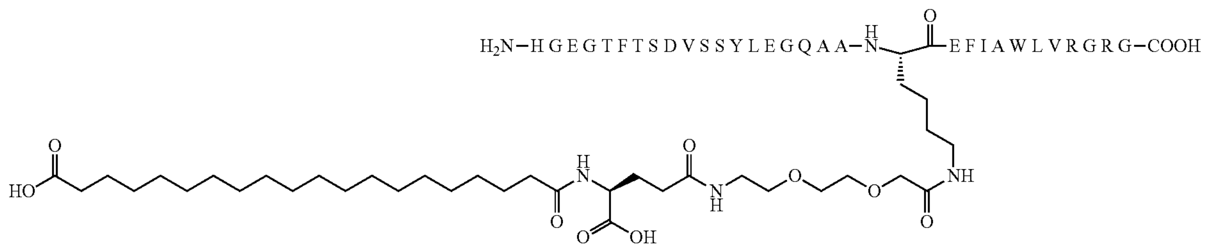

N-ε26-[2-(2-[2-(4-[19-carboxynonadecanoylamino]-4(S)-carboxybutanoylamino)ethoxy]ethoxy)acetyl][Gly8, Arg34]GLP-1-(7-37) peptide was prepared by procedures similar to those described in section 1 of Example 8.

LC-MS (ESI): m/z=992.52[M+4H]$^{4+}$

The intermediate tert-butyl eicosanedioyl-γGlu-(OEG-OSu)-OtBu was prepared by procedures similar to those described in section 2 of Example 8.

LC-MS (Sciex100API): m/z=826.54 (M+1)$^{+}$

Example 10

N-ε26-(19-carboxynonadecanoylamino)-4(S)-carboxybutanoyl-[Gly8, Arg34]GLP-1-(7-37) Peptide (Compound 8)

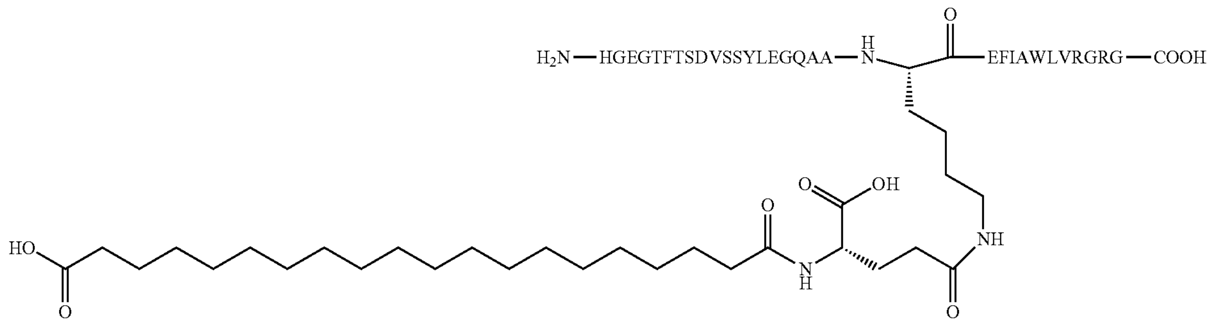

N-ε26-(19-carboxynonadecanoylamino)-4(S)-carboxybutanoyl-[Gly8, Arg34]GLP-1-(7-37) peptide was prepared by procedures similar to those described in section 1 of Example 8.

LC-MS (ESI): m/z=956.25[M+4H]$^{4+}$

The intermediate tert-butyl eicosanedioyl-γGlu-(OSu)-OtBu was prepared by procedures similar to those described in section 2 of Example 8.

LC-MS (Sciex100API): m/z=681.46 (M+1)$^{+}$

Example 11

N-ε26-(19-carboxynonadecanoylamino)-4(S)-carboxybutanoyl-[Arg34]GLP-1-(7-37) Peptide (Compound 9)

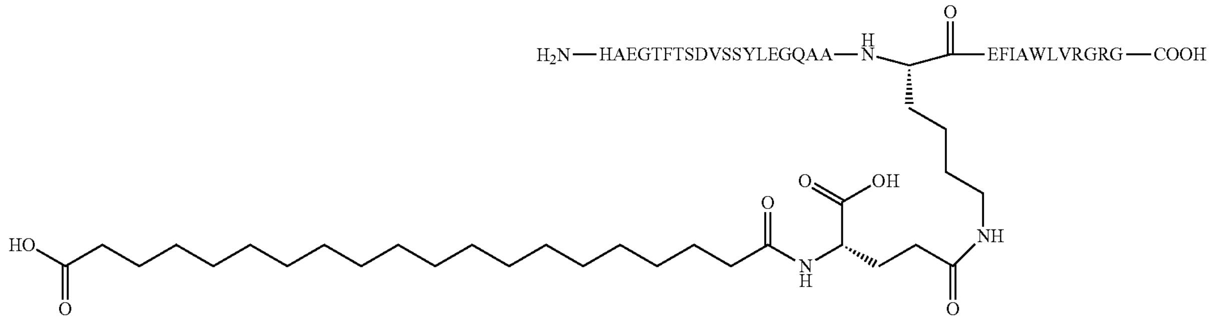

N-ε26-(19-carboxynonadecanoylamino)-4(S)-carboxybutanoyl-[Arg34]GLP-1-(7-37) peptide was prepared by procedures similar to those described in section 1 of Example 8.

LC-MS (ESI): m/z=959.75$[M+4H]^{4+}$

The intermediate tert-butyl eicosanedioyl-γGlu-(OSu)-OtBu was prepared by procedures similar to those described in section 2 of Example 8.

LC-MS (Sciex100API): m/z=681.46 $(M+1)^+$

Example 12

N-ε26-[2-(2-[2-(2-[2-(2-[4-(17-carboxyheptadecanoylamino)-4(S)-carboxybutanoylamino]ethoxy)ethoxy]acetylamino)ethoxy]ethoxy)acetyl][Gly8, Arg34]GLP-1-(7-37) Peptide (Compound 10)

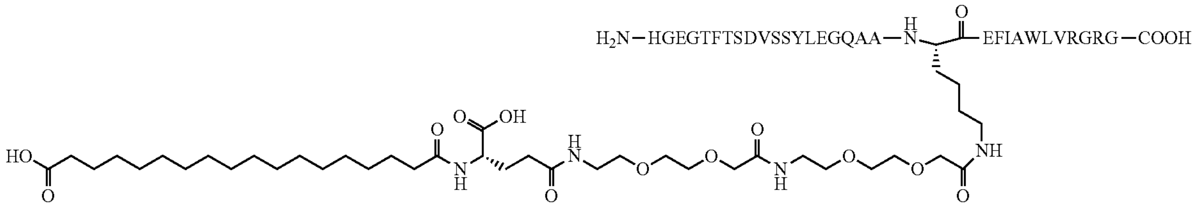

N-ε26-[2-(2-[2-(2-[2-(2-[4-(17-carboxyheptadecanoylamino)-4(S)-carboxybutanoylamino]ethoxy)ethoxy]acetylamino)ethoxy]ethoxy)acetyl][Gly8, Arg34]GLP-1-(7-37) peptide was prepared by procedures similar to those described in section 1 of Example 8.

LC-MS (ESI): m/z=1021.78$[M+4H]^{4+}$

Example 13

N-ε[26]-(17-carboxyheptadecanoylamino)-4(S)-carboxybutanoyl-[Gly8, Arg34]GLP-1-(7-37) Peptide (Compound 11)

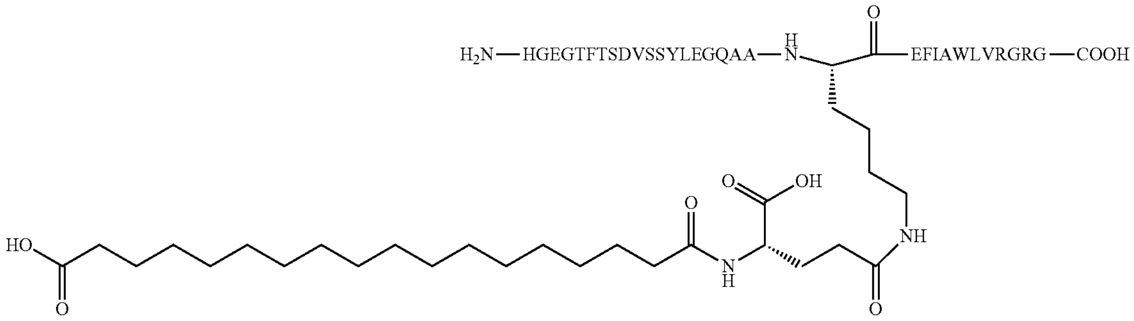

N-ε[26]-(17-carboxyheptadecanoylamino)-4(S)-carboxybutanoyl-[Gly8, Arg34]GLP-1-(7-37) peptide was prepared by procedures similar to those described in section 1 of Example 8.

LC-MS (ESI): m/z=949.24$[M+4H]^{4+}$

The intermediate tert-butyl octadecanedioyl-γGlu-(OSu)-OtBu was prepared by procedures similar to those described in section 2 of Example 8.

LC-MS (Sciex100API): m/z=653.43 $(M+1)^+$

Example 14

N-ε[26]-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) Peptide (Compound 12)

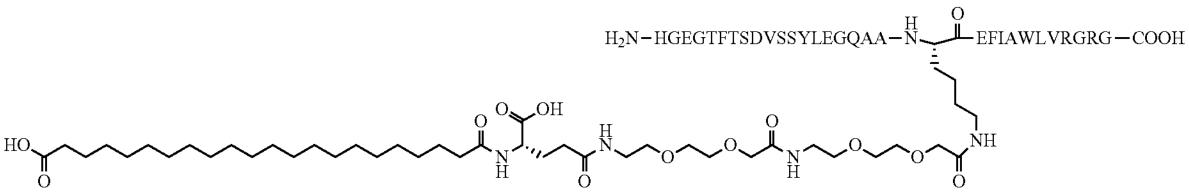

N-ε[26]-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide was prepared by procedures similar to those described in section 1 of Example 8.

LC-MS (ESI): m/z=1035.80$[M+4H]^{4+}$

The intermediate tert-butyl docosanedioyl-γGlu-(2×OEG-OSu)-OtBu was prepared by procedures similar to those described in section 2 of Example 8.

LC-MS (Sciex100API): m/z=999.64 $(M+1)^+$

Comparative Example 5

A14E, B16H, B25H, B29K(N(ε)-eicosanedioyl-γGlu-2×OEG), desB30 Human Insulin (Control Compound 5)

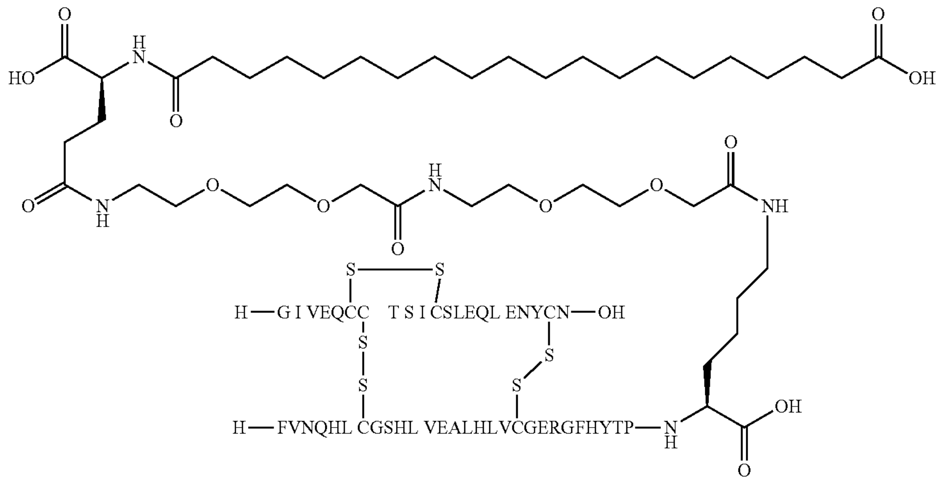

1. Preparation of A14E, B16H, B25H, B29K(N(ε)-eicosanedioyl-γGlu-2×OEG), desB30 Human Insulin A14E, B16H, B25H, desB30 human insulin was prepared using a conventional method for preparing insulin analogues (for details, see Glendorf T, Sprensen A R, Nishimura E, Pettersson I, & Kjeldsen T: Importance of the Solvent-Exposed Residues of the Insulin B Chain α-Helix for Receptor Binding; *Biochemistry,* 2008, 47:4743-4751). A14E, B16H, B25H, desB30 human insulin (5 g, 0.888 mmol) was dissolved in 100 mM aqueous $Na_2HPO_4$ solution (150 mL) and acetonitrile (100 mL) was added. The pH was adjusted to 10-12.5 with 1 N NaOH. Tert-butyl eicosanedioyl-γGlu-(2×OEG-OSu)-OtBu (0.948 g, 0.976 mmol) was dissolved in acetonitrile (50 mL), and the solution was slowly added to the insulin solution. The pH was maintained at 10-12.5.

After 120 min, the reaction mixture was added to water (150 mL), and the pH was adjusted to 5.0 with 1 N aqueous HCl. The precipitate was separated out by centrifugation and lyophilized. The lyophilized crude product was added to a mixed solution of trifluoroacetic acid (60 mL) and dichloromethane (60 mL), and the mixture was stirred at room temperature for 30 min. The mixture was then concentrated to about 30 mL and poured into ice-cold n-heptane (300 mL), and the precipitated product was isolated by filtration and washed twice with n-heptane. The resulting precipitate was dried in vacuum and purified by ion exchange chromatography (Resource Q, 0.25%-1.25% ammonium acetate gradient in 42.5% ethanol, pH 7.5) and reverse phase chromatography (acetonitrile, water, TFA). The purified fractions were combined, adjusted to pH 5.2 with 1 N HCl, and separated to obtain the precipitate, which was lyophilized to obtain the control compound 5.

LC-MS (ESI): m/z=1063.6852$[M+6H]^{6+}$

2. Preparation of Intermediate tert-butyl eicosanedioyl-γGlu-(2×OEG-OSu)-OtBu: by Procedures Similar to Those Described in Section 3 of Example 1

2.1 Tert-butyl eicosanedioyl-OSu

Eicosanedioic acid mono-tert-butyl ester (20 g, 50.17 mmol) and NHS (5.77 g, 50.17 mmol) were mixed in dichloromethane under nitrogen atmosphere, and triethylamine (13.95 mL) was added. The resulting turbid mixture was stirred at room temperature, added with DCC (11.39 g, 55.19 mmol) and further stirred overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-OSu (24.12 g, yield 97%).

LC-MS (Sciex100API): m/z=496.36 $(M+1)^+$ 2.2 Tert-butyl eicosanedioyl-γGlu-OtBu Tert-butyl eicosanedioyl-OSu (24.12 g, 48.66 mmol) was dissolved in dichloromethane (250 mL), and the solution was stirred and added with H-Glu-OtBu (10.88 g, 53.53 mmol), triethylamine (12.49 mL) and water sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-OtBu (27.27 g, yield 96%).

LC-MS (Sciex100API): m/z=584.44 $(M+1)^+$ 2.3 Tert-butyl eicosanedioyl-γGlu-(OSu)-OtBu Tert-butyl eicosanedioyl-γGlu-OtBu (27.27 g, 46.71 mmol) was dissolved in dichloromethane (300 mL) under nitrogen atmosphere, and triethylamine (11.99 mL) was added. The mixture was stirred for 10 min, and NHS (5.38 g, 50.17 mmol) was added, followed by the addition of DCC (10.60 g, 51.38 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure. Tert-butyl methyl ether was added, and the mixture was stirred for 30 min and filtered in vacuum. The filter cake was dried in vacuum overnight to obtain tert-butyl eicosanedioyl-γGlu-(OSu)-OtBu (25.76 g, yield 81%).

LC-MS (Sciex100API): m/z=681.46 $(M+1)^+$ 2.4 Tert-butyl eicosanedioyl-γGlu-(2×OEG-OH)-OtBu Tert-butyl eicosanedioyl-γGlu-(OSu)-OtBu (25.76 g, 37.83 mmol) was dissolved in dichloromethane (250 mL), and the solution was stirred and added with 2×AEEA (11.66 g, 37.83 mmol), triethylamine (9.71 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OH)-OtBu (30.75 g, yield 93%).

LC-MS (Sciex100API): m/z=874.59 $(M+1)^+$ 2.5 Tert-butyl eicosanedioyl-γGlu-(2×OEG-OSu)-OtBu Tert-butyl eicosanedioyl-γGlu-(2×OEG-OH)-OtBu (30.75 g, 35.18 mmol) was dissolved in dichloromethane (300 mL) under nitrogen atmosphere, and triethylamine (9.03 mL) was added. The mixture was stirred for 10 min, and NHS (4.05 g, 35.18 mmol) was added, followed by the addition of DCC (7.98 g, 38.70 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OSu)-OtBu (31.09 g, yield 91%).

LC-MS (Sciex100API): m/z=971.61 $(M+1)^+$

Example 15

A14E, B16H, B25H, B29K(N(ε)-eicosanedioyl-γGlu-6×OEG), desB30 Human Insulin (Compound 13)

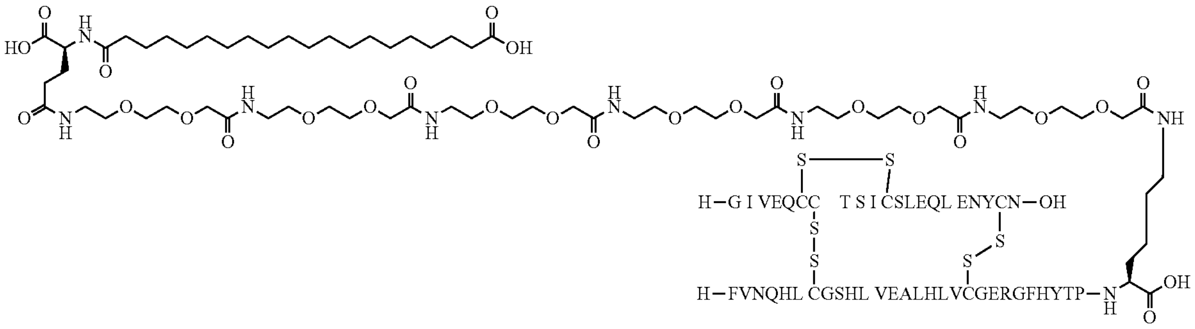

-

Compound A14E, B16H, B25H, B29K(N(ε)-eicosanedioyl-γGlu-6×OEG), desB30 human insulin was prepared by procedures similar to those described in section 1 of Comparative Example 5.

LC-MS (ESI): m/z=1160.3997$[M+6H]^{6+}$

The intermediate tert-butyl eicosanedioyl-γGlu-(6×OEG-OSu)-OtBu was prepared by procedures similar to those described in section 2 of Comparative Example 5.

LC-MS (Sciex100API): m/z=1551.90 $(M+1)^+$

Example 16

A14E, B16H, B25H, B29K(N(ε)-docosanedioyl-γGlu-6×OEG), desB30 Human Insulin (Compound 14)

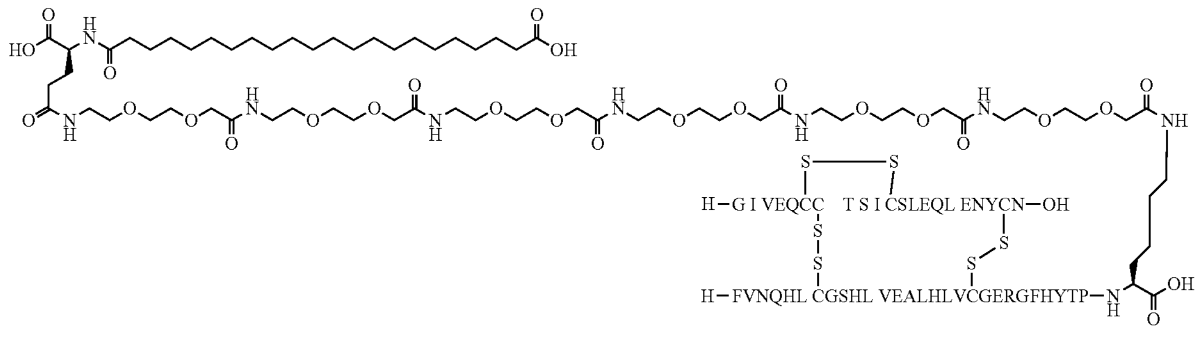

Compound A14E, B16H, B25H, B29K(N(ε)-docosanedioyl-γGlu-6×OEG), desB30 human insulin was prepared by procedures similar to those described in section 1 of Comparative Example 5.

LC-MS (ESI): m/z=1165.0674[M+6H]$^{6+}$

The intermediate tert-butyl docosanedioyl-γGlu-(6×OEG-OSu)-OtBu was prepared by procedures similar to those described in section 2 of Comparative Example 5.

LC-MS (Sciex100API): m/z=1579.94 (M+1)$^{+}$

Example 17

A14E, B16H, B25H, B29K(N(ε)-eicosanedioyl-γGlu-12×OEG), desB30 Human Insulin (Compound 15)

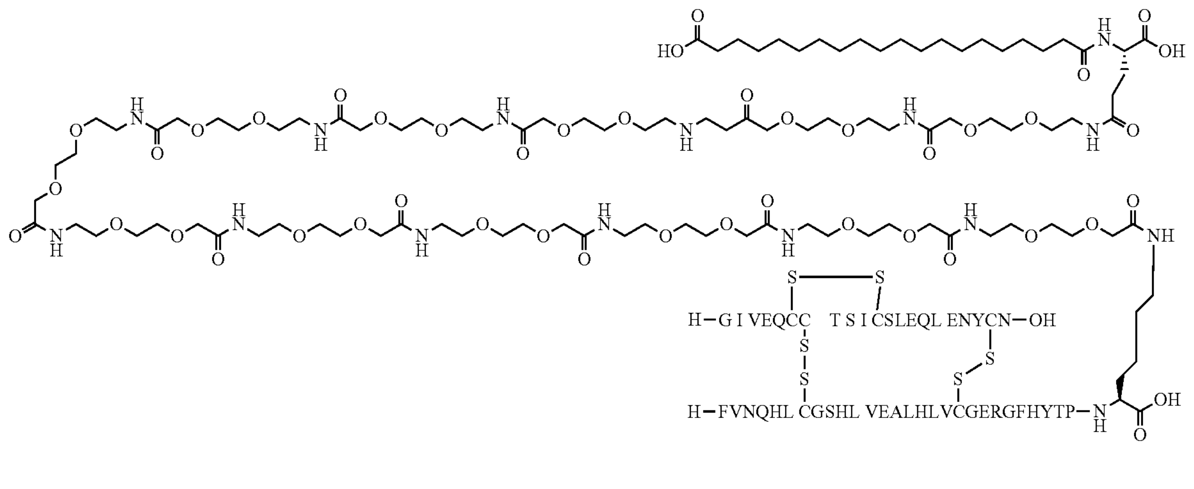

Compound A14E, B16H, B25H, B29K(N(ε)-eicosanedioyl-γGlu-12×OEG), desB30 human insulin was prepared by procedures similar to those described in section 1 of Comparative Example 5.

LC-MS (ESI): m/z=1305.4716[M+6H]$^{6+}$

The intermediate tert-butyl eicosanedioyl-γGlu-(12×OEG-OSu)-OtBu was prepared by procedures similar to those described in section 2 of Comparative Example 5.

LC-MS (Sciex100API): m/z=2423.35 (M+1)$^{+}$

Example 18

A14E, B16H, B25H, B29K(N(ε)-docosanedioyl-γGlu-12×OEG), desB30 Human Insulin (Compound 16)

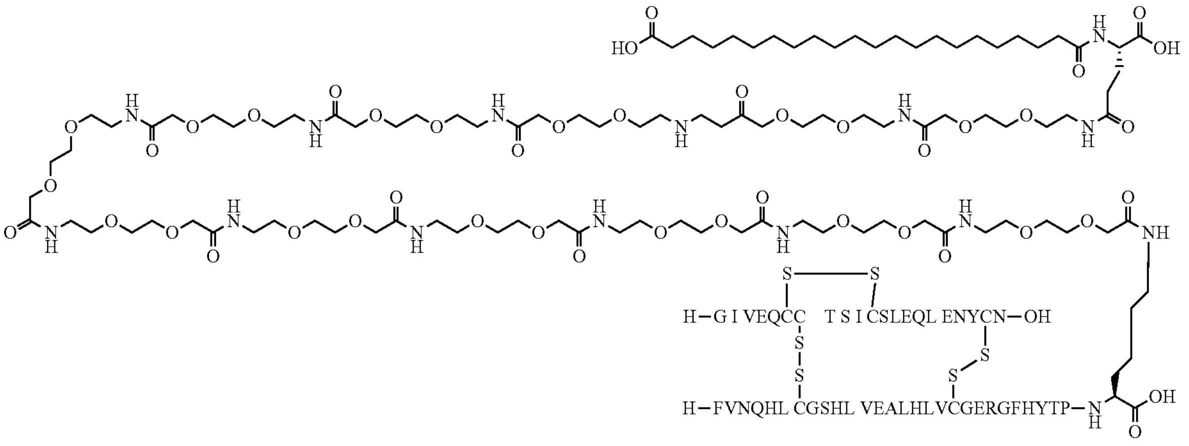

Compound A14E, B16H, B25H, B29K(N(ε)-docosanedioyl-γGlu-12×OEG), desB30 human insulin was prepared by procedures similar to those described in section 1 of Comparative Example 5.

LC-MS (ESI): m/z=1310.1425[M+6H]$^{6+}$

The intermediate tert-butyl docosanedioyl-γGlu-(12×OEG-OSu)-OtBu was prepared by procedures similar to those described in section 2 of Comparative Example 5.

LC-MS (Sciex100API): m/z=2451.38 (M+1)$^{+}$

Example 19

Reference was made to similar experiment procedures in Example 7 for pharmacodynamic study in rats with streptozotocin (STZ)-induced type 1 diabetes (T1DM).

Before the start of the experiment on the day, the rats were evaluated for baseline blood glucose at time −1 h (9:30 a.m.) and weighed. Rats were each distributed to either the vehicle group or the treatment group based on random blood glucose and body weight, and subjected to the following treatments: subcutaneous injection of vehicle, or subcutaneous injection of the title compounds of Comparative Example 5, Example 15 and Example 16 (control compound 5, compound 13 and compound 14) at a dose of 33.5 U/kg, wherein the vehicle contained: 5.65 mg/mL phenol, 15 mg/mL glycerol, 0.708 mg/mL disodium hydrogen phosphate and 0.585 mg/mL sodium chloride, with a pH value of 7.6.

The acylated insulins were each dissolved in the vehicle to an administration concentration of 33.5 U/mL, and the administration volume was 1 mL/kg (i.e., 0.1 mL/100 g body weight). The administration was performed once by subcutaneous injection (s.c.) at back of the neck. The acylated insulins were administered at about 9:30-10:00 a.m. (time 0), and the blood glucose of rats was monitored at times 3 h, 6 h, 9 h, 24 h, 48 h, 72 h, 96 h and 120 h after the administration.

The dose-response curve of blood glucose versus time was plotted for each single dose of acylated insulin (control compound 5, compound 14 and compound 13). In order to illustrate the effect of the acylated insulins on blood glucose, the area under the blood glucose-time curve (AUC) from time 0 to the monitoring endpoint was calculated for each individual dose-response curve. The smaller the AUC value, the better the hypoglycemic effect, and the better the drug effect.

Figure 8A:
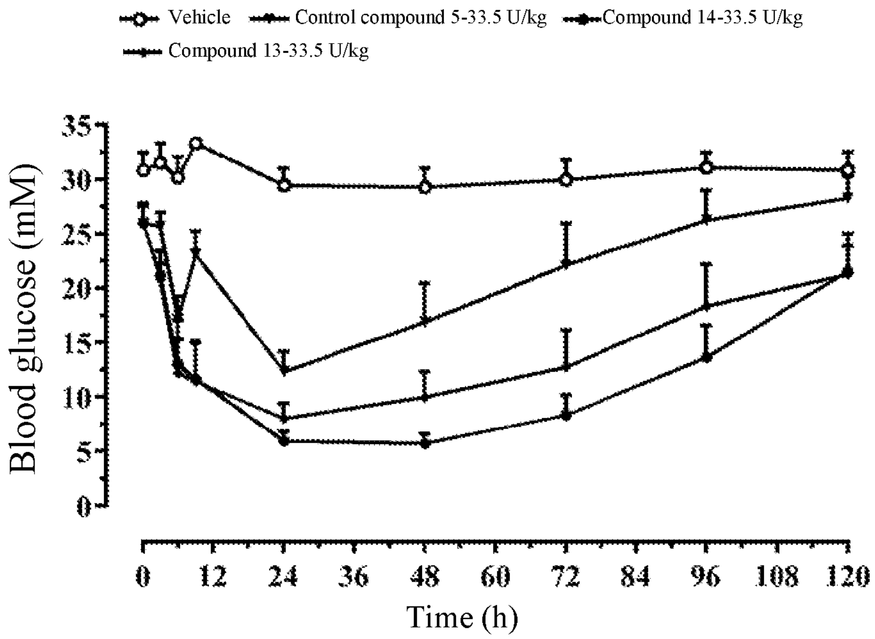
FIG. 8*a* shows the hypoglycemic effect of the title compounds of Comparative Example 5 and Examples 15 and 16 in the present invention and vehicle on rats with STZ-induced type 1 diabetes (T1DM).
Figure 8B:
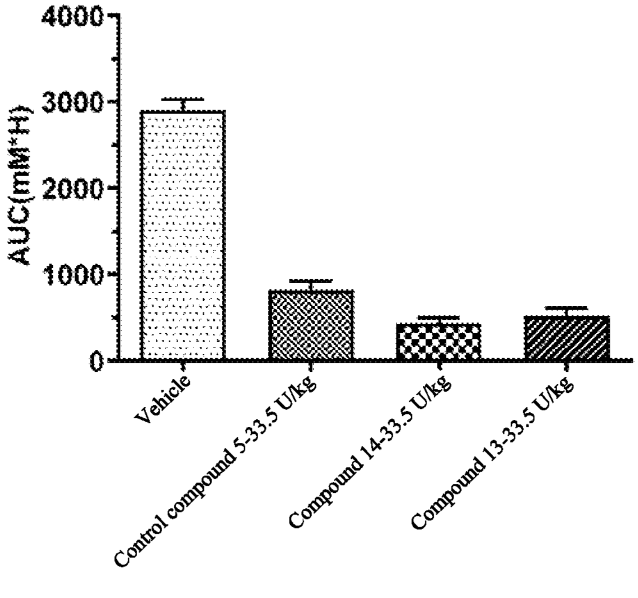
FIG. 8*b* shows, in correspondence with FIG. 8*a*, the AUC of the hypoglycemic effect of the title compounds of Comparative Example 5 and Examples 15 and 16 in the present invention and vehicle on rats with STZ-induced type 1 diabetes (T1DM).

FIGS. 8a-8b show that the acylated insulins disclosed herein have surprisingly increased drug effect. For example, relative to the compound of Comparative Example 5, compounds 13 and 14 (the title compounds of Examples 15 and 16) have better hypoglycemic effect, i.e., better drug effect, in rats with STZ-induced type 1 diabetes (T1DM).

Example 20

Reference was made to similar experiment procedures in Example 19 for pharmacodynamic study in female rats with streptozotocin (STZ)-induced type 1 diabetes (T1DM), except that the acylated insulins used were the title compounds of Examples 2 and 4 (compound 2 and compound 4) administered at a dose of 67 U/kg.

Figure 9A:
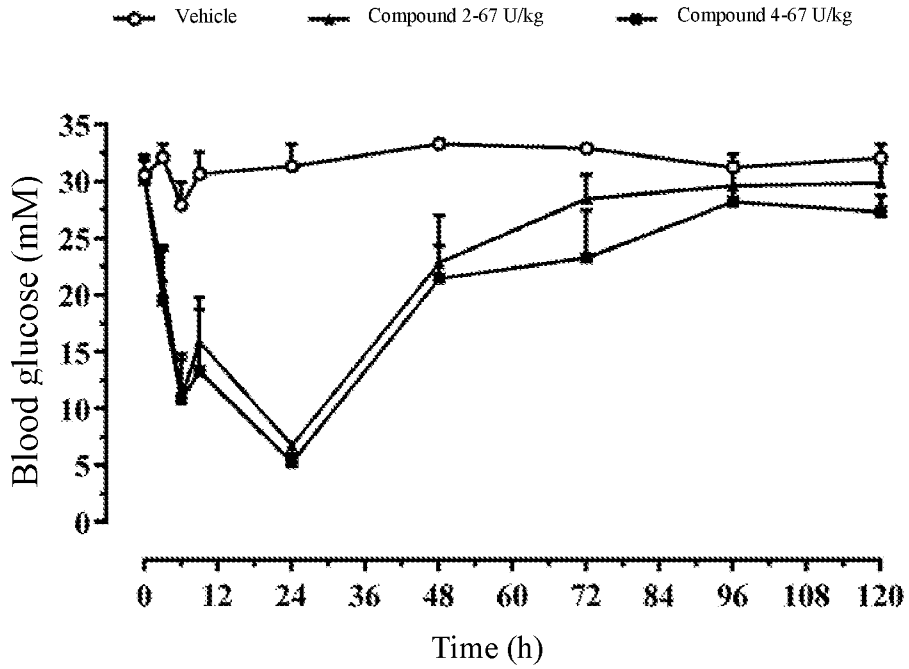
FIG. 9*a* shows the hypoglycemic effect of the compounds of Examples 2 and 4 in the present invention and vehicle on female rats with STZ-induced type 1 diabetes (T1DM).
Figure 9B:
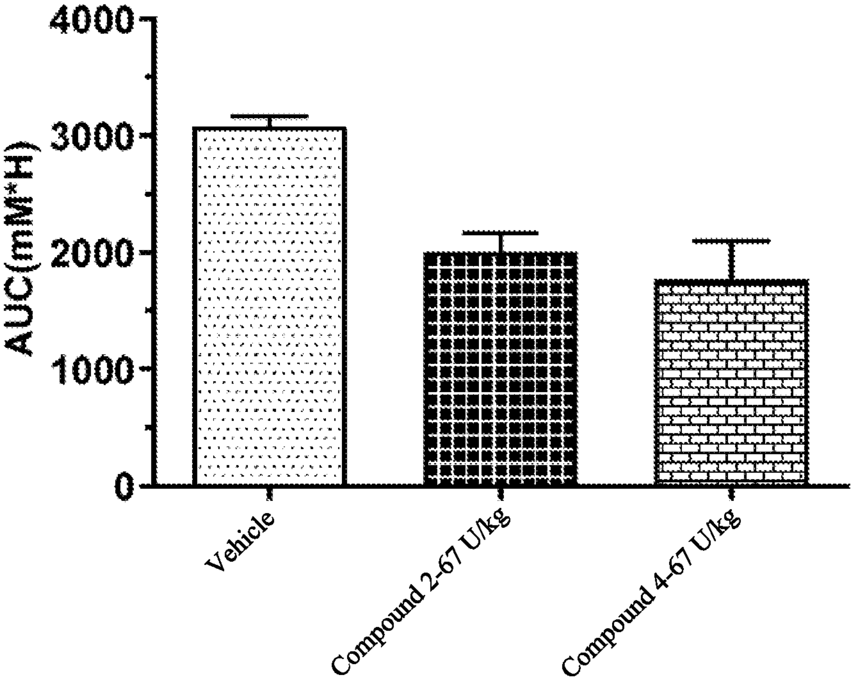
FIG. 9*b* shows, in correspondence with FIG. 9*a*, the AUC of the hypoglycemic effect of the compounds of Examples 2 and 4 in the present invention and vehicle on female rats with STZ-induced type 1 diabetes (T1DM).

The experiment results are as shown in FIGS. 9a-9b, which show that the acylated insulins (compound 2 and compound 4) disclosed herein also have very good hypoglycemic effect, i.e., very good drug effect, in female rats with type 1 diabetes (T1DM).

Example 21

Pharmacodynamic Study in db/db Mice

Reference was made to similar experiment procedures in Example 6 for testing the title compounds of Comparative Example 5 and Examples 15 and 16 (i.e., control compound 5, compound 13 and compound 14) in a single dose study in an obese, diabetic mouse model (db/db mice). The hypoglycemic effect of the acylated insulins was tested at a dose of 9 U/kg.

Male db/db (BKS/Lepr) mice aged 8-9 weeks were housed in appropriately sized feeding cages in a barrier environment with free access to standard food and purified water, with environmental conditions controlled at 40%-60% RH and 22-24° C. After an adaptation period of 1-2 weeks, the mice were used in the experiment.

Before the start of the experiment on the day, the mice were evaluated for baseline blood glucose at time −1/1 h (9:30 a.m.) and weighed. Mice were each distributed to either the vehicle group or the treatment group based on random blood glucose and body weight, and subjected to the following treatments: subcutaneous injection of vehicle, or subcutaneous injection of the acylated insulins at a dose of 9 U/kg, wherein the vehicle contained: 5.65 mg/mL phenol, 15 mg/mL glycerol, 0.708 mg/mL disodium hydrogen phosphate and 0.585 mg/mL sodium chloride, with a pH value of 7.6.

The acylated insulins were each dissolved in the vehicle to an administration concentration of 1.8 U/mL, and the administration volume was 5 mL/kg (i.e., 50 μL/10 g body weight). The administration was performed once by subcutaneous injection (s.c.) at back of the neck. The acylated insulins were administered at about 10:30 a.m. (time 0), and during the treatment, the mice were fasted but had free access to water, and the blood glucose of the mice was evaluated at times 3 h, 6 h, 9 h and 21.5 h after the administration. To simulate meals, oral glucose tolerance test (OGTT) was started after measurement of blood glucose at 21.5-h time point in the test. Blood glucose was measured at times 30 min, 60 min, 120 min and 360 min after intragastric administration of a glucose solution (100 mg/mL, 7.5 mL/kg). After the 360-min time point blood glucose was measured in the first OGTT test, the second OGTT test was started, and the blood glucose was measured at times 30 min, 90 min, 210 min and 360 min after intragastric administration of a glucose solution (50 mg/mL, 10 mL/kg). After the 360-min time point blood glucose was measured in the second OGTT test, the third OGTT test was started, and the blood glucose was measured at times 30 min, 60 min and 120 min after intragastric administration of a glucose solution (50 mg/mL and 10 mL/kg). The drug effect of the test compounds hadn't worn off at the last OGTT test, and the test was terminated after the blood glucose at 36-h time point was evaluated.

The tail of each mouse was cleaned with an alcohol cotton ball, and blood drops were collected from the tail using a disposable blood collection needle and measured with a glucometer and accompanying testing strips (Roche). The dose-response curve of blood glucose versus time was plotted for each single dose of acylated insulin. In order to illustrate the effect of the acylated insulins on blood glucose, the area under the blood glucose-time curve (AUC) from time 0 to the monitoring endpoint was calculated for each individual dose-response curve. The smaller the AUC value, the better the hypoglycemic effect, and the better the drug effect.

Figure 10A:
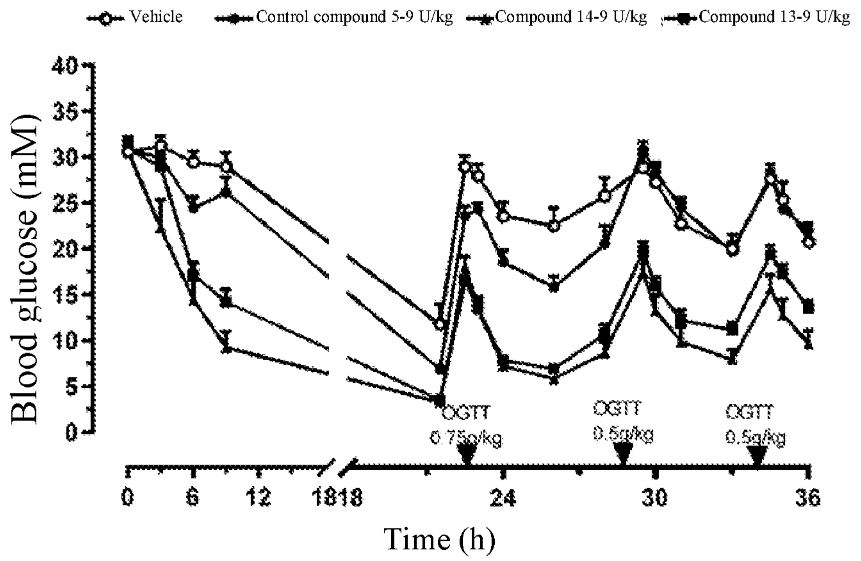
FIG. 10*a* shows the hypoglycemic effect of the title compounds of Comparative Example 5 and Examples 15 and 16 in the present invention and vehicle on db/db mice.
Figure 10B:
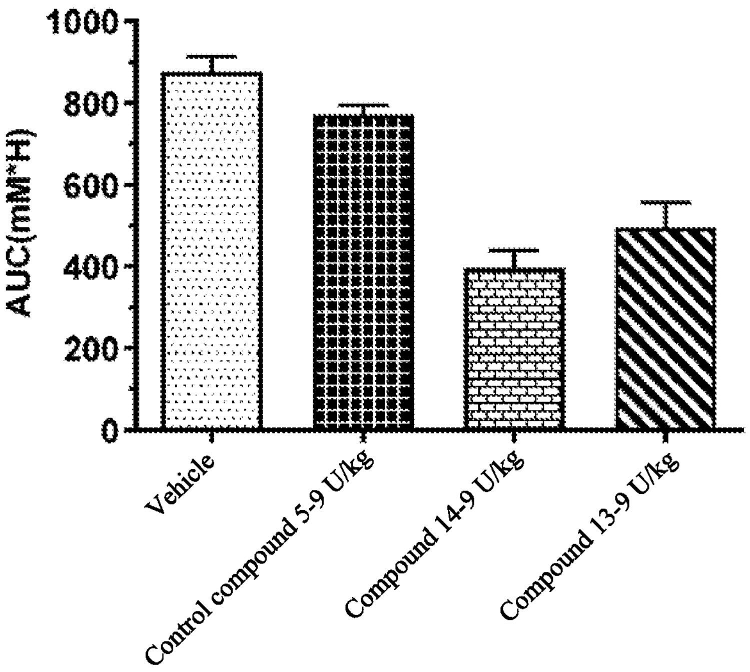
FIG. 10*b* shows, in correspondence with FIG. 10*a*, the AUC of the hypoglycemic effect of the title compounds of Comparative Example 5 and Examples 15 and 16 in the present invention and vehicle on db/db mice.

FIGS. 10*a*-10*b* show that relative to control compound 5, the acylated insulins (compound 14 and compound 13) disclosed herein have significantly improved hypoglycemic effect in db/db mice with type 2 diabetes.

Example 22

Pharmacodynamic Study in Rats with Streptozotocin (STZ)-Induced Type 1 Diabetes (T1DM) SD rats (half female and half male) aged 8 weeks and weighed 180-220 g were housed in appropriately sized feeding cages (5 rats/cage) in a barrier environment with free access to standard food and purified water, with environmental conditions controlled at 40%-60% RH and 22-24° C.

After an adaptation period of 4 days, the rats were fasted for 12 h and injected intraperitoneally with streptozotocin (Sigma) solution (10 mg/mL, in 0.1 M citrate buffer) at 60 mg/kg. 3 days after the administration of streptozotocin, random blood glucose detection was carried out, and rats with a blood glucose value higher than 20 mmol/L were selected as T1DM model rats for subsequent experiment.

The experiment was started 14 days after molding. Before the start of the experiment on the day, the rats were evaluated for baseline blood glucose at time −1/1 h (9:30 a.m.) and weighed. Rats were each distributed to either the vehicle group or the treatment group based on random blood glucose and body weight, and subjected to the following treatments: subcutaneous injection of vehicle, or subcutaneous injection of the title compounds of Comparative Example 5, Example 17 and Example 18 (i.e., control compound 5, compound 15 and compound 16) at a dose of 25 U/kg, wherein the vehicle contained: 5.65 mg/mL phenol, 15 mg/mL glycerol, 0.708 mg/mL disodium hydrogen phosphate and 0.585 mg/mL sodium chloride, with a pH value of 7.6.

The acylated insulins were each dissolved in the vehicle to an administration concentration of 25 U/mL, and the administration volume was 1 mL/kg (i.e., 0.1 mL/100 g body weight). The administration was performed by subcutaneous injection (s.c.) at back of the neck and was repeated 4 times at an interval of 4 days, and the SD rats had free access to food and water during the experiment. The acylated insulins were administered at about 9:30-10:00 a.m. (time 0). The blood glucose of rats was monitored at times 3 h, 6 h, 9 h, 24 h, 48 h, 72 h and 96 h after the first administration, and the blood glucose of rats was monitored at times 6 h and 24 h after each of the following administrations.

The dose-response curve of blood glucose versus time was plotted for each single dose of acylated insulin. In order to illustrate the effect of the acylated insulins on blood glucose, the area under the blood glucose-time curve (AUC) from time 0 to the monitoring endpoint was calculated for each individual dose-response curve.

TABLE 2

Increase in drug effect of acylated insulins disclosed herein relative to control compound 5

| Compound/control compound | Example | Increase in drug effect relative to control compound 5 (%) |
|---|---|---|
| Compound 15 | Example 17 | 125% |
| Compound 16 | Example 18 | 142% |
| Control compound 5 | Comparative Example 5 | 0% |

Figure 11A:
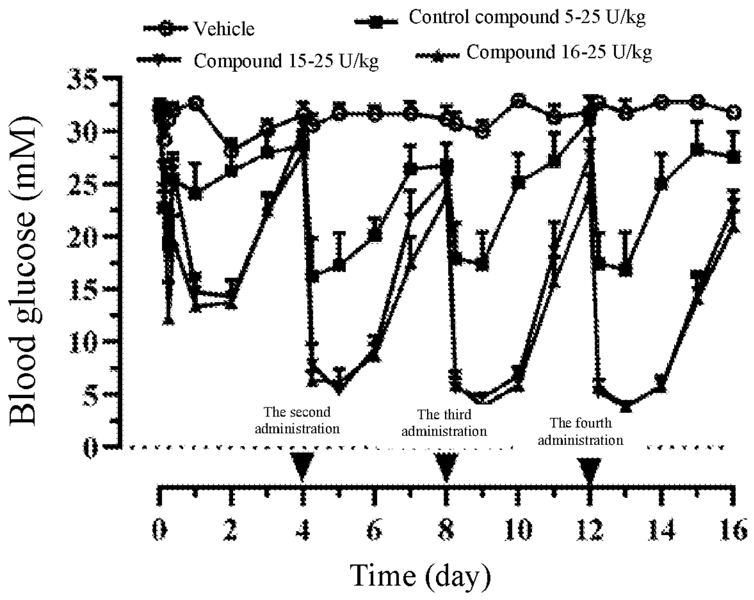
FIG. 11*a* shows the hypoglycemic effect of the title compounds of Comparative Example 5 and Examples 17 and 18 in the present invention and vehicle on rats with STZ-induced type 1 diabetes (T1DM).
Figure 11B:
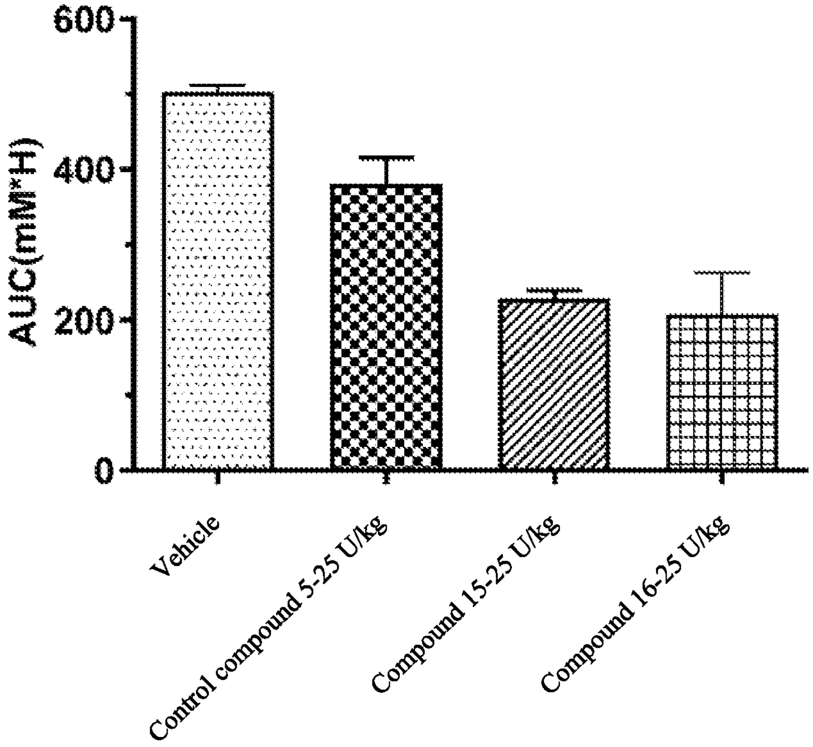
FIG. 11*b* shows, in correspondence with FIG. 11*a*, the AUC of the hypoglycemic effect of the title compounds of Comparative Example 5 and Examples 17 and 18 in the present invention and vehicle on rats with STZ-induced type 1 diabetes (T1DM).

Increase in drug effect relative to control compound 5(%)=[(AUC (test compound)−AUC (vehicle))/(AUC (control compound 5)−AUC (vehicle))−1]×100%, wherein the test compound refers to the acylated insulin disclosed herein As shown in FIGS. 11*a*-11*b* and Table 2, relative to the control compound 5, the acylated insulins disclosed herein have surprisingly increased hypoglycemic effect in rats with type 1 diabetes (T1DM) after administration, and the hypoglycemic effect of both compound 15 and compound 16 is significantly superior to that of control compound 5.

Example 23

Pharmacodynamic Study in Rats with Streptozotocin (STZ)-Induced Type 1 Diabetes (T1DM) SD rats (half female and half male) aged 8 weeks and weighed 180-220 g were housed in appropriately sized feeding cages (5 rats/cage) in a barrier environment with free access to standard food and purified water, with environmental conditions controlled at 40%-60% RH and 22-24° C.

After an adaptation period of 4 days, the rats were fasted for 12 h and injected intraperitoneally with streptozotocin (Sigma) solution (10 mg/mL, in 0.1 M citrate buffer) at 60 mg/kg. 3 days after the administration of streptozotocin, random blood glucose detection was carried out, and rats with a blood glucose value higher than 20 mmol/L were selected as T1DM model rats for subsequent experiment.

The experiment was started 14 days after molding. Before the start of the experiment on the day, the rats were evaluated for baseline blood glucose at time −1/1 h (9:30 a.m.) and weighed. Rats were each distributed to either the vehicle group or the treatment group based on random blood glucose and body weight, and subjected to the following treatments: subcutaneous injection of vehicle, or subcutaneous injection of the title compounds of Comparative Example 5 and Example 16 (i.e., control compound 5 and compound 14) at a dose of 25 U/kg, wherein the vehicle contained: 5.65 mg/mL phenol, 15 mg/mL glycerol, 0.708 mg/mL disodium hydrogen phosphate and 0.585 mg/mL sodium chloride, with a pH value of 7.6.

The acylated insulins were each dissolved in the vehicle to an administration concentration of 25 U/mL, and the administration volume was 1 mL/kg (i.e., 0.1 mL/100 g body weight). The administration was performed by subcutaneous injection (s.c.) at back of the neck and was repeated 4 times at an interval of 4 days, and the SD rats had free access to food and water during the experiment. The acylated insulins were administered at about 9:30-10:00 a.m. (time 0). The blood glucose of rats was monitored at times 3 h, 6 h, 9 h, 24 h, 48 h, 72 h and 96 h after the first administration, and the blood glucose of rats was monitored at times 6 h and 24 h after each of the following administrations.

The dose-response curve of blood glucose versus time was plotted for each single dose of acylated insulin. In order to illustrate the effect of the acylated insulins on blood glucose, the area under the blood glucose-time curve (AUC) from time 0 to the monitoring endpoint was calculated for each individual dose-response curve.

Figure 12A:
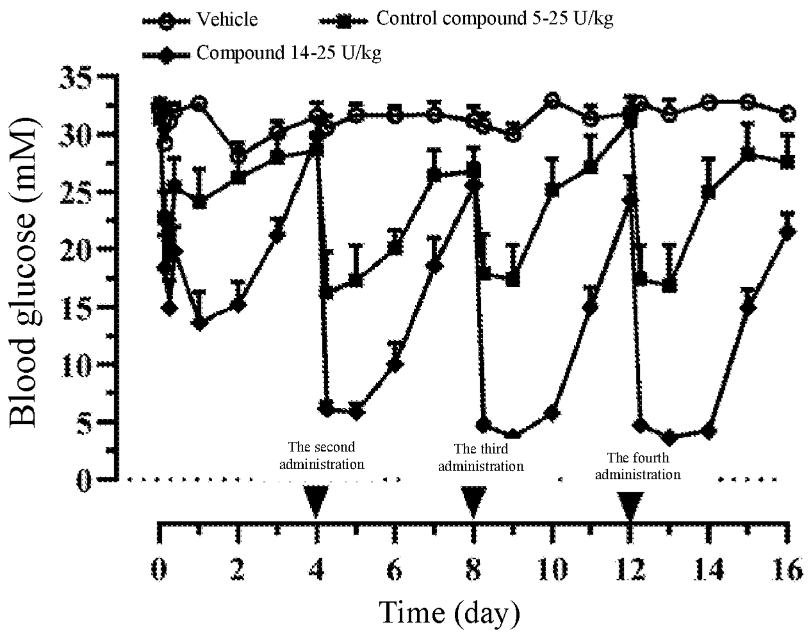
FIG. 12*a* shows the hypoglycemic effect of the title compounds of Comparative Example 5 and Example 16 in the present invention and vehicle on rats with STZ-induced type 1 diabetes (T1DM).
Figure 12B:
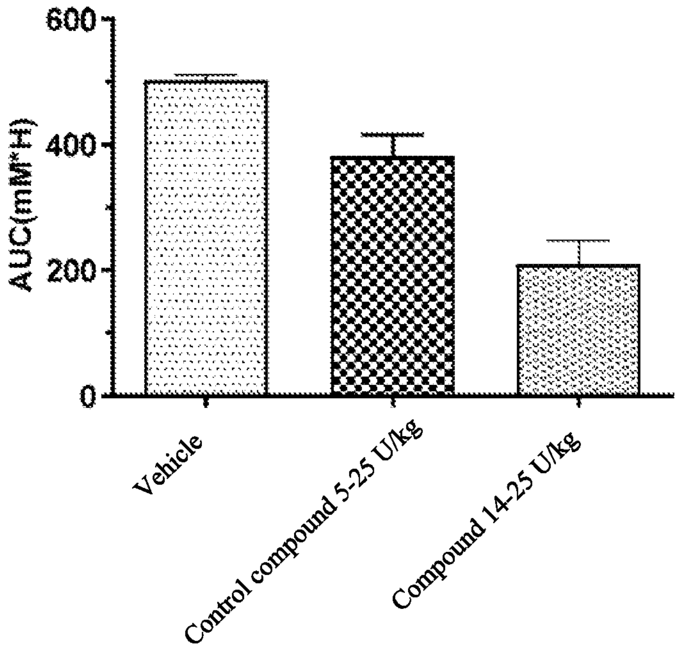
FIG. 12*b* shows, in correspondence with FIG. 12*a*, the AUC of the hypoglycemic effect of the title compounds of Comparative Example 5 and Example 16 in the present invention and vehicle on rats with STZ-induced type 1 diabetes (T1DM).

As shown in FIGS. 12*a*-12*b* and Table 2, relative to the control compound 5, the acylated insulin disclosed herein have surprisingly increased hypoglycemic effect in rats with type 1 diabetes (T1DM) after administration, and the hypoglycemic effect of compound 14 is significantly superior to that of control compound 5.

Example 24

Pharmacodynamic Study in C57/6J Mice with Streptozotocin (STZ)-Induced Type 1 Diabetes (T1DM)

This study was intended to demonstrate the regulatory effect of a composition comprising an acylated insulin disclosed herein and insulin aspart on blood glucose (BG) in C57/6J mice with streptozotocin (STZ)-induced type 1 diabetes (T1DM).

Male C57/6J mice (purchased from Vital River) aged 4-6 weeks were housed in appropriately sized feeding cages in a barrier environment with free access to standard food and purified water, with environmental conditions controlled at 40%-60% RH and 22-24° C. After an adaptation period of 1-2 weeks, the mice were used in the experiment.

After an adaptation period, the mice were fasted for 12 h and injected intraperitoneally with streptozotocin (Sigma) solution (10 mg/mL, in 0.1 M citrate buffer) at 150 mg/kg. 3 days after the administration of streptozotocin, random blood glucose detection was carried out, and mice with a blood glucose value higher than 20 mmol/L were selected as T1DM model mice for subsequent experiment.

Before the start of the experiment on the day, the mice were detected for random blood glucose and weighed. Mice were each distributed to either the vehicle group or the treatment group based on random blood glucose and body weight. There was a total of 5 groups with 8 mice for each, and treatments for the groups were as follows: subcutaneous injection of vehicle; subcutaneous injection of insulin aspart (0.36 U/kg); subcutaneous injection of a pharmaceutical composition comprising insulin degludec and insulin aspart, the doses of insulin degludec and insulin aspart being 0.84 U/kg and 0.36 U/kg, respectively; subcutaneous injection of two pharmaceutical compositions comprising compound 4 (the title compound of Example 4 of the present invention) and insulin aspart, the doses of compound 4 being 0.82 U/kg and 0.64 U/kg, respectively, and the dose of insulin aspart being both 0.36 U/kg upon injection of the two compositions, wherein the vehicle contained: 19.6 mg/mL glycerol, 1.5 mg/mL phenol, 1.72 mg/mL m-cresol and 55 μg/mL zinc ions, with a pH value of 7.6.

Pre-mixed solutions of compound 4 and insulin aspart were each dissolved in the vehicle to an administration concentration of 0.072 U/mL (based on the concentration of insulin aspart in the pre-mixture), and the administration volume was 5 mL/kg (i.e., 50 μL/10 g body weight). The administration was performed once by subcutaneous injection (s.c.) at back of the neck. The administration was performed at about 16:00 (time 0), and during the treatment, the mice were fasted but had free access to water, and the blood glucose of the mice was evaluated at times 0.5 h, 1 h, 2 h, 3 h, 6 h and 15 h after the administration.

The tail of each mouse was cleaned with an alcohol cotton ball, and blood drops were collected from the tail using a disposable blood collection needle and measured with a glucometer and accompanying testing strips (Roche). The dose-response curve of blood glucose versus time was plotted. In order to illustrate the effect of the pre-mixed insulins disclosed herein on blood glucose, the area under the blood glucose-time curve (AUC) from time 0 to the monitoring endpoint was calculated for each individual dose-response curve. The smaller the AUC value, the better the hypoglycemic effect, and the better the drug effect.

Figure 13A:
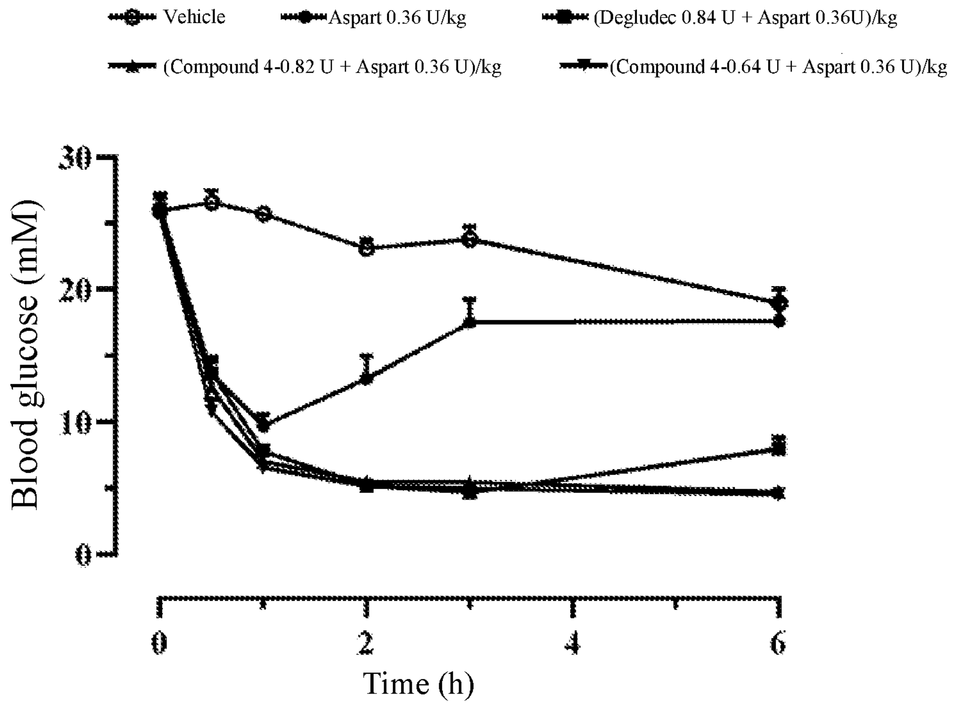
FIG. 13*a* shows the hypoglycemic effect of insulin aspart, a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).
Figure 13B:
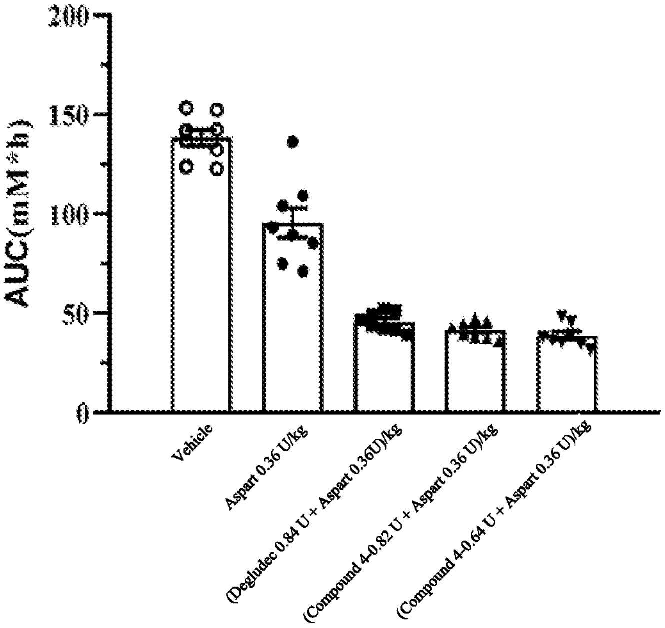
FIG. 13*b* shows, in correspondence with FIG. 13*a*, the AUC of the hypoglycemic effect of insulin aspart, a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).

FIGS. 13*a*-13*b* show that after administration, the pharmaceutical composition comprising the acylated insulin disclosed herein and insulin aspart has a surprisingly increased hypoglycemic effect in mice with type 1 diabetes (T1DM) relative to the pharmaceutical composition comprising insulin degludec and insulin aspart, and it can still achieve a better or comparable hypoglycemic effect when the dose ratio of compound 4 to insulin aspart is less than that of insulin degludec to insulin aspart.

Example 25

By procedures similar to those described in Example 24, the regulatory effect of a composition comprising an acylated insulin disclosed herein and insulin aspart on blood glucose (BG) in C57/6J mice with streptozotocin (STZ)-induced type 1 diabetes (T1DM) was tested.

Before the start of the experiment on the day, the mice were detected for random blood glucose and weighed. Mice were each distributed to either the vehicle group or the treatment group based on random blood glucose and body weight. There was a total of 7 groups with 8 mice for each, and treatments for the groups were as follows: subcutaneous injection of vehicle; subcutaneous injection of insulin aspart (3 U/kg); subcutaneous injection of a pharmaceutical composition comprising insulin degludec and insulin aspart, the doses of insulin degludec and insulin aspart being 7 U/kg and 3 U/kg, respectively; subcutaneous injection of four pharmaceutical compositions comprising compound 4 and insulin aspart, the doses of compound 4 being 6.79 U/kg, 5.34 U/kg, 3.84 U/kg and 2.39 U/kg, respectively, and the dose of aspart being all 3 U/kg upon injection of the four compositions, wherein the vehicle contained: 19.6 mg/mL glycerol, 1.5 mg/mL phenol, 1.72 mg/mL m-cresol and 55 μg/mL zinc ions, with a pH value of 7.6.

Pre-mixed solutions of compound 4 and insulin aspart were each dissolved in the vehicle to an administration concentration of 0.6 U/mL (based on the concentration of insulin aspart in the pre-mixture), and the administration volume was 5 mL/kg (i.e., 50 μL/10 g body weight). The administration was performed by subcutaneous injection (s.c.) at back of the neck. The administration was performed daily at about 17:00 (time 0) for 10 consecutive days, and during the treatment, mice had free access to food and water. The mice were evaluated for blood glucose before the fourth, the eighth and the tenth administrations (0 h) and for random blood glucose at times 1 h after the fourth, the eighth and the tenth administrations, and blood glucose before the eighth administration (0 h) and random blood glucose at times 0.5 h, 1 h, 1.5 h, 2 h, 3 h, 4 h, 5 h, 6 h, 16 h and 24 h after this administration was measured. Mice were fasted for 1 h after the last administration and then subjected to blood collection from the eye orbit, and the percentage of glycated hemoglobin (Hb1Ac) in the whole blood was measured.

The tail of each mouse was cleaned with an alcohol cotton ball, and blood drops were collected from the tail using a disposable blood collection needle and measured with a glucometer and accompanying testing strips (Roche). The dose-response curve of blood glucose versus time after the eighth administration was plotted. In order to illustrate the effect of the pre-mixed insulins disclosed herein on blood glucose, the area under the blood glucose-time curve (AUC) from time 0 to the monitoring endpoint was calculated for each individual dose-response curve after the eighth administration. The smaller the AUC value, the better the hypoglycemic effect, and the better the drug effect.

FIGS. 14*a*-17 show that after administration, the pharmaceutical compositions comprising the acylated insulin disclosed herein and insulin aspart have surprisingly increased hypoglycemic effect in mice with type 1 diabetes (T1DM) and also superior cumulative hypoglycemic effect relative to the pharmaceutical composition comprising insulin degludec and insulin aspart.

Figure 14A:
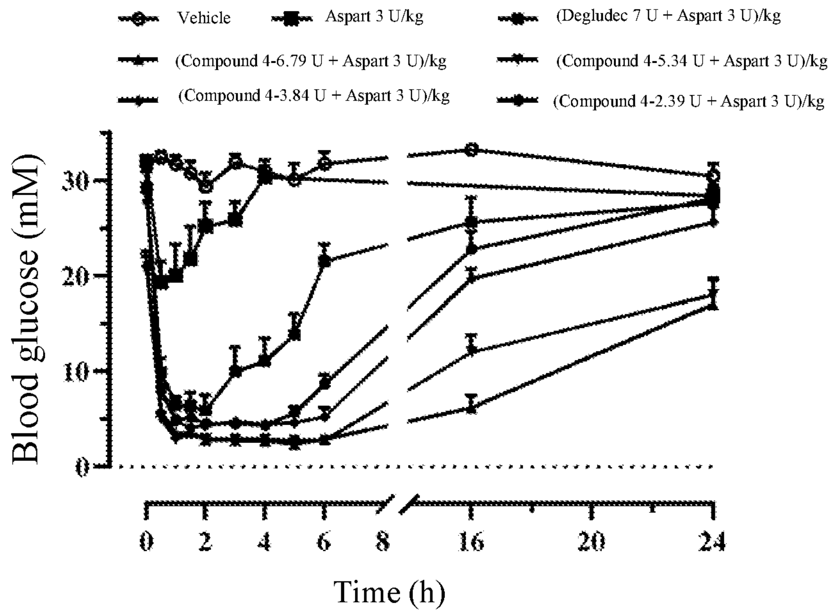
FIG. 14*a* shows the hypoglycemic effect of insulin aspart, a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).
Figure 14B:
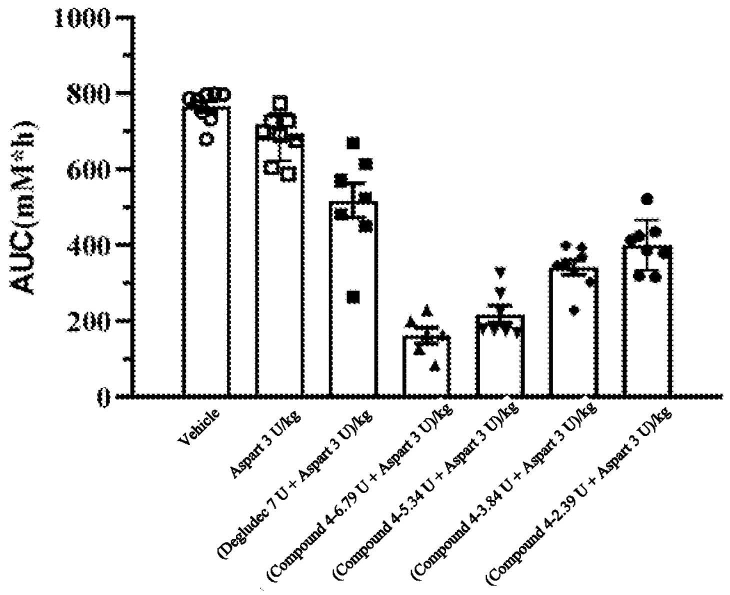
FIG. 14*b* shows, in correspondence with FIG. 14*a*, the AUC of the hypoglycemic effect of insulin aspart, a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).

Specifically, FIGS. 14*a* and 14*b* show that after administration, the compositions comprising the acylated insulin disclosed herein and insulin aspart have surprisingly increased hypoglycemic effect in mice with type 1 diabetes (T1DM) relative to the pharmaceutical composition comprising insulin degludec and insulin aspart, and it can still achieve a better hypoglycemic effect when the dose ratio of compound 4 to insulin aspart is far less than that of insulin degludec to insulin aspart.

Figure 15A:
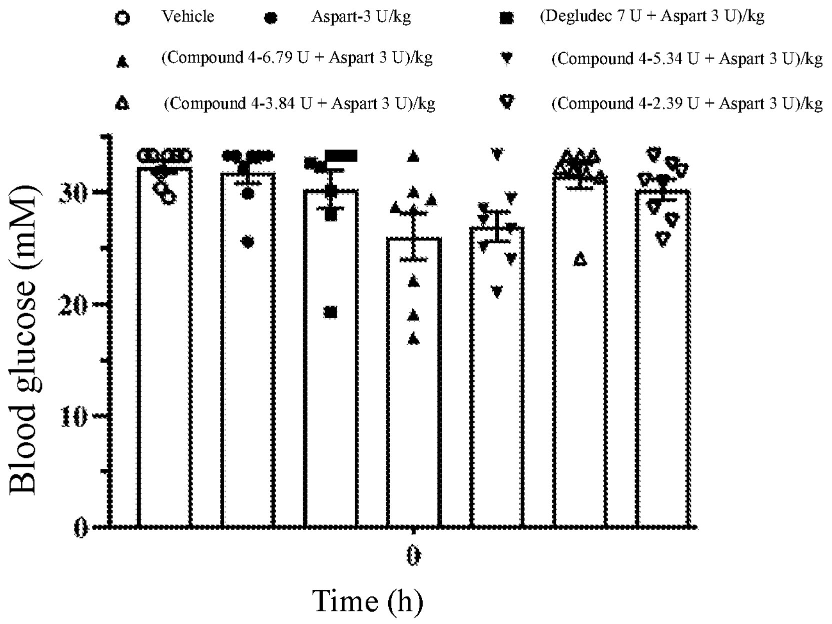
FIG. 15*a* shows the blood glucose of C57/6J mice with STZ-induced type 1 diabetes (T1DM) before the fourth administration of insulin aspart, a pharmaceutical composition comprising dual insulin components of insulin degludec and insulin aspart, pharmaceutical compositions comprising dual insulin components of an acylated insulin disclosed herein and insulin aspart, and vehicle.
Figure 15B:
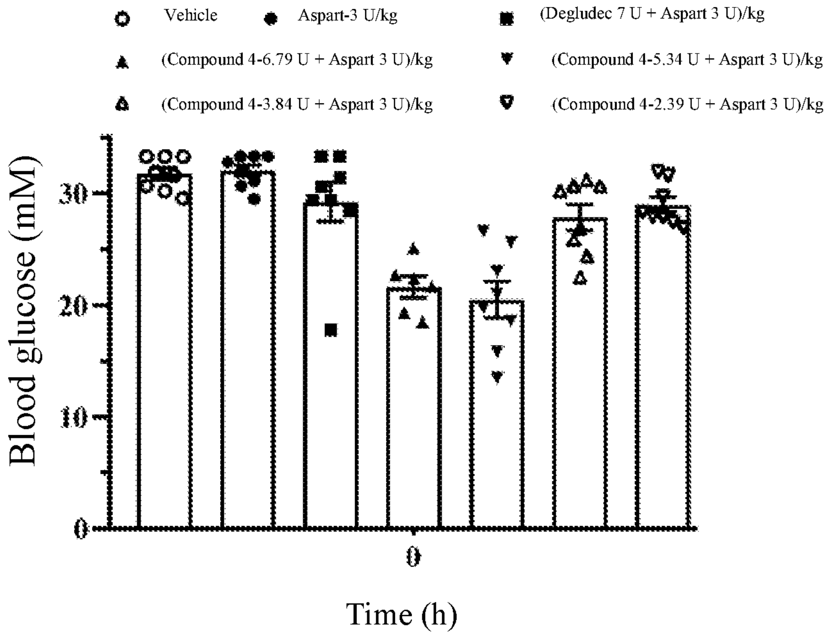
FIG. 15*b* shows the blood glucose of C57/6J mice with STZ-induced type 1 diabetes (T1DM) before the eighth administration of insulin aspart, a pharmaceutical composition comprising dual insulin components of insulin degludec and insulin aspart, pharmaceutical compositions comprising dual insulin components of an acylated insulin disclosed herein and insulin aspart, and vehicle.
Figure 15C:
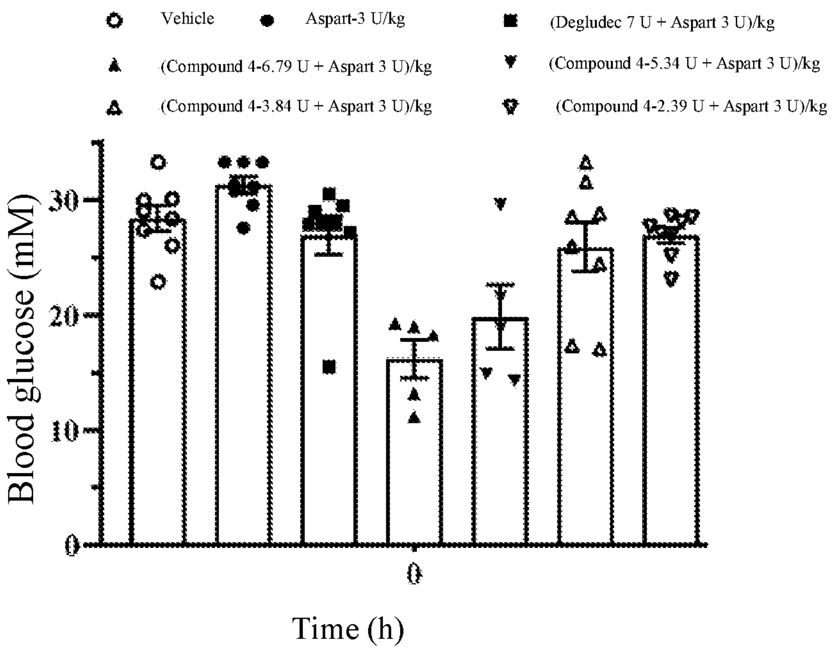
FIG. 15*c* shows the blood glucose of C57/6J mice with STZ-induced type 1 diabetes (T1DM) before the tenth administration of insulin aspart, a pharmaceutical composition comprising dual insulin components of insulin degludec and insulin aspart, pharmaceutical compositions comprising dual insulin components of an acylated insulin disclosed herein and insulin aspart, and vehicle.

FIGS. 15*a*-15*c* show the blood glucose levels of mice in each administration group before the fourth, the eighth and the tenth administrations (0 h), respectively, indicating that the pharmaceutical compositions comprising the acylated insulin disclosed herein and insulin aspart have better drug effect and more excellent cumulative hypoglycemic effect relative to the pharmaceutical composition comprising insulin degludec and insulin aspart.

Figure 16A:
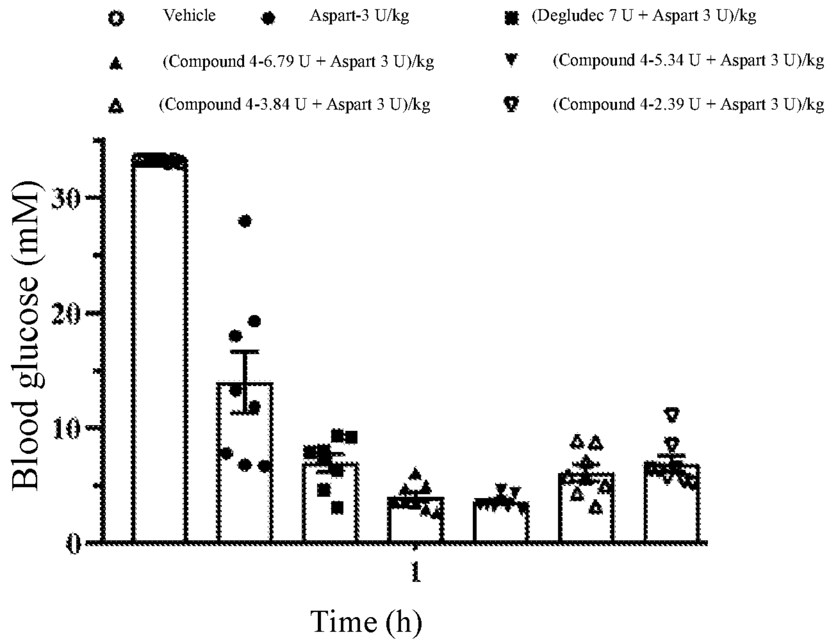
FIG. 16*a* shows the blood glucose of C57/6J mice with STZ-induced type 1 diabetes (T1DM) 1 h after the fourth administration of insulin aspart, a pharmaceutical composition comprising dual insulin components of insulin degludec and insulin aspart, pharmaceutical compositions comprising dual insulin components of an acylated insulin disclosed herein and insulin aspart, and vehicle.
Figure 16B:
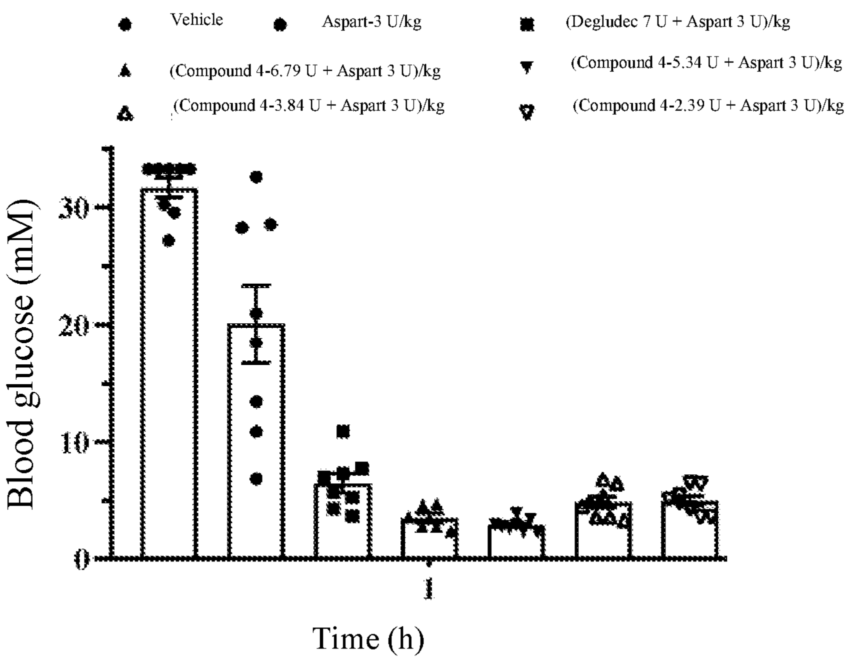
FIG. 16*b* shows the blood glucose of C57/6J mice with STZ-induced type 1 diabetes (T1DM) 1 h after the eighth administration of insulin aspart, a pharmaceutical composition comprising dual insulin components of insulin degludec and insulin aspart, pharmaceutical compositions comprising dual insulin components of an acylated insulin disclosed herein and insulin aspart, and vehicle.
Figure 16C:
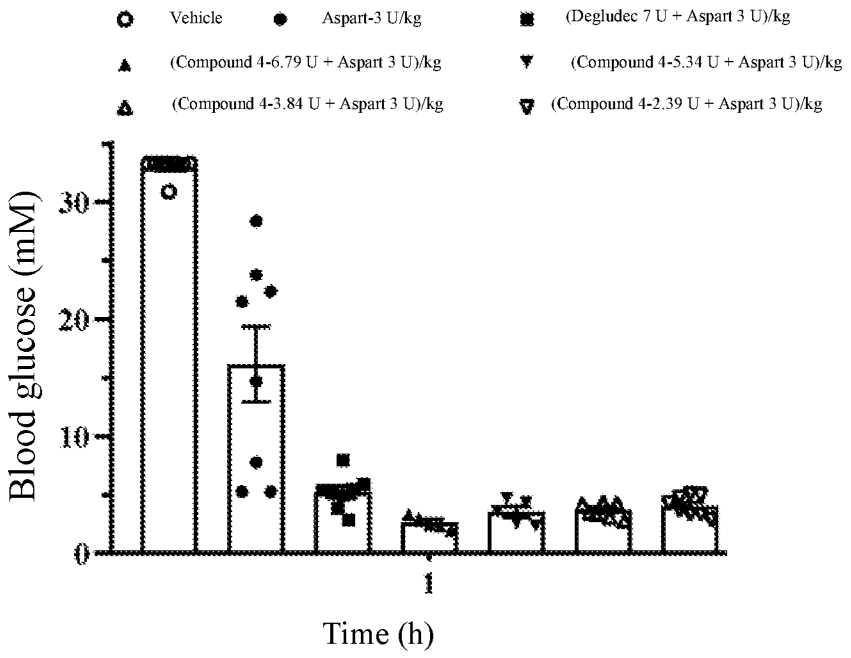
FIG. 16*c* shows the blood glucose of C57/6J mice with STZ-induced type 1 diabetes (T1DM) 1 h after the tenth administration of insulin aspart, a pharmaceutical composition comprising dual insulin components of insulin degludec and insulin aspart, pharmaceutical compositions comprising dual insulin components of an acylated insulin disclosed herein and insulin aspart, and vehicle.

FIGS. 16*a*-16*c* show the blood glucose levels of mice at 1 h after the fourth, the eighth and the tenth administrations, respectively, indicating that the pharmaceutical compositions comprising the acylated insulin disclosed herein and insulin aspart have better drug effect and more excellent cumulative hypoglycemic effect relative to the pharmaceutical composition comprising insulin degludec and insulin aspart.

Figure 17:
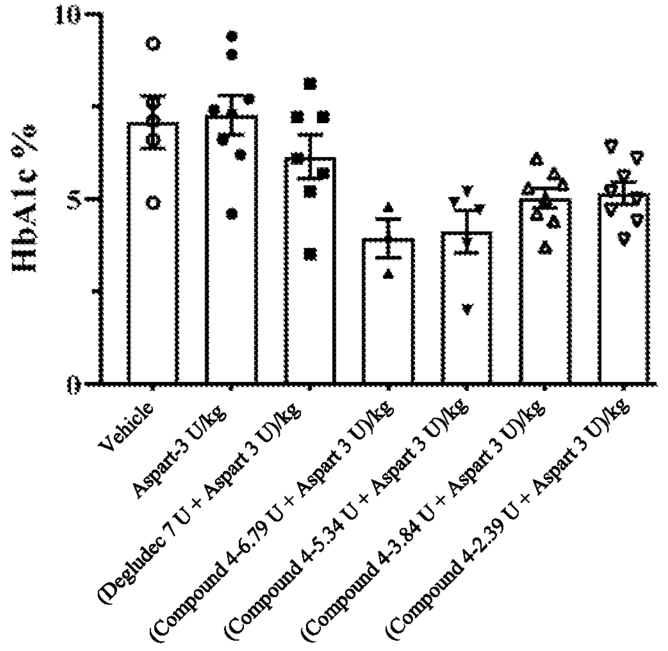
FIG. 17 shows the HbA1c-reducing effect of insulin aspart, a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).

FIG. 17 shows that after administration, the compositions comprising the acylated insulin disclosed herein and insulin aspart have better Hb1Ac-reducing effect relative to the pharmaceutical composition comprising insulin degludec and insulin aspart, and it can still achieve better Hb1Ac-reducing effect when the dose ratio of compound 4 to insulin aspart is far less than that of insulin degludec to insulin aspart.

Example 26

This experiment was intended to determine the chemical stability of the acylated insulin formulations disclosed herein.

Acylated Insulin Formulations

Compound 4 was dissolved in 0.1% NaOH solution to a final concentration of 4.8 mM (with a pH value of about 10-11), and phenol, m-cresol, zinc acetate, glycerol and sodium chloride were added sequentially according to the amount of each component specified in the following table to produce acylated insulin formulations having a final insulin concentration of 1.2 mM (200 U/mL or 8.46 mg/mL), the content of Zn being expressed as Zn/6 moles of the acylated insulin (abbreviated as "Zn/6 ins").

The chemical stability of the formulations in this example can be shown by the change in the amount of high molecular weight protein (HMWP) after 14 and 20 days of storage at 25° C. and 37° C. relative to day 0, and can also be shown by the change in the amount of related substances measured after 14 and 20 days of storage at 25° C. and 37° C.

Determination of High Molecular Weight Protein (HMWP)

The content of high molecular weight protein (HMWP) was determined on a Waters Xbride BEH 200A (7.8×300 mm, 5 m) column by high performance liquid chromatography (HPLC) (column temperature: 30° C.; sample cell temperature: 5° C.; mobile phase: 600 mL of 0.1% arginine solution, 150 mL of glacial acetic acid and 250 mL of acetonitrile; flow rate: 0.5 mL/min). The detection wavelength was 276 nm, and the sample volume was 10 μL. Table 3 shows the increase in the amount of HMWP at 25° C. and 37° C. on day 14 and day 20 relative to day 0.

TABLE 3

| 1.2 mM compound 4 10 mM m-cresol 17 mg/mL glycerol pH 7.4 | 25° C. Increase in the amount of HMWP on day 14 relative to day 0 (%) | 25° C. Increase in the amount of HMWP on day 20 relative to day 0 (%) | 37° C. Increase in the amount of HMWP on day 14 relative to day 0 (%) | 37° C. Increase in the amount of HMWP on day 20 relative to day 0 (%) |
|---|---|---|---|---|
| 30 mM phenol + 5.5Zn/6 ins + 10 mM NaCl | 0.06 | 0.13 | 0.37 | 0.57 |
| 30 mM phenol + 6.5Zn/6 ins + 10 mM NaCl | 0.03 | 0.07 | 0.2 | 0.35 |
| 30 mM phenol + 5.5Zn/6 ins + 30 mM NaCl | 0.05 | 0.07 | 0.34 | 0.56 |

TABLE 3-continued

| 1.2 mM compound 4 10 mM m-cresol 17 mg/mL glycerol pH 7.4 | 25° C. Increase in the amount of HMWP on day 14 relative to day 0 (%) | 25° C. Increase in the amount of HMWP on day 20 relative to day 0 (%) | 37° C. Increase in the amount of HMWP on day 14 relative to day 0 (%) | 37° C. Increase in the amount of HMWP on day 20 relative to day 0 (%) |
|---|---|---|---|---|
| 30 mM phenol + 6.5Zn/6 ins + 30 mM NaCl | 0.03 | 0.04 | 0.16 | 0.28 |
| 60 mM phenol + 5.5Zn/6 ins + 10 mM NaCl | 0.05 | 0.09 | 0.41 | 0.66 |
| 60 mM phenol + 6.5Zn/6 ins + 10 mM NaCl | 0.06 | 0.06 | 0.30 | 0.49 |
| 60 mM phenol + 5.5Zn/6 ins + 30 mM NaCl | 0.08 | 0.08 | 0.36 | 0.56 |
| 60 mM phenol + 6.5Zn/6 ins + 30 mM NaCl | 0.04 | 0.08 | 0.24 | 0.43 |
| 45 mM phenol + 6.0Zn/6 ins + 20 mM NaCl | 0.04 | 0.06 | 0.28 | 0.42 |

It can be seen from the above table that the amount of HMWP in the acylated insulin formulations disclosed herein increases very slowly with time, suggesting that the above acylated insulin formulations all have excellent chemical stability. In particular, when the content of Zn is 6.5 Zn/6 ins, the amount of mHMWP increases more slowly than when the Zn content is 5.5 Zn/6 ins.

Determination of the Amount of Related Substances

The content of insulin related substances was determined on a Waters Kromasil 3eA-5 μm-C8 (4.6×250 mm) column by high performance liquid chromatography (HPLC) (column temperature: 40° C.; sample cell temperature: room temperature; flow rate of elution phase: 1.0 mL/min). Elution was performed with a mobile phase consisting of:

phase A: 0.1 M anhydrous sodium sulfate, 0.1 M sodium dihydrogen phosphate dihydrate, and 10% acetonitrile (v/v), with pH adjusted to 5.0 with NadH; and phase B: 50% acetonitrile (v/v).

Gradient: a linear change from 45%/55% A/B to 35%/65% A/B from 0 m to 45 m, a linear change to 20%/80% A/B from 45 min to 50 min, an isocratic gradient of 20%/80% A/B from 50 m3 to 60 min, a linear change to 45%/55% A/B from 60 m to 60.1 m, and an isocratic gradient of 45%/55% A/B from 60.01 min to 70 min.

Table 4 shows the increase in the amount of the related substances at 37° C. on day 14 and day 20 relative to day 0.

TABLE 4

| 1.2 mM compound 4 10 mM m-cresol 17 mg/mL glycerol pH 7.4 | 37° C. Increase in the amount of the related substances on day 14 relative to day 0 (%) | 37° C. Increase in the amount of the related substances on day 20 relative to day 0 (%) |
|---|---|---|
| 30 mM phenol + 5.5Zn/6 ins + 10 mM NaCl | 1.49 | 2.46 |
| 30 mM phenol + 6.5Zn/6 ins + 10 mM NaCl | 1.61 | 2.79 |
| 30 mM phenol + 5.5Zn/6 ins + 30 mM NaCl | 1.55 | 2.4 |
| 30 mM phenol + 6.5Zn/6 ins + 30 mM NaCl | 1.58 | 2.63 |
| 60 mM phenol + 5.5Zn/6 ins + 10 mM NaCl | 1.74 | 2.71 |
| 60 mM phenol + 6.5Zn/6 ins + 10 mM NaCl | 1.69 | 2.94 |

TABLE 4-continued

| 1.2 mM compound 4 10 mM m-cresol 17 mg/mL glycerol pH 7.4 | 37° C. Increase in the amount of the related substances on day 14 relative to day 0 (%) | 37° C. Increase in the amount of the related substances on day 20 relative to day 0 (%) |
|---|---|---|
| 60 mM phenol + 5.5Zn/6 ins + 30 mM NaCl | 1.52 | 2.58 |
| 60 mM phenol + 6.5Zn/6 ins + 30 mM NaCl | 1.56 | 2.8 |
| 45 mM phenol + 6.0Zn/6 ins + 20 mM NaCl | 1.46 | 2.58 |

It can be seen from the above table that the amount of related substances in the acylated insulin formulations disclosed herein also increases very slowly with time, suggesting that the acylated insulin formulations above are very stable.

Example 27

This experiment was intended to determine the chemical stability of the acylated insulin formulations disclosed herein. The acylated insulin formulations in Tables 5-7 were formulated, according to the amount of each component specified in Tables 5-7 below, by procedures similar to those described in Example 26. Besides, change in the amount of HMWP and related substances was determined by procedures similar to those described in Example 26. Tables 5-7 below show the change in the amount of HMWP and related substances in the acylated insulin formulations of different formulas.

TABLE 5

| 2.1 mM compound 4 60 mM phenol 10 mM m-cresol 20 mM NaCl 15 mg/mL glycerol pH 7.4 | 37° C. Increase in the amount of HMWP on day 26 relative to day 0 (%) | 37° C. Increase in the amount of HMWP on day 65 relative to day 0 (%) | 37° C. Rate of increase per day in amount of HMWP for 65 days of storage (%) |
|---|---|---|---|
| 2.2Zn/6ins | 0.98 | 2.18 | 0.032 |
| 2.5Zn/6ins | 0.99 | 2.42 | 0.037 |
| 3Zn/6ins | 0.79 | 1.68 | 0.026 |
| 4.5Zn/6ins | 0.43 | 1.2 | 0.018 |

TABLE 6

| 2.1 mM compound 4 60 mM phenol 10 mM m-cresol 15 mg/mL glycerol pH 7.4 | 37° C. Increase in the amount of HMWP on day 26 relative to day 0 (%) | 37° C. Increase in the amount of HMWP on day 65 relative to day 0 (%) | 37° C. Rate of increase per day in amount of HMWP for 65 days of storage (%) |
|---|---|---|---|
| 10 mM $Na_2HPO_4$ + 2.2Zn/6ins | 0.88 | 1.84 | 0.028 |
| 10 mM $Na_2HPO_4$ + 4.5Zn/6ins | 0.20 | 0.55 | 0.008 |
| 30 mM $Na_2HPO_4$ + 2.2Zn/6ins | 0.67 | 1.47 | 0.023 |
| 30 mM $Na_2HPO_4$ + 4.5Zn/6ins | 0.27 | 0.61 | 0.009 |
| 2.2Zn/6ins | 0.96 | 2.16 | 0.033 |
| 4.5Zn/6ins | 0.46 | 1.33 | 0.020 |

TABLE 7

| 0.6 mM compound 2 60 mM phenol 15 mg/mL glycerol 5 mM sodium dihydrogen phosphate 10 mM NaCl pH 7.6 | 37° C. Increase in the amount of HMWP on day 30 relative to day 0 (%) | 37° C. Rate of increase per day in amount of HMWP for 30 days of storage (%) | 37° C. Increase in the amount of the related substances on day 30 relative to day 0 (%) | 37° C. Rate of increase per day in amount of related substances for 30 days of storage (%) |
|---|---|---|---|---|
| 5.5Zn/6ins | 0.45 | 0.0153 | 1.91 | 0.0637 |
| 6.5Zn/6ins | 0.42 | 0.0140 | 1.50 | 0.0500 |
| 7Zn/6ins | 0.44 | 0.0147 | 1.58 | 0.0527 |
| 7.5Zn/6ins | 0.51 | 0.0170 | 1.75 | 0.0583 |

It can be seen from the above table that the amount of HMWP and that of the related substances in the above acylated insulin formulations disclosed herein increase relatively slowly with time, and the amount of HMWP and that of the related substances increase more slowly especially when the content of Zn ions increases or $Na_2HPO_4$ is added, suggesting that the acylated insulin formulations obtained by the present invention all have good chemical stability.

Example 28

This experiment was intended to determine the chemical stability of the acylated insulin formulations disclosed herein. The acylated insulin formulations in Table 8 were formulated, according to the amount of each component specified in Table 8 below, by procedures similar to those described in Example 26. Besides, change in the amount of HMWP and related substances was determined by procedures similar to those described in Example 26. The table below shows the change in the amount of HMWP and related substances in the acylated insulin formulations of different formulas.

TABLE 8

| 60 mM phenol 4.5Zn/6 ins 15 mg/mL glycerol 5 mM sodium dihydrogen phosphate 10 mM m-cresol 10 mM NaCl | 37° C. Increase in the amount of HMWP on day 14 relative to day 0 (%) | 37° C. Increase in the amount of the related substances after 14 days of storage relative to day 0 (%) |
|---|---|---|
| 0.6 mM (100 U) compound 4 | 0.77 | 1.62 |
| 2.1 mM (350 U) compound 4 | 0.57 | 1.08 |
| 3.0 mM (500 U) compound 4 | 0.53 | 1.03 |
| 4.2 mM (700 U) compound 4 | 0.45 | 1.29 |

It can be seen from the above table that the amount of HMWP and that of the related substances in the above acylated insulin formulations disclosed herein increase relatively slowly with time, suggesting that the acylated insulin formulations obtained by the present invention all have good chemical stability.

Example 29

Pharmacodynamic Study in Rats with Streptozotocin (STZ)-Induced Type 1 Diabetes (T1DM) SD rats (half female and half male) aged 8 weeks and weighed 170-250 g were housed in appropriately sized feeding cages (4 rats/cage) in a barrier environment with free access to standard food and purified water, with environmental conditions controlled at 40%-70% RH and 22-26° C.

After an adaptation period of 4 days, the rats were fasted for 12 h and injected intraperitoneally with streptozotocin (Sigma) solution (10 mg/mL, in 0.1 M citrate buffer) at 60 mg/kg. 4 days and 8 days after the administration of streptozotocin, random blood glucose detection was carried out, and rats with a blood glucose value higher than 20 mmol/L were selected as T1DM model rats for subsequent experiment.

The experiment was started 8 days after molding. The day before the administration, the rats were monitored for baseline blood glucose and weighed. Rats were each distributed to either the vehicle group or the treatment group based on random blood glucose and body weight, and subjected to the following treatments: subcutaneous injection of vehicle, subcutaneous injection of insulin degludec (50 U/kg) or subcutaneous injection of compound 4 (25 U/kg or 40 U/kg), wherein the vehicle contained: 60 mM phenol, 15 mg/mL glycerol, 10 mM m-cresol and 0.585 mg/mL sodium chloride, with a pH value of 7.4.

The acylated insulin was dissolved in the vehicle to an administration concentration of 25 U/mL or 40 U/mL, and the administration volume was 1 mL/kg (i.e., 0.1 mL/100 g body weight). The administration was performed by subcutaneous injection (s.c.) at back of the neck once every other day and was repeated 11 times, and the SD rats had free access to food and water during the experiment. The acylated insulin was administered at about 9:30-10:30 a.m. The blood glucose of rats was monitored at times 3 h, 4 h, 5 h, 6 h, 24 h and 48 h after the first administration, and the blood glucose of rats was monitored at times 4 h, 24 h and 48 h after each of the following administrations.

The dose-response curve of blood glucose versus time was plotted for each single dose of acylated insulin. In order to illustrate the effect of the acylated insulins on blood glucose, the area under the blood glucose-time curve (AUC) from time 0 to the monitoring endpoint was calculated for each individual dose-response curve.

Figure 18A:
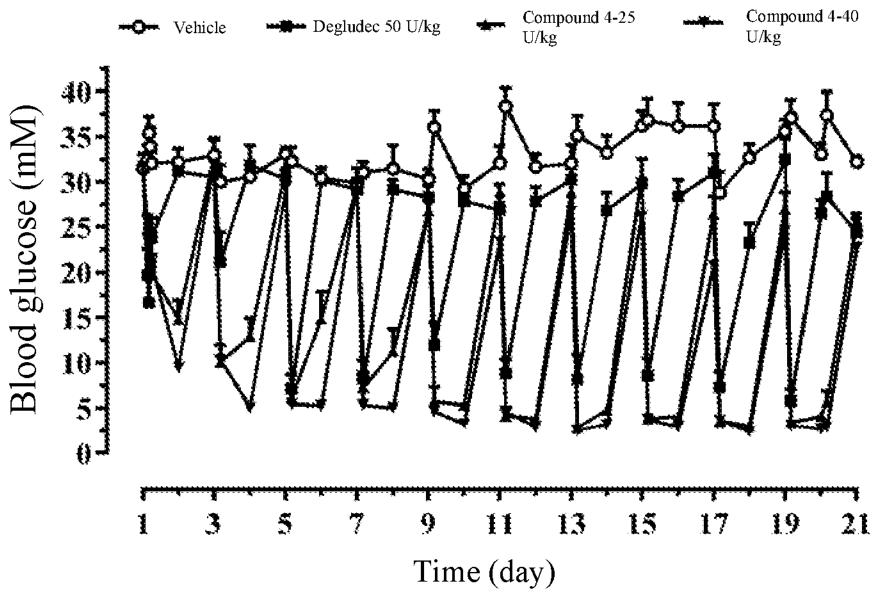
FIG. 18*a* shows the hypoglycemic effect of the compound of Example 4 in the present invention, insulin degludec and vehicle on rats with STZ-induced type 1 diabetes (T1DM).
Figure 18B:
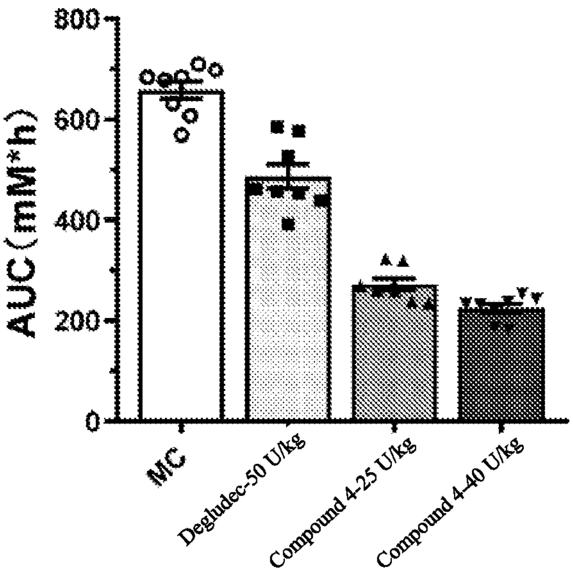
FIG. 18*b* shows, in correspondence with FIG. 18*a*, the AUC of the hypoglycemic effect of the compound of Example 4 in the present invention, insulin degludec and vehicle on rats with STZ-induced type 1 diabetes (T1DM).

As shown in FIGS. 18*a*-18*b*, relative to insulin degludec, the acylated insulin disclosed herein has surprisingly increased hypoglycemic effect in rats with type 1 diabetes (T1DM) after administration, and the hypoglycemic effect of compound 4 is significantly superior to that of insulin degludec.

Example 30

By procedures similar to those described in Example 24, the regulatory effect of a composition comprising an acylated insulin disclosed herein and insulin aspart on blood glucose (BG) in C57/6J mice with streptozotocin (STZ)-induced type 1 diabetes (T1DM) was tested.

Before the start of the experiment on the day, the mice were detected for random blood glucose and weighed. Mice were each distributed to either the vehicle group or the treatment group based on random blood glucose and body weight. There was a total of 8 groups with 9 mice (5 male mice and 4 female mice) for each, and treatments for the groups were as follows: subcutaneous injection of vehicle; subcutaneous injection of a pharmaceutical composition comprising insulin degludec and insulin aspart, the doses of insulin degludec and insulin aspart being 7 U/kg and 3 U/kg, respectively; subcutaneous injection of six pharmaceutical compositions comprising compound 4 (the title compound of Example 4 of the present invention) and insulin aspart, the doses of compound 4 being 1.49 U/kg, 1.99 U/kg, 2.45 U/kg, 2.85 U/kg, 3.43 U/kg and 3.92 U/kg, respectively, and the dose of aspart being all 3 U/kg upon injection of the six pharmaceutical compositions, wherein the vehicle contained: 60 mM phenol, 10 mM m-cresol, 15 mg/mL glycerol and 15 mM $Na_2HPO_4$, with a pH value of 7.6.

Pre-mixed solutions of compound 4 and insulin aspart were each dissolved in the vehicle to an administration concentration of 0.6 U/mL (based on the concentration of insulin aspart in the pre-mixture), and the administration volume was 5 mL/kg (i.e., 50 μL/10 g body weight). The administration was performed by subcutaneous injection (s.c.) at back of the neck. The administration was performed daily at about 16:00 (time 0) for 15 consecutive days, and during the treatment, mice had free access to food and water. The mice were evaluated for random blood glucose before the first, the second, the fifth, the eighth and the fifteenth administrations (0 h) and 1 h after these administrations, and blood glucose before the second, the fifth, the eighth and the fifteenth administrations (0 h) and random blood glucose at times 0.5 h, 1 h, 2 h, 4 h, 6 h, 16 h, 20 h and 24 h after these administrations were measured. Mice were fasted for 2 h after the last administration and then subjected to blood collection from the eye orbit, and the percentage of glycated hemoglobin (Hb1Ac) in the whole blood was measured.

The tail of each mouse was cleaned with an alcohol cotton ball, and blood drops were collected from the tail using a disposable blood collection needle and measured with a glucometer and accompanying testing strips (Roche). The dose-response curve of blood glucose versus time after the fifteenth administration was plotted. In order to illustrate the effect of the pre-mixed insulins disclosed herein on blood glucose, the area under the blood glucose-time curve (AUC) from time 0 to the monitoring endpoint was calculated for each individual dose-response curve after the fifteenth administration. The smaller the AUC value, the better the hypoglycemic effect, and the better the drug effect.

Figure 19A:
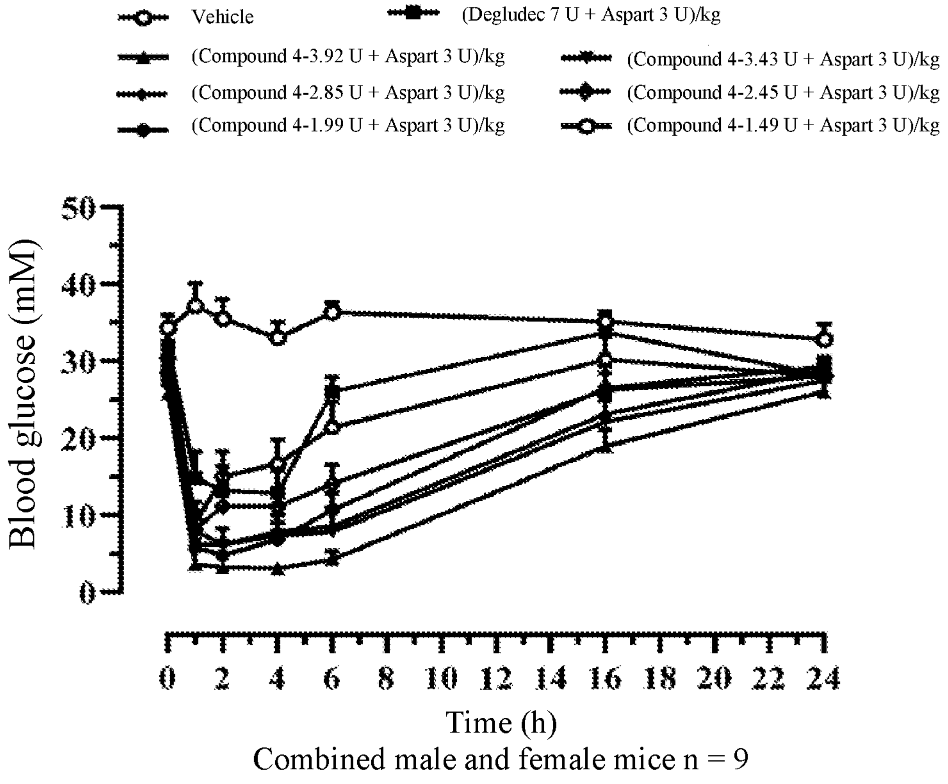
FIG. 19*a* shows the hypoglycemic effect of a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).
Figure 19B:
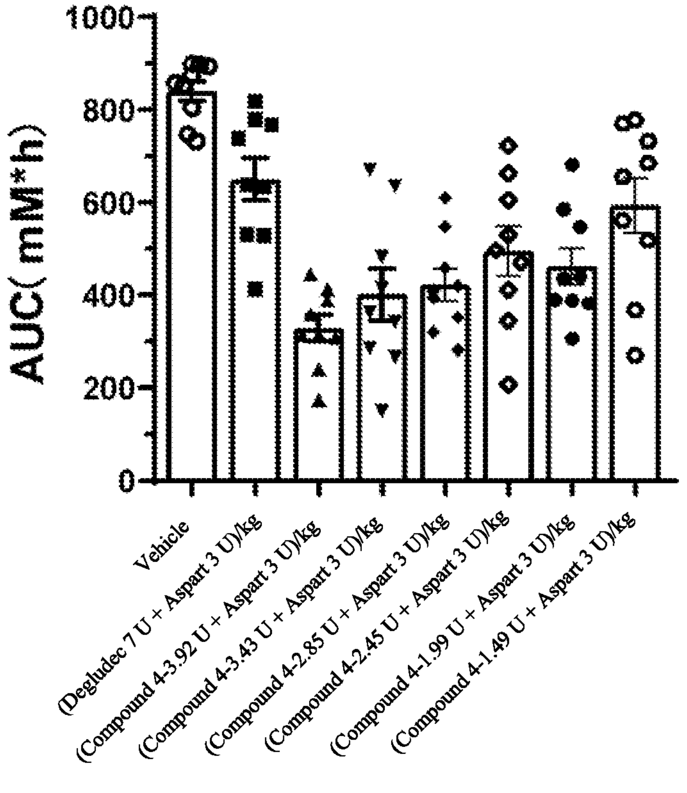
FIG. 19*b* shows, in correspondence with FIG. 19*a*, the AUC of the hypoglycemic effect of a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).

FIGS. 19*a* and 19*b* show that after administration, the compositions comprising the acylated insulin disclosed herein and insulin aspart havesurprisingly increased hypoglycemic effect in mice with type 1 diabetes (T1DM) relative to the pharmaceutical composition comprising insulin degludec and insulin aspart, and it can still achieve better hypoglycemic effect when the dose ratio of compound 4 to insulin aspart is far less than that of insulin degludec to insulin aspart.

Figure 20:
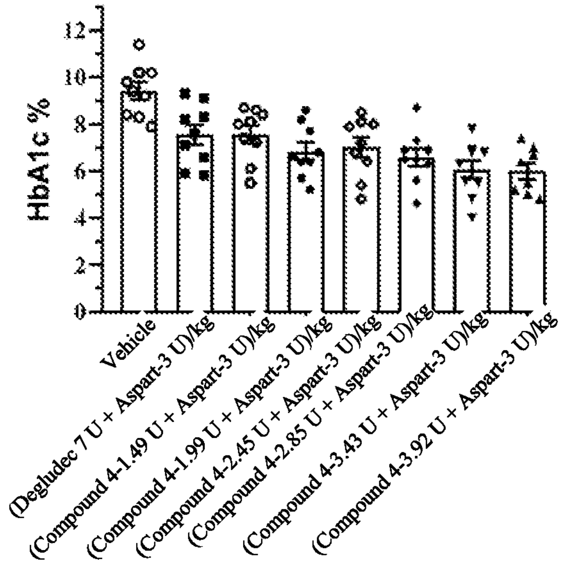
FIG. 20 shows the HbA1c-reducing effect of a pharmaceutical composition comprising dual insulin components of insulin degludec and insulin aspart, pharmaceutical compositions comprising dual insulin components of an acylated insulin disclosed herein and insulin aspart, and vehicle on C57/6J mice with STZ-induced type 1 diabetes (T1DM).

FIG. 20 shows that after administration, the compositions comprising the acylated insulin disclosed herein and insulin aspart have better Hb1Ac-reducing effect relative to the pharmaceutical composition comprising insulin degludec and insulin aspart, and it can still achieve better Hb1Ac-reducing effect when the dose ratio of compound 4 to insulin aspart is far less than that of insulin degludec to insulin aspart.

Example 31

Pharmacodynamic Study in db/db Mice

This study was intended to demonstrate the regulatory effect of a combination comprising an acylated insulin disclosed herein and insulin aspart on blood glucose (BG) in an obese diabetic mouse model (db/db mice) in a diabetic setting.

Male db/db (BKS/Lepr) mice aged 8-9 weeks were housed in appropriately sized feeding cages in a barrier environment with free access to standard food and purified water, with environmental conditions controlled at 40%-60% RH and 22-24° C. After an adaptation period of 1-2 weeks, the mice were used in the experiment.

Before the start of the experiment on the day, the mice were detected for random blood glucose and weighed. Mice were each distributed to either the vehicle group or the treatment group based on random blood glucose and body weight. There was a total of 5 groups with 8 mice for each, and treatments for the groups were as follows: subcutaneous injection of vehicle; subcutaneous injection of a pharmaceutical composition comprising insulin degludec and insulin aspart, the doses of insulin degludec and insulin aspart being 7 U/kg and 3 U/kg, respectively; subcutaneous injection of three pharmaceutical compositions comprising compound 4 (the title compound of Example 4 of the present invention) and insulin aspart, the doses of compound 4 being 2.0 U/kg, 2.4 U/kg and 3.84 U/kg, respectively, and the dose of aspart being all 3 U/kg upon injection of the three pharmaceutical compositions, wherein the vehicle contained: 60 mM phenol, 10 mM m-cresol, 15 mg/mL glycerol and 15 mM $Na_2HPO_4$, with a pH value of 7.6.

The acylated insulins were each dissolved in the vehicle to an administration concentration of 0.6 U/mL, and the administration volume was 5 mL/kg (i.e., 50 μL/10 g body weight). The administration was performed four times by subcutaneous injection (s.c.) at back of the neck. The acylated insulins were administered at about 9:30 a.m. (time 0), and during the treatment, the mice were fasted but had free access to water, and the blood glucose of the mice was evaluated at times 0.5 h, 1 h, 2 h, 3 h, 4 h, 6 h, 8 h, 10 h and 12 h after the administration.

The tail of each mouse was cleaned with an alcohol cotton ball, and blood drops were collected from the tail using a disposable blood collection needle and measured with a glucometer and accompanying testing strips (Roche). The dose-response curve of blood glucose versus time was plotted for each single dose of acylated insulin.

In order to illustrate the effect of the pharmaceutical composition comprising an acylated insulin and insulin aspart disclosed herein on blood glucose, the area under the blood glucose-time curve (AUC) from time 0 to the monitoring endpoint was calculated for each individual dose-response curve. The smaller the AUC value, the better the hypoglycemic effect, and the better the drug effect.

Figure 21A:
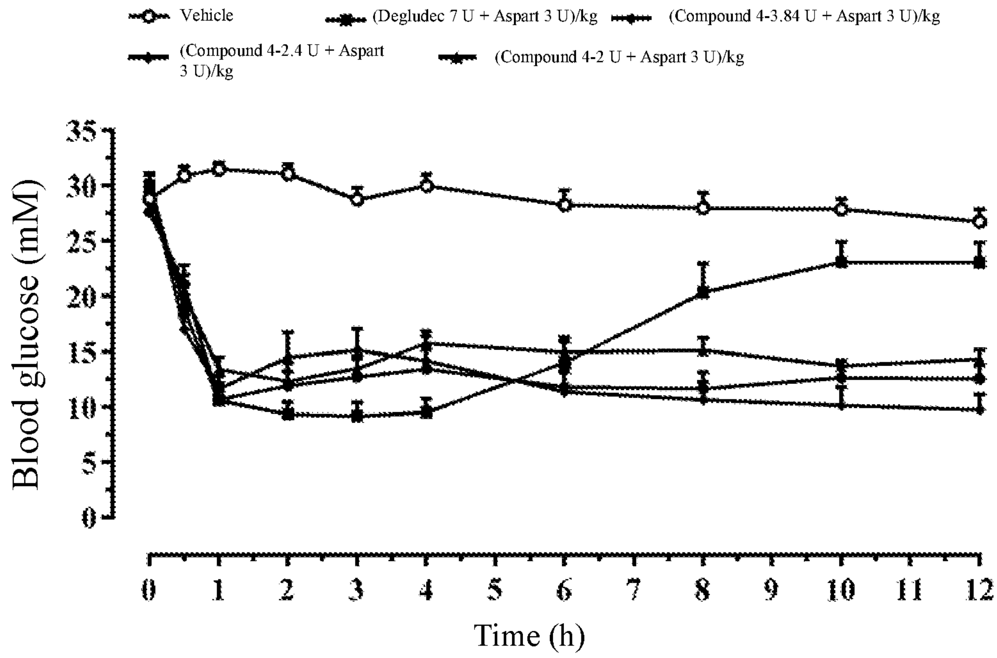
FIG. 21*a* shows the hypoglycemic effect of a pharmaceutical composition comprising dual insulin components of insulin degludec and insulin aspart, pharmaceutical compositions comprising dual insulin components of an acylated insulin disclosed herein and insulin aspart, and vehicle on db/db mice.
Figure 21B:
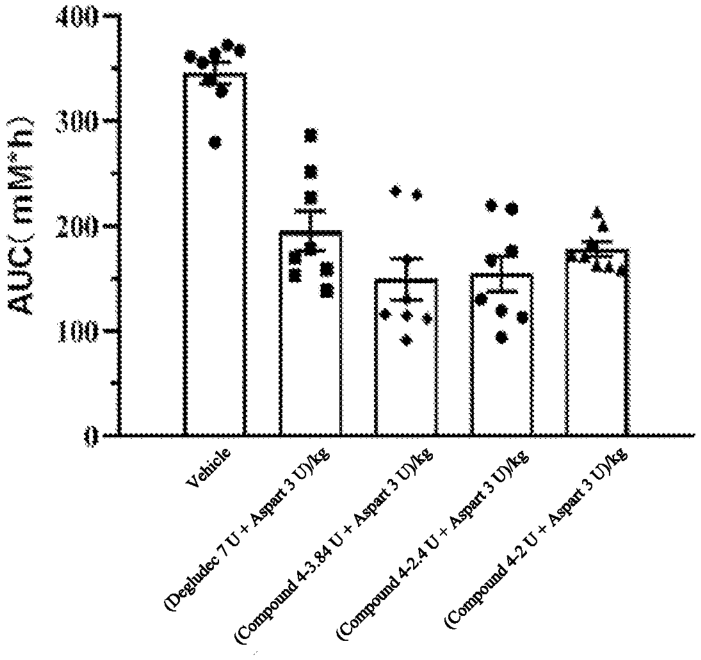
FIG. 21*b* shows, in correspondence with FIG. 21*a*, the AUC of the hypoglycemic effect of a pharmaceutical composition comprising dual insulin components of insulin degludec and insulin aspart, pharmaceutical compositions comprising dual insulin components of an acylated insulin disclosed herein and insulin aspart, and vehicle on db/db mice.
Figure 22A:
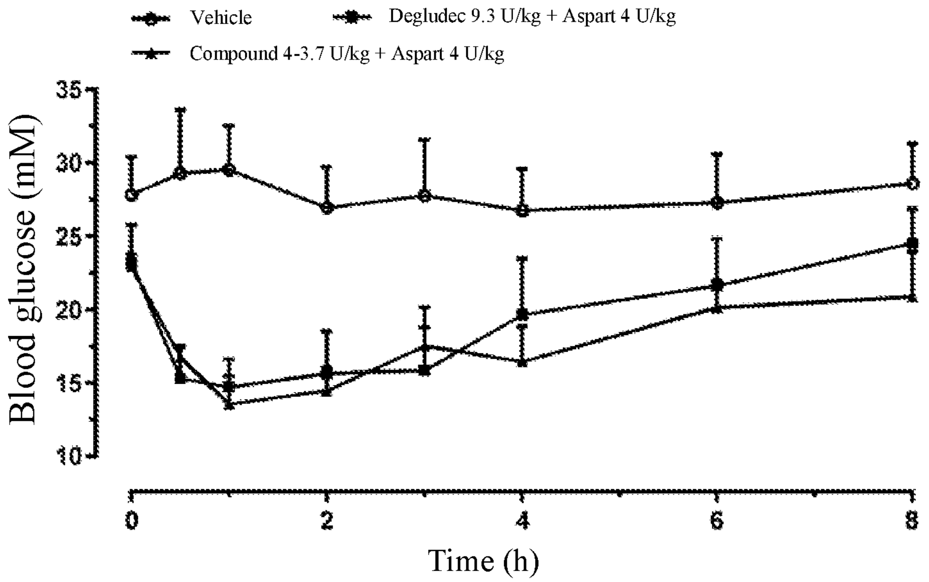
FIG. 22*a* shows the random blood glucose of db/db mice after injection of a pharmaceutical composition comprising dual insulin components of insulin degludec and insulin aspart, a pharmaceutical composition comprising dual insulin components of an acylated insulin disclosed herein and insulin aspart, and vehicle.
Figure 22B:
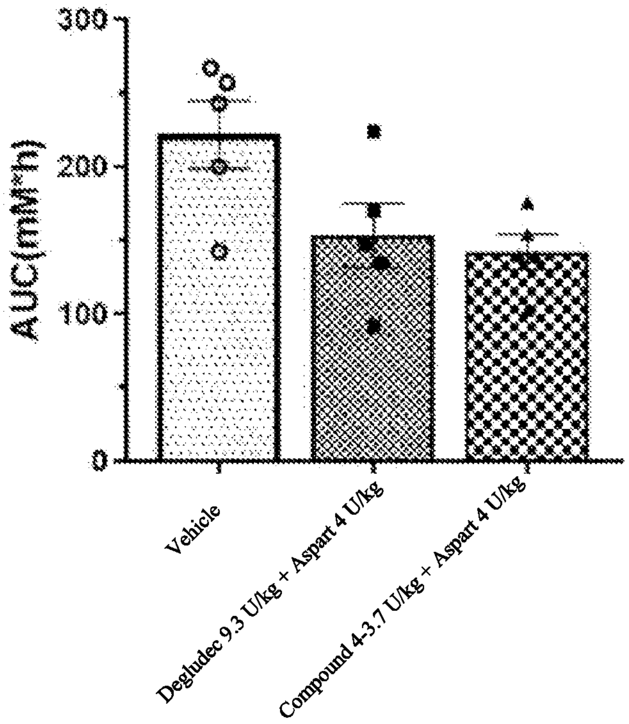
FIG. 22*b* shows, in correspondence with FIG. 22*a*, the AUC of the random blood glucose of db/db mice after injection of a pharmaceutical composition comprising dual insulin components of insulin degludec and insulin aspart, a pharmaceutical composition comprising dual insulin components of an acylated insulin disclosed herein and insulin aspart, and vehicle.
Figure 22C:
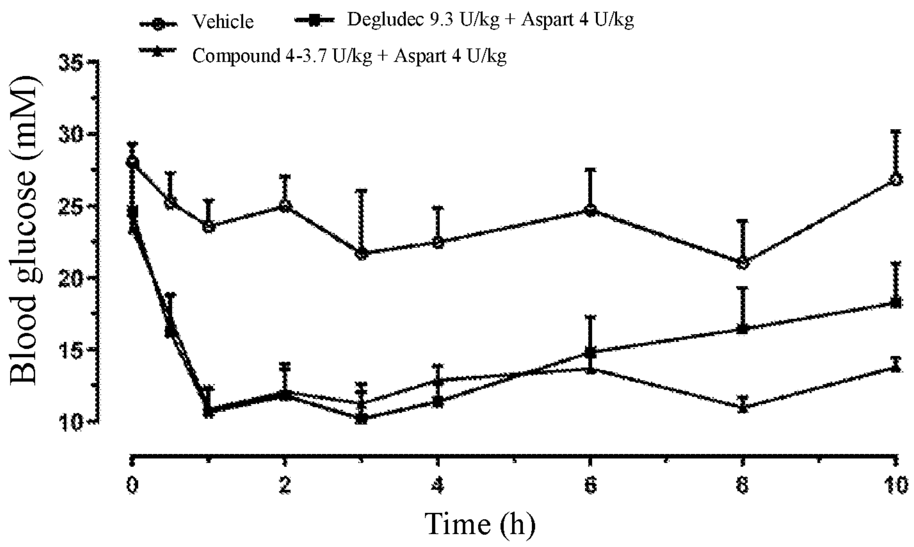
FIG. 22*c* shows the fasting blood glucose of db/db mice after injection of a pharmaceutical composition comprising dual insulin components of insulin degludec and insulin aspart, a pharmaceutical composition comprising dual insulin components of an acylated insulin disclosed herein and insulin aspart, and vehicle.
Figure 22D:
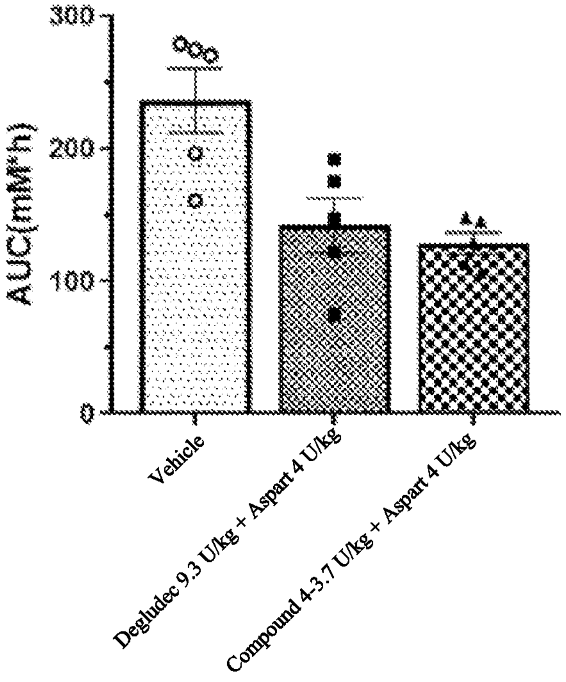
FIG. 22*d* shows, in correspondence with FIG. 22*c*, the AUC of the fasting blood glucose of db/db mice after injection of a pharmaceutical composition comprising dual insulin components of insulin degludec and insulin aspart, a pharmaceutical composition comprising dual insulin components of an acylated insulin disclosed herein and insulin aspart, and vehicle.

FIGS. 21*a* and 21*b* show that after administration, the compositions comprising the acylated insulin disclosed herein and insulin aspart have surprisingly increased hypoglycemic effect in the obese diabetic mouse model (db/db mice) relative to the pharmaceutical composition comprising insulin degludec and insulin aspart, and it can still achieve better hypoglycemic effect when the dose ratio of compound 4 to insulin aspart is far less than that of insulin degludec to insulin aspart.

Example 32

This experiment was intended to determine the chemical stability of the acylated insulin formulations disclosed herein.

Acylated Insulin Formulations

Compound 4 (the title compound of Example 4) was dissolved in 0.03% NaOH solution to a concentration of 2.4 mM, and then the pH was adjusted to 7.4 with 4% NaOH solution. Phenol, m-cresol, glycerol and sodium chloride were mixed well according to the amount of each component specified in the table below and added to the compound 4 solution, and the pH was adjusted to 7.4. Zinc acetate was added to the compound 4 solution in three equal portions according to the amount specified in the table below, and the pH was adjusted to the final value.

Acylated insulin formulations having a final insulin concentration of 1.2 mM (200 U/mL or 8.46 mg/mL) were produced, the content of Zn being expressed as Zn/6 moles of the acylated insulin (abbreviated as "Zn/6 ins").

The chemical stability of the formulations in this example can be shown by the change in the amount of high molecular weight protein (HMWP) after 14 and 21 days of storage at 25° C. and 37° C. relative to day 0, and can also be shown by the change in the amount of related substances measured after 21 days of storage at 37° C.

Determination of high molecular weight protein (HMWP) The content of high molecular weight protein (HMWP) was determined on a Shodex™ PROTEIN KW-802.5 (8.0×300 mm) column by high performance liquid chromatography (HPLC) (column temperature: 30° C.; sample cell temperature: 5° C.; mobile phase: 3 L of 0.1% arginine solution, 750 mL of glacial acetic acid and 1250 mL of acetonitrile; flow rate: 0.5 mL/min). The detection wavelength was 276 nm, and the sample volume was 10 μL. Table 9 shows the increase in the amount of HMWP at 25° C. and 37° C. on day 14 and day 21 relative to day 0.

TABLE 9

| 1.2 mM compound 4<br>10 mM m-cresol<br>17 mg/mL glycerol<br>45 mM phenol<br>6.5Zn/6 ins<br>20 mM NaCl | 25° C.<br>Increase in the amount of HMWP on day 14 relative to day 0 (%) | 25° C.<br>Increase in the amount of HMWP on day 21 relative to day 0 (%) | 37° C.<br>Increase in the amount of HMWP on day 14 relative to day 0 (%) | 37° C.<br>Increase in the amount of HMWP on day 21 relative to day 0 (%) |
|---|---|---|---|---|
| pH 7.0 | 0.03 | 0.07 | 0.27 | 0.45 |
| pH 7.2 | 0.02 | 0.06 | 0.25 | 0.34 |
| pH 7.4 | 0.03 | 0.06 | 0.26 | 0.34 |
| pH 7.6 | 0.01 | 0.06 | 0.25 | 0.35 |
| pH 8.0 | 0.06 | 0.12 | 0.44 | 0.79 |

It can be seen from the above table that within the above pH range, the amount of HMWP in the acylated insulin formulations disclosed herein increases very slowly with time, suggesting that the acylated insulin formulations all have excellent chemical stability within the above pH range.

Determination of the Amount of Related Substances

The content of insulin related substances was determined on a Waters Kromasil 100A-3.5 μm-C8 (4.6×250 mm) column by high performance liquid chromatography (HPLC) (column temperature: 40° C.; sample cell temperature: 10° C.; flow rate of elution phase: 1.0 mL/min). Elution was performed with a mobile phase consisting of:

phase A: 0.1 M anhydrous sodium sulfate, 0.1 M sodium dihydrogen phosphate dihydrate, and 10% acetonitrile (v/v), with pH adjusted to 3.0 with concentrated phosphoric acid; and phase B: 60% acetonitrile (v/v).

Gradient: an isocratic gradient of 41.3%/58.7% A/B from 0 min to 40 min, a linear change to 0%/100% A/B from 40 min to 50 min, a linear change to 41.3%/58.7% A/B from 50 min to 51 min, and an isocratic gradient of 41.3%/58.7% A/B from 51 min to 65 min. Table 10 shows the increase in the amount of the related substances at 37° C. on day 21 relative to day 0.

TABLE 10

| 1.2 mM compound 4<br>10 mM m-cresol<br>17 mg/mL glycerol<br>45 mM phenol<br>6.5Zn/6 ins<br>20 mM NaCl | 37° C.<br>Increase in the amount of the related substances on day 21 relative to day 0 (%) |
|---|---|
| pH 7.0 | 2.43 |
| pH 7.2 | 2.44 |
| pH 7.4 | 2.22 |
| pH 7.6 | 2.29 |
| pH 8.0 | 3.34 |

It can be seen from the above table that within the above pH range, the amount of related substances in the acylated insulin formulations disclosed herein also changes very slowly with time, and the above acylated insulin formulations disclosed herein all have excellent chemical stability.

Example 33

This experiment was intended to determine the chemical stability of the acylated insulin formulations disclosed herein. The acylated insulin formulations in Tables 11 and 12 were formulated, according to the amount of each component specified in Tables 11 and 12 below, by procedures similar to those described in Example 32. Besides, change in the amount of HMWP and related substances was determined by procedures similar to those described in Example 32.

Tables 11 and 12 below show the change in the amount of HMWP and related substances in the acylated insulin formulations of different formulas.

TABLE 11

| 10 mM m-cresol 17 mg/mL glycerol 45 mM phenol 6.5Zn/6 ins 20 mM NaCl pH 7.4 | 25° C. Increase in the amount of HMWP on day 22 relative to day 0 (%) | 25° C. Increase in the amount of HMWP on day 42 relative to day 0 (%) | 37° C. Increase in the amount of HMWP on day 22 relative to day 0 (%) | 37° C. Increase in the amount of HMWP on day 42 relative to day 0 (%) |
|---|---|---|---|---|
| 100 U compound 4 | 0.06 | 0.13 | 0.25 | 0.75 |
| 200 U compound 4 | 0.03 | 0.07 | 0.18 | 0.55 |

TABLE 12

| 10 mM m-cresol 17 mg/mL glycerol 45 mM phenol 6.5Zn/6 ins 20 mM NaCl pH 7.4 | 25° C. Increase in the amount of the related substances on day 42 relative to day 0 (%) | 37° C. Increase in the amount of the related substances on day 21 relative to day 0 (%) | 37° C Increase . in the amount of the related substances on day 42 relative to day 0 (%) |
|---|---|---|---|
| 100 U compound 4 | 0.48 | 3.23 | 5.69 |
| 200 U compound 4 | 0.71 | 3.06 | 5.03 |

It can be seen from the above tables that the amount of HMWP and that of the related substances in the above acylated insulin formulations disclosed herein increase relatively slowly with time, suggesting that the acylated insulin formulations obtained by the present invention all have good chemical stability.

Example 34

This experiment was intended to determine the chemical stability of the acylated insulin formulations disclosed herein.

Acylated Insulin Formulations

Compound 16 (the title compound of Example 18) was dissolved in 0.08% NaOH solution to a concentration two times that of the final insulin concentration, and then the pH was adjusted to 7.45 with 4% NaOH solution. Phenol, m-cresol, glycerol and sodium chloride were mixed well according to the amount of each component specified in the table below and added to the compound 16 solution, and the pH was adjusted to 7.4. Zinc acetate was added to the compound 16 solution in three equal portions according to the amount specified in the table below, and the pH was adjusted to 7.4. Acylated insulin formulations with a final insulin concentration of 1.2 mM (9.43 mg/mL) or 1.5 mM (11.74 mg/mL) were produced.

The chemical stability of the formulations in this example can be shown by the change in the amount of high molecular weight protein (HMWP) after 14 and 21 days of storage at 25° C. and 37° C. relative to day 0, and can also be shown by the change in the amount of related substances measured after 14 and 21 days of storage at 25° C. and 37° C.

Determination of High Molecular Weight Protein (HMWP)

Amount of HMWP was determined by procedures similar to those described in Example 32. Tables 13-15 show the increase in the amount of HMWP at 25° C. and 37° C. on day 14 and day 21 relative to day 0.

TABLE 13

| 1.2 mM compound 16 10 mM m-cresol 15 mg/mL glycerol 30 mM phenol pH 7.4 | 25° C. Increase in the amount of HMWP on day 14 relative to day 0 (%) | 25° C. Increase in the amount of HMWP on day 21 relative to day 0 (%) | 37° C. Increase in the amount of HMWP on day 14 relative to day 0 (%) | 37° C. Increase in the amount of HMWP on day 21 relative to day 0 (%) |
|---|---|---|---|---|
| 2.5 Zn/6ins + 10 mM NaCl | 0.20 | 0.32 | 0.64 | 0.83 |
| 4.0 Zn/6ins + 10 mM NaCl | 0.23 | 0.31 | 0.62 | 1.05 |
| 7.0 Zn/6ins + 10 mM NaCl | 0.08 | 0.11 | 0.38 | 0.89 |
| 2.5 Zn/6ins + 50 mM NaCl | 0.24 | 0.33 | 0.83 | 1.39 |

TABLE 14

| 1.5 mM compound 16 10 mM m-cresol 15 mg/mL glycerol pH 7.4 | 25° C. Increase in the amount of HMWP on day 14 relative to day 0 (%) | 25° C. Increase in the amount of HMWP on day 21 relative to day 0 (%) | 37° C. Increase in the amount of HMWP on day 14 relative to day 0 (%) | 37° C. Increase in the amount of HMWP on day 21 relative to day 0 (%) |
|---|---|---|---|---|
| 30 mM phenol + 2.5 Zn/6 ins + 10 mM NaCl | 0.12 | 0.16 | 0.46 | 0.69 |
| 30 mM phenol + 7.0 Zn/6 ins + 10 mM NaCl | 0.05 | 0.08 | 0.27 | 0.43 |
| 30 mM phenol + 2.5 Zn/6 ins + 50 mM NaCl | 0.15 | 0.22 | 0.46 | 0.70 |
| 60 mM phenol + 7.0 Zn/6 ins + 10 mM NaCl | 0.03 | 0.06 | 0.22 | 0.39 |
| 45 mM phenol + 4.0 Zn/6 ins + 30 mM NaCl | 0.13 | 0.18 | 0.47 | 0.72 |

TABLE 14-continued

| 1.5 mM compound 16 10 mM m-cresol 15 mg/mL glycerol pH 7.4 | 25° C. Increase in the amount of HMWP on day 14 relative to day 0 (%) | 25° C. Increase in the amount of HMWP on day 21 relative to day 0 (%) | 37° C. Increase in the amount of HMWP on day 14 relative to day 0 (%) | 37° C. Increase in the amount of HMWP on day 21 relative to day 0 (%) |
|---|---|---|---|---|
| 45 mM phenol + 5.5 Zn/6 ins + 30 mM NaCl | 0.09 | 0.12 | 0.33 | 0.54 |

TABLE 15

| 1.5 mM compound 16 20 mM NaCl 15 mg/mL glycerol pH 7.4 4.5 Zn/6 ins | 25° C. Increase in the amount of HMWP on day 14 relative to day 0 (%) | 25° C. Increase in the amount of HMWP on day 21 relative to day 0 (%) | 37° C. Increase in the amount of HMWP on day 14 relative to day 0 (%) | 37° C. Increase in the amount of HMWP on day 21 relative to day 0 (%) |
|---|---|---|---|---|
| 15 mM phenol + 10 mM m-cresol | 0.07 | 0.15 | 0.42 | 0.63 |
| 35 mM phenol + 10 mM m-cresol | 0.02 | 0.07 | 0.31 | 0.63 |
| 25 mM phenol + 25 mM m-cresol | 0.10 | 0.13 | 0.44 | 0.75 |

It can be seen from the above tables that the amount of HMWP in the acylated insulin formulations disclosed herein increases very slowly with time, suggesting that the above acylated insulin formulations all have excellent chemical stability.

Determination of the Amount of Related Substances

The content of insulin related substances was determined on a Waters Kromasil 300A-5 m-C4 (4.6×150 mm) column by high performance liquid chromatography (HPLC) (column temperature: 40° C.; sample cell temperature: 10° C.; flow rate of elution phase: 1.0 mL/min). Elution was performed with a mobile phase consisting of:

phase A: 0.18 M anhydrous sodium sulfate and 10% acetonitrile (v/v), with pH adjusted to 2.3 with 85% phosphoric acid; and phase B: 75% acetonitrile (v/v).

Gradient: an isocratic gradient of 48%/52% A/B from 0 min to 40 min, a linear change to 0%/100% A/B from 40 min to 51 min, and a linear change to 48%/52% A/B from 51 min to 65 min.

Tables 16-17 show the increase in the amount of related substances at 25° C. and 37° C. on day 14 and/or day 21 relative to day 0.

TABLE 16

| 1.2 mM compound 16 10 mM m-cresol 15 mg/mL glycerol 30 mM phenol pH 7.4 | 25° C. Increase in the amount of the related substances on day 14 relative to day 0 (%) | 25° C. Increase in the amount of the related substances on day 21 relative to day 0 (%) | 37° C. Increase in the amount of the related substances on day 14 relative to day 0 (%) | 37° C. Increase in the amount of the related substances on day 21 relative to day 0 (%) |
|---|---|---|---|---|
| 2.5 Zn/6ins + 10 mM NaCl | 0.65 | 0.68 | 1.67 | 2.37 |
| 4.0 Zn/6ins + 10 mM NaCl | 0.63 | 0.67 | 2.26 | 2.42 |
| 7.0 Zn/6ins + 10 mM NaCl | 0.40 | 0.47 | 1.13 | 2.12 |
| 2.5 Zn/6ins + 50 mM NaCl | 0.67 | 0.83 | 1.67 | 2.43 |

TABLE 17

| 1.5 mM compound 16 10 mM m-cresol 15 mg/mL glycerol pH 7.4 | 25° C. Increase in the amount of the related substances on day 21 relative to day 0 (%) | 37° C. Increase in the amount of the related substances on day 14 relative to day 0 (%) | 37° C. Increase in the amount of the related substances on day 21 relative to day 0 (%) |
|---|---|---|---|
| 30 mM phenol + 2.5 Zn/6 ins + 10 mM NaCl | 0.76 | 1.08 | 1.66 |
| 30 mM phenol + 7.0 Zn/6 ins + 10 mM NaCl | 0.60 | 1.10 | 1.58 |
| 30 mM phenol + 2.5 Zn/6 ins + 50 mM NaCl | 0.97 | 1.28 | 1.72 |

TABLE 17-continued

| 1.5 mM compound 16 10 mM m-cresol 15 mg/mL glycerol pH 7.4 | 25° C. Increase in the amount of the related substances on day 21 relative to day 0 (%) | 37° C. Increase in the amount of the related substances on day 14 relative to day 0 (%) | 37° C. Increase in the amount of the related substances on day 21 relative to day 0 (%) |
|---|---|---|---|
| 60 mM phenol + 7.0 Zn/6 ins + 10 mM NaCl | 0.51 | 1.04 | 1.50 |
| 45 mM phenol + 4.0 Zn/6 ins + 30 mM NaCl | 0.77 | 1.14 | 1.53 |
| 45 mM phenol + 5.5 Zn/6 ins + 30 mM NaCl | 0.59 | 1.11 | 1.25 |

TABLE 18

| 1.5 mM compound 16 20 mM NaCl 15 mg/mL glycerol pH 7.4 4.5 Zn/6 ins | 37° C. Increase in the amount of the related substances on day 14 relative to day 0 (%) | 37° C. Increase in the amount of the related substances on day 21 relative to day 0 (%) |
|---|---|---|
| 15 mM phenol + 10 mM m-cresol | 0.60 | 0.60 |
| 35 mM phenol + 10 mM m-cresol | 0.37 | 0.52 |
| 25 mM phenol + 25 mM m-cresol | 0.55 | 0.95 |

It can be seen from the above tables that the amount of related substances of insulin in the acylated insulin formulations disclosed herein also increases very slowly with time, suggesting that the acylated insulin formulations above are very stable.

Example 35

This experiment was intended to determine the chemical stability of the acylated insulin formulations disclosed herein.

Acylated Insulin Formulations

Compound 16 (the title compound of Example 18) was dissolved in 10 mM disodium hydrogen phosphate (50% in final volume) solution to a concentration two times that of the final insulin concentration, and then the pH was adjusted to the final value with 4% NaOH. Phenol, m-cresol, glycerol and sodium chloride were mixed well according to the amount of each component specified in the table below and added to the compound 16 solution, and the pH was adjusted to the final value. Zinc acetate was added to the compound 16 solution in three equal portions according to the amount specified in the table below, and the pH was adjusted to the final value. Acylated insulin formulations with a final insulin concentration of 1.5 mM (11.74 mg/mL) were produced.

HMWP was determined by procedures similar to those described in Example 32, and change in the amount of related substances was determined by procedures similar to those described in Example 34. Tables 19 and 20 below show the change in the amount of HMWP and related substances in the acylated insulin formulations of different formulas.

TABLE 19

| 1.5 mM compound 16 10 mM m-cresol 17 mg/mL glycerol 45 mM phenol 2.2 Zn/6 ins 20 mM NaCl 5 mM disodium hydrogen phosphate | 25° C. Increase in the amount of HMWP on day 14 relative to day 0 (%) | 25° C. Increase in the amount of HMWP on day 28 relative to day 0 (%) | 37° C. Increase in the amount of HMWP on day 14 relative to day 0 (%) | 37° C. Increase in the amount of HMWP on day 28 relative to day 0 (%) |
|---|---|---|---|---|
| pH 6.5 | 0.10 | 0.19 | 0.53 | 1.11 |
| pH 7.0 | 0.14 | 0.24 | 0.47 | 0.89 |
| pH 7.5 | 0.14 | 0.27 | 0.44 | 0.96 |
| pH 8.0 | 0.14 | 0.34 | 0.61 | 1.62 |

TABLE 20

| 1.5 mM compound 16 10 mM m-cresol 17 mg/mL glycerol 45 mM phenol 2.2 Zn/6 ins 20 mM NaCl 5 mM disodium hydrogen phosphate | 25° C. Increase in the amount of the related substances on day 14 relative to day 0 (%) | 25° C. Increase in the amount of the related substances on day 21 relative to day 0 (%) | 37° C. Increase in the amount of the related substances on day 14 relative to day 0 (%) | 37° C. Increase in the amount of the related substances on day 21 relative to day 0 (%) |
|---|---|---|---|---|
| pH 6.5 | 0.71 | 0.76 | 1.45 | 1.81 |
| pH 7.0 | 0.55 | 0.71 | 1.09 | 1.36 |
| pH 7.5 | 0.63 | 0.69 | 1.11 | 1.46 |
| pH 8.0 | 0.63 | 0.58 | 1.33 | 2.14 |

It can be seen from the above tables that the amount of HMWP and that of the related substances in the above acylated insulin formulations disclosed herein increase relatively slowly with time, suggesting that the acylated insulin formulations obtained by the present invention all have good chemical stability.

Example 36

This experiment was intended to determine the chemical stability of the combo formulations of an acylated insulin and insulin aspart disclosed herein.

For the combo formulations of the acylated insulin and insulin aspart, combinations 1-5 were prepared according to the amount of each component listed in Table 21, the content of Zn being expressed as Zn/6 moles of the acylated insulin (abbreviated as "Zn/6 ins").

TABLE 21

| | Combination 5 | | | | |
|---|---|---|---|---|---|
| | Combination 1 | Combination 2 | Combination 3 | Combination 4 | Combination 5 |
| Compound 4 | 0.18 mM (or 30 U/mL) | | | | |
| Insulin aspart | 0.18 mM (or 30 U/mL) | | | | |
| Zinc acetate (μg/mL) | 22.46 | 22.46 | 26.38 | 22.46 | 24.42 |
| Zn/6ins | 11.5 | 11.5 | 13.51 | 11.5 | 12.51 |
| Phenol (mM) | 40 | 40 | 40 | 70 | 55 |
| NaCl (mM) | 45 | 75 | 45 | 45 | 60 |
| Other excipients | 10 mM m-cresol<br>8.5 mg/mL glycerol<br>pH 7.4 | | | | |

The chemical stability of the formulations in this example can be shown by the change in the amount of high molecular weight protein (HMWP) after 14 and 28 days of storage at 37° C. relative to day 0.

Determination of High Molecular Weight Protein (HMWP)

The content of high molecular weight protein (HMWP) was determined on a Tskgel G2000 SWXL (7.8×300 mm, 5 μm) column by high performance liquid chromatography (HPLC) (column temperature: 30° C.; sample cell temperature: 10° C.; mobile phase: 400 mL of isopropanol, 300 mL of glacial acetic acid and 300 mL of water; flow rate: 0.5 mL/min). The detection wavelength was 276 nm, and the sample volume was 10 μL. Table 22 shows the increase in the amount of HMWP at 37° C. on day 14 and day 28 relative to day 0.

TABLE 22

| Combo formulation | 37° C. Increase in the amount of HMWP on day 14 relative to day 0 (%) | 37° C. Increase in the amount of HMWP on day 28 relative to day 0 (%) |
|---|---|---|
| Combination 1 | 0.34 | 1.03 |
| Combination 2 | 0.32 | 0.73 |
| Combination 3 | 0.35 | 0.76 |
| Combination 4 | 0.47 | 1.32 |
| Combination 5 | 0.37 | 1.02 |

It can be seen from the above table that the amount of HMWP in the above combo formulations of acylated insulin and insulin aspart disclosed herein increases very slowly with time, suggesting that the above combo formulations all have excellent chemical stability.

Example 37

This experiment was intended to determine the chemical stability of the combo formulations of an acylated insulin and insulin aspart disclosed herein.

Combinations 6-10 were formulated according to the amount of each component specified in Table 23 below. Besides, change in the amount of HMWP was determined by procedures similar to those described in Example 36. The table 24 below shows the change in the amount of HMWP

TABLE 23

| | Combination 6 | Combination 7 | Combination 8 | Combination 9 | Combination 10 |
|---|---|---|---|---|---|
| Compound 4 | 0.165 mM (or 27.5 U/mL) | | | | |
| Insulin aspart | 0.18 mM (or 30 U/mL) | | | | |
| Zinc acetate (μg/mL) | 16.78 | 16.78 | 20.54 | 16.78 | 18.75 |
| Zn/6ins | 9.38 | 9.38 | 11.49 | 9.38 | 10.48 |
| Phenol (mM) | 20 | 20 | 20 | 35 | 27.5 |
| M-cresol (mM) | 16 | 10 | 10 | 10 | 16 |
| Other excipients | 20 mM NaCl<br>17 mg/mL glycerol<br>pH 7.4 | | | | |

TABLE 24

| Combo formulation | 37° C. Increase in the amount of HMWP on day 14 relative to day 0 (%) | 37° C. Increase in the amount of HMWP on day 28 relative to day 0 (%) |
|---|---|---|
| Combination 6 | 0.33 | 1.03 |
| Combination 7 | 0.28 | 0.79 |
| Combination 8 | 0.35 | 1.64 |
| Combination 9 | 0.40 | 1.50 |
| Combination 10 | 0.34 | 1.17 |

It can be seen from the above table that the amount of HMWP in the above combo formulations of acylated insulin and insulin aspart disclosed herein increases very slowly with time, suggesting that the above combo formulations all have excellent chemical stability.

Example 38

This experiment was intended to determine the chemical stability of the combo formulations of an acylated insulin and insulin aspart disclosed herein.

Combinations 11 and 12 were formulated according to the amount of each component specified in Table 25 below. Besides, change in the amount of HMWP was determined by procedures similar to those described in Example 36. The table 26 below shows the change in the amount of HMWP in the acylated insulin formulations of different formulas.

TABLE 25

| | Combination 11 | Combination 12 |
|---|---|---|
| Compound 4 | 0.18 mM (or 30 U/mL) | 0.165 mM (or 27.5 U/mL) |
| Insulin aspart | 0.18 mM (or 30 U/mL) | 0.18 mM (or 30 U/mL) |
| Zinc acetate (μg/mL) | 18.75 | 18.75 |
| Zn/6ins | 9.61 | 10.48 |
| Other excipients | 28 mM phenol<br>10 mM m-cresol<br>17 mg/mL glycerol<br>20 mM NaCl<br>pH 7.4 | |

TABLE 26

| Combo formulation | 37° C. Increase in the amount of HMWP on day 21 relative to day 0 (%) | 37° C. Increase in the amount of HMWP on day 28 relative to day 0 (%) |
|---|---|---|
| Combination 11 | 0.63 | 0.87 |
| Combination 12 | 0.77 | 1.18 |

It can be seen from the above table that the amount of HMWP in the above combo formulations of acylated insulin and insulin aspart disclosed herein increases very slowly with time, suggesting that the above combo formulations both have excellent chemical stability.

Example 39

Pharmacodynamic Study in db/db Mice

This study was intended to demonstrate the regulatory effect of a composition comprising an acylated insulin disclosed herein and insulin aspart on blood glucose (BG) in an obese diabetic mouse model (db/db mice) in the diabetic setting.

Reference was made to similar experiment procedures in Example 31 to obtain db/db mice for experiments. Before the start of the experiment on the day, the mice were detected for random blood glucose and weighed. Mice were each distributed to either the vehicle group or the treatment group based on random blood glucose and body weight. There was a total of 3 groups with 5 mice for each, and treatments for the groups were as follows: subcutaneous injection of vehicle; subcutaneous injection of a pharmaceutical composition comprising insulin degludec and insulin aspart, the doses of insulin degludec and insulin aspart being 9.3 U/kg and 4 U/kg, respectively; subcutaneous injection of a pharmaceutical composition comprising compound 4 (the title compound of Example 4 of the present invention) and insulin aspart, the doses of compound 4 and insulin aspart being 3.7 U/kg and 4 U/kg, respectively, upon injection of the pharmaceutical composition, wherein the vehicle contained: 55 mM phenol, 10 mM m-cresol, 8.5 mg/mL glycerol and 60 mM NaCl, with a pH value of 7.6.

The injection solution of acylated insulin and that of insulin aspart were dissolved in the vehicle to a corresponding administration concentration, and the administration volume was 5 mL/kg (i.e., 50 μL/10 g body weight). The administration was performed once daily by subcutaneous injection.

The mice had free access to food and water during the treatment, and they were evaluated for the random blood glucose at times 0.5 h, 1 h, 2 h, 3 h, 4 h, 6 h and 8 h after the administration on day 21 of the consecutive administration process and the fasting blood glucose at times 0.5 h, 1 h, 2 h, 3 h, 4 h, 6 h, 8 h and 10 h after the administration on day 18 of the consecutive administration process.

The tail of each mouse was cleaned with an alcohol cotton ball, and blood drops were collected from the tail using a disposable blood collection needle and measured with a glucometer and accompanying testing strips (Roche). The dose-response curve of blood glucose versus time was plotted for each single dose of the injection of acylated insulin and insulin aspart.

In order to illustrate the effect of the pharmaceutical composition comprising an acylated insulin and insulin aspart disclosed herein on blood glucose, the area under the blood glucose-time curve (AUC) from time 0 to the monitoring endpoint was calculated for each individual dose-response curve. The smaller the AUC value, the better the hypoglycemic effect, and the better the drug effect.

FIGS. **22*a*-22*d*** show that after administration, the pharmaceutical composition comprising the acylated insulin disclosed herein and insulin aspart has surprisingly increased hypoglycemic effect in the obese diabetic mouse model (db/db mice) relative to the pharmaceutical composition comprising insulin degludec and insulin aspart, and it can still achieve a better hypoglycemic effect and can result in a longer duration of hypoglycemic effect when the dose ratio of compound 4 to insulin aspart is far less than that of insulin degludec to insulin aspart.

Example 40. Pharmacokinetics

This example was intended to illustrate the in vivo pharmacokinetic profile of the compounds disclosed herein.

Pharmacokinetics in SD Rats

24 SD rats were divided into compound 4 (the title compound of Example 4) low dose group, compound 4 medium dose group, compound 4 high dose group and insulin degludec group (6 rats for each group, half female and half male), and the rats in the four groups were subcutaneously injected with 2 U/kg compound 4, 6 U/kg compound 4, 18 U/kg compound 4 and 14 U/kg insulin degludec, respectively. Rats in the compound 4 low, medium and high dose groups and the insulin degludec group were subjected to blood sampling for measuring plasma concentration before administration (0 m) and at times 0.5 h, 1.5 h, 4 h, 6 h, 8 h, 24 h, 48 h and 72 h after administration. The pharmacokinetic parameters $C_{max}$, $T_{max}$, $T_{1/2}$, $AUC_{0-t}$, Vd, Cl and MRT were calculated using a non-compartmental model of WinNonLin v8.0 software. The results are shown in Table 27.

TABLE 27

Pharmacokinetic parameters in SD rats after subcutaneous injection of compound 4 and insulin degludec

| Dose (U/kg) | $T_{1/2}$ (hr) | $T_{max}$ (hr) | $C_{max}$ (ng/ml) | $AUC_{0-t}$ (hr*ng/ml) | $AUC_{INF}$ (hr*ng/ml) | Vd IU/(ng/mL)/kg | Cl IU/(h*ng/ml)/kg | MRT (hr) |
|---|---|---|---|---|---|---|---|---|
| Compound 4 2 U/kg | 6.09 | 2.75 | 52.75 | 507.94 | 563.67 | 1336.24 | 152.02 | 6.36 |
| Compound 4 6 U/kg | 9.37 | 4.25 | 121.65 | 1879.09 | 2275.89 | 1589.15 | 115.39 | 8.54 |
| Compound 4 18 U/kg | 8.49 | 5.67 | 346.07 | 6054.42 | 6770.48 | 1375.99 | 113.09 | 10.88 |
| Degludec 14 U/kg | 2.76 | 2 | 1443.24 | 8896.67 | 8920.49 | 0.0063 | 0.0016 | 4.65 |

$C_{max}$ = peak concentration,
$T_{max}$ = time to peak,
$T_{1/2}$ = terminal elimination half-life,
$AU_{C0-t}$ = area under the time-plasma concentration curve from time 0 to time t,
$AUC_{INF}$ = area under the plasma concentration-time curve from time of administration to infinity,
Vd = apparent volume of distribution,
Cl = clearance,
MRT = mean residence time Pharmacokinetics in Beagle Dogs 36 dogs were divided into compound 4 low dose group (subcutaneously injected with 0.3 U/kg compound 4), compound 4 medium dose group (subcutaneously injected with 0.6 U/kg compound 4), compound 4 high dose group (subcutaneously injected with 1.2 U/kg compound 4), compound 4 intravenous injection group (intravenously injected with 0.6 U/kg compound 4), insulin degludec group (subcutaneously injected with 0.6 U/kg insulin degludec) and insulin degludec intravenous injection group (intravenously injected with 0.6 U/kg insulin degludec) (6 dogs for each group, half female and half male). Dogs in the compound 4 intravenous injection group and the insulin degludec intravenous injection group were subjected to blood sampling for measuring plasma concentration before administration and at times 2 min, 10 min, 30 min, 1 h, 2 h, 4 h, 6 h, 8 h, 12 h, 24 h, 30 h, 36 h and 48 h after administration, dogs in the compound 4 low dose, compound 4 high dose and insulin degludec subcutaneous injection groups were subjected to blood sampling for measuring plasma concentration before administration and at times 0.5 h, 1 h, 2 h, 4 h, 6 h, 8 h, 12 h, 24 h, 30 h, 36 h and 48 h after administration, and dogs in the compound 4 medium dose group were subjected to 7 days of consecutive administration, and were subjected to blood sampling for measuring plasma concentration before administration and at times 0.5 h, 1 h, 2 h, 4 h, 6 h, 8 h, 12 h, 24 h, 30 h, 36 h, 48 h and 72 h (last administration) after administration for the first administration and the last administration. The pharmacokinetic parameters $C_{max}$, $T_{max}$, $T_{1/2}$, $AUC_{0-t}$ and MRT were calculated using a non-compartmental model of WinNonLin v8.0 software.

The results are shown in Table 28.

TABLE 28

Pharmacokinetic parameters in beagle dogs after injection of compound 4 and insulin degludec

| Dose (U/kg) | $T_{1/2}$(hr) | $T_{max}$(hr) | $C_{max}$ (ng/ml) | $AUC_{0-t}$ (hr*ng/ml) | $AUC_{INF}$ (hr*ng/ml) |
|---|---|---|---|---|---|
| Compound 4 0.3 U/kg | 6.79 | 5.34 | 11.5 | 170 | 182 |
| Compound 4 0.6 U/kg | 6.2 | 5.33 | 35.9 | 598 | 617 |
| Compound 4 1.2 U/kg | 6 | 3.67 | 82.7 | 1117 | 1139 |
| Compound 4 intravenous injection 0.6 U/kg | 2.46 | — | 482 | 852 | 860 |
| Degludec 0.6 U/kg | 3.205 | 3.665 | 84.145 | 645.07 | 649.575 |
| Degludec intravenous injection 0.6 U/kg | 3.02 | — | 357.99 | 779.17 | 801.92 |

It can be seen from the above experimental results that the acylated insulin derivative compound 4 disclosed herein exhibits a longer half-life and more stable hypoglycemic effect in rats and beagle dogs.

Example 41

B29K(N(ε)-docosanedioyl-γGlu-12×OEG), desB30 Human Insulin (Compound 17)

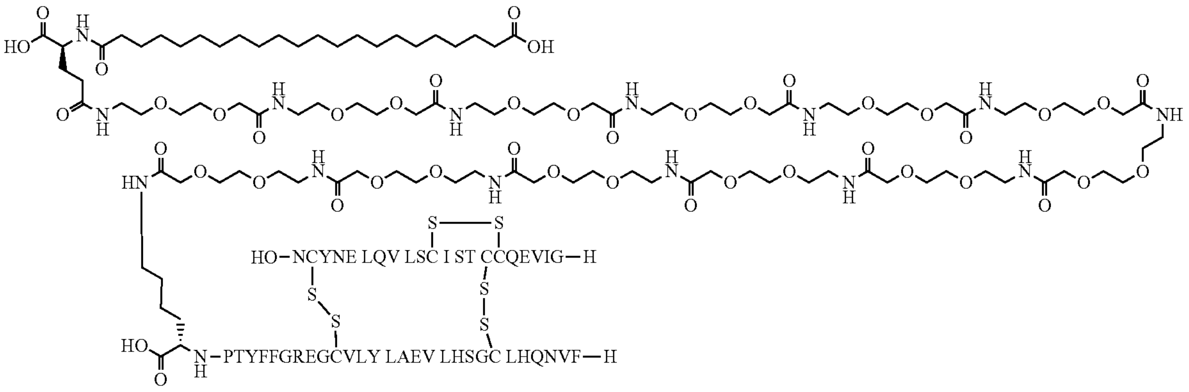

Compound B29K(N(ε)-docosanedioyl-γGlu-12×OEG), desB30 human insulin was prepared by procedures similar to those described in section 2 of Example 1.

LC-MS (ESI): m/z=1585.98[M+5H]$^{5+}$

The intermediate tert-butyl docosanedioyl-γGlu-(12× OEG-OSu)-OtBu was prepared by procedures similar to those described in section 3 of Example 1.

LC-MS (Sciex100API): m/z=2451.38 (M+1)$^{+}$

Example 42

A14E, B16H, B25H, B29K(N(ε)-docosanedioyl-γGlu-18×OEG), desB30 Human Insulin (Compound 18)

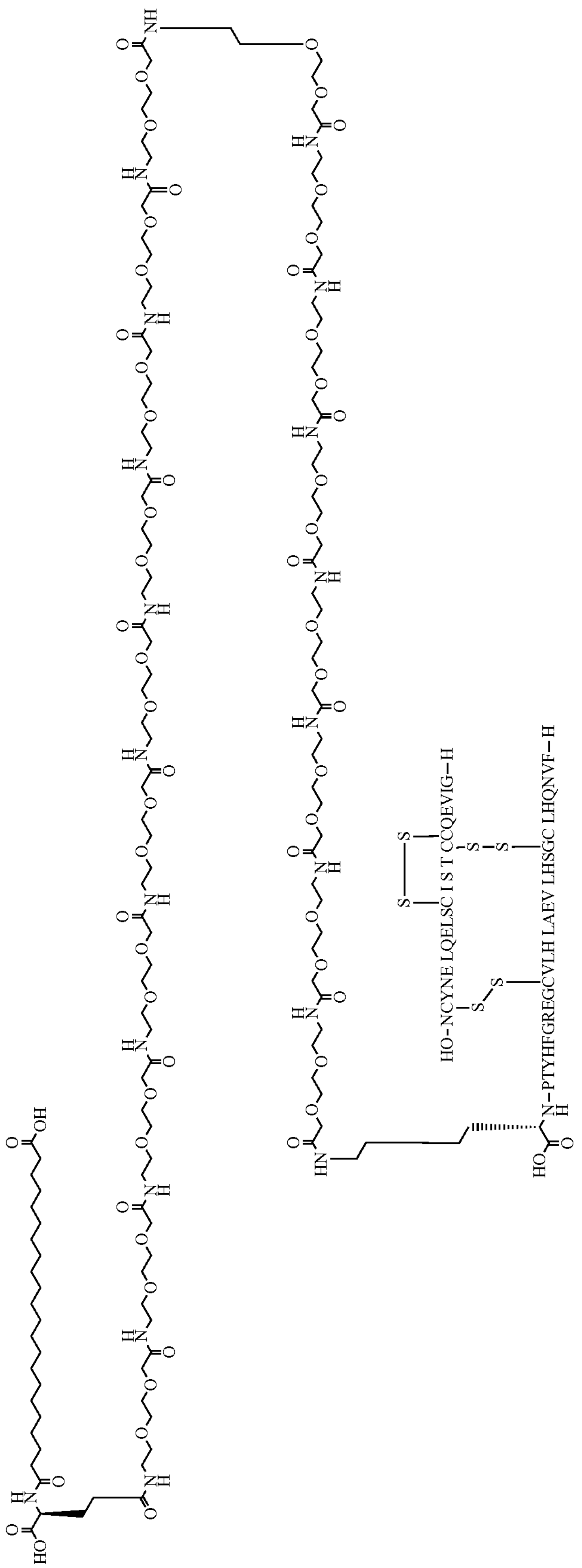

Compound A14E, B16H, B25H, B29K(N(ε)-docosanedioyl-γGlu-18×OEG), desB30 human insulin was prepared by procedures similar to those described in section 1 of Comparative Example 5.

LC-MS (ESI): m/z=1247.47$[M+7H]^{7+}$

The intermediate tert-butyl docosanedioyl-γGlu-(18×OEG-OSu)-OtBu was prepared by procedures similar to those described in section 2 of Comparative Example 5.

LC-MS (Sciex100API): m/z=3320.83 $(M+1)^+$

Example 43

A14E, B16H, B25H, B29K(N(ε)-docosanedioyl-γGlu-24×OEG), desB30 Human Insulin (Compound 19)

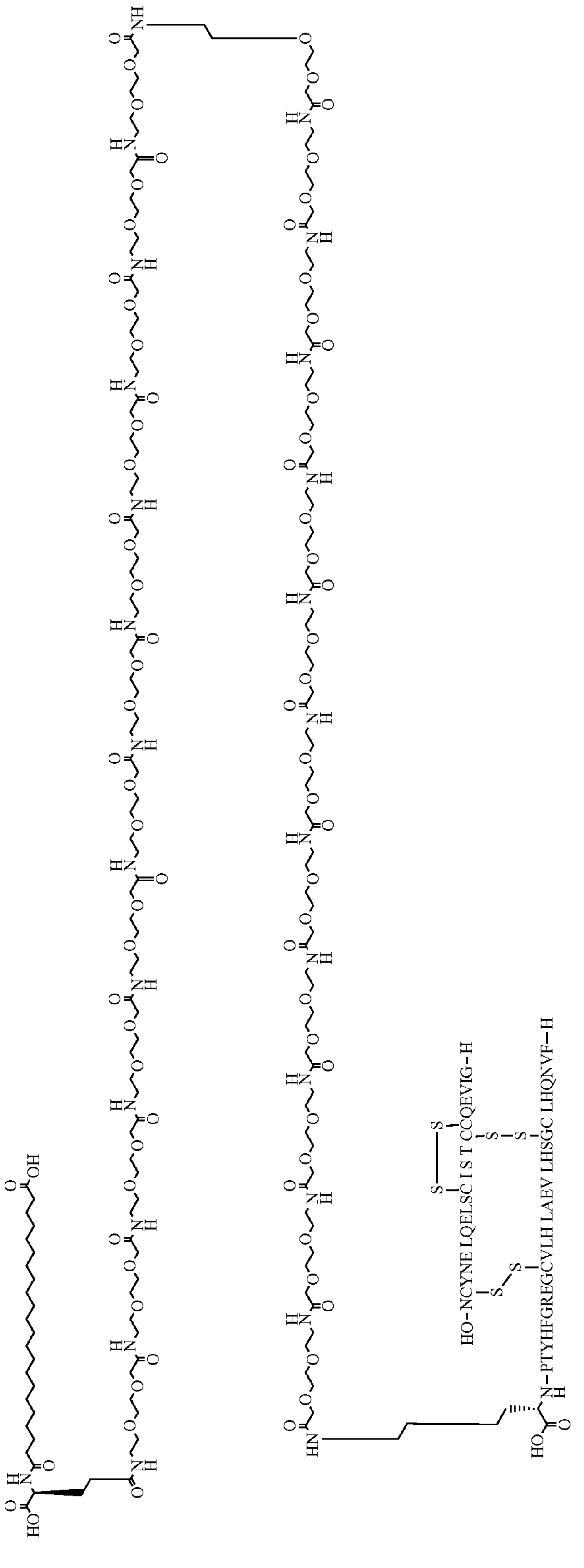

Compound A14E, B16H, B25H, B29K(N(ε)-docosanedioyl-γGlu-24×OEG), desB30 human insulin was prepared by procedures similar to those described in section 1 of Comparative Example 5.

LC-MS (ESI): m/z=873.35[M+11H]$^{11+}$

The intermediate tert-butyl docosanedioyl-γGlu-(24×OEG-OSu)-OtBu was prepared by procedures similar to those described in section 2 of Comparative Example 5.

LC-MS (Sciex100API): m/z=4192.27 (M+1)$^+$

Example 44

B29K(N(ε)-docosanedioyl-γGlu-OEG), desB30 Human Insulin (Compound 20)

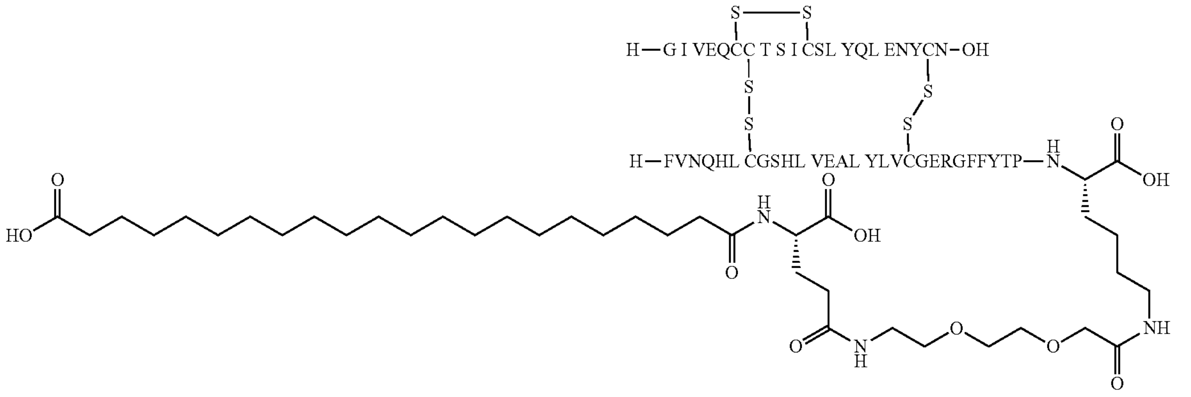

Compound B29K(N(ε)-docosanedioyl-γGlu-OEG), desB30 human insulin was prepared by procedures similar to those described in section 2 of Example 1.

LC-MS (ESI): m/z=1266.8122[M+5H]$^{5+}$

The intermediate tert-butyl docosanedioyl-γGlu-(OEG-OSu)-OtBu was prepared by procedures similar to those described in section 3 of Example 1.

LC-MS (Sciex100API): m/z=854.57 (M+1)$^+$

Example 45

B29K(N(ε)-docosanedioyl-γGlu-12×PEG), desB30 Human Insulin (Compound 21)

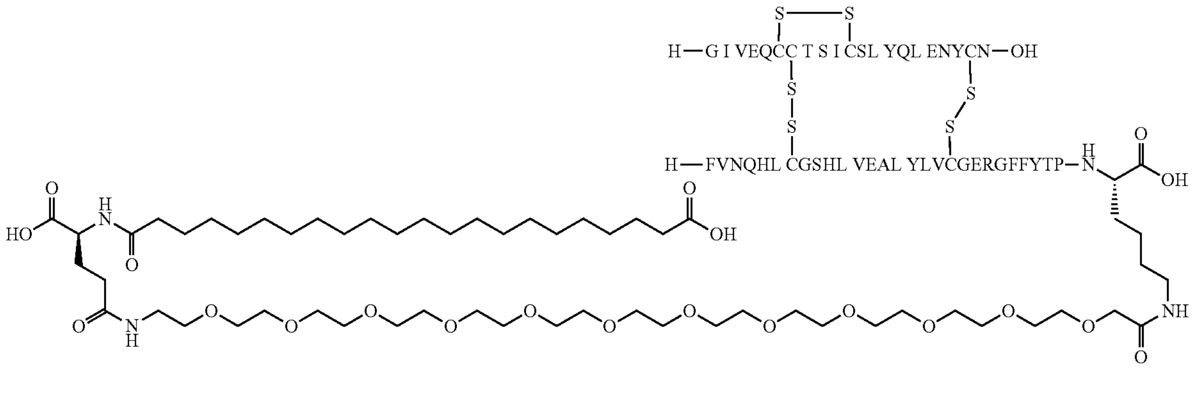

Compound B29K(N(ε)-docosanedioyl-γGlu-12×PEG), desB30 human insulin was prepared by procedures similar to those described in section 2 of Example 1.

LC-MS (ESI): m/z=1354.8667[M+5H]$^{5+}$

The intermediate tert-butyl docosanedioyl-γGlu-(12×PEG-OSu)-OtBu was prepared by procedures similar to those described in section 3 of Example 1.

LC-MS (Sciex100API): m/z=1294.83 (M+1)$^+$

Example 46

Receptor Binding Capability of Insulin Derivatives Disclosed Herein

This test was intended to demonstrate the binding capability of the insulin derivatives disclosed herein to the insulin receptor.

Compound 2 disclosed herein and control compound 2 were tested, by surface plasmon resonance (SPR) method, for binding capability to his-tagged insulin receptor A extracellular domain (IRA, Sino Biological) in the absence of human serum albumin (HSA) and in the presence of 2% HSA. Samples were diluted with running buffer (Cytiva) or with running buffer containing 2.0% HSA, such that the sample concentration of compound 2 and that of control compound 2 were both 400 nM for the two conditions. An NTA sensing chip (Cytiva) was selected to carry out SPR analysis on Biacore T200 (Cytiva) at 25° C. 0.5 M $NiCl_2$ (Cytiva) was injected at a flow rate of 10 μL/min for 60 s, which was followed by washing with HBS-EP buffer (Cytiva). 3 μg/mL IRA receptor was injected at a flow rate of 5 μL/min for 180 s to enable the IRA receptor to be bound on the surface of the chip. The test insulin derivative sample was then injected at a flow rate of 30 μL/min for 60 s, and then dissociation was performed for 60 s. After each sample injection, 350 mM EDTA (Cytiva) was injected at a flow rate of 10 μL/min for 60s for chip regeneration, and finally, the next sample detection can be carried out after washing with HBS-P buffer (Cytiva). The response value at 4 s before the start of dissociation of the sample was selected as the test result of the binding capability to the receptor, and the test was repeated 3 times for each sample.

Figure 23:
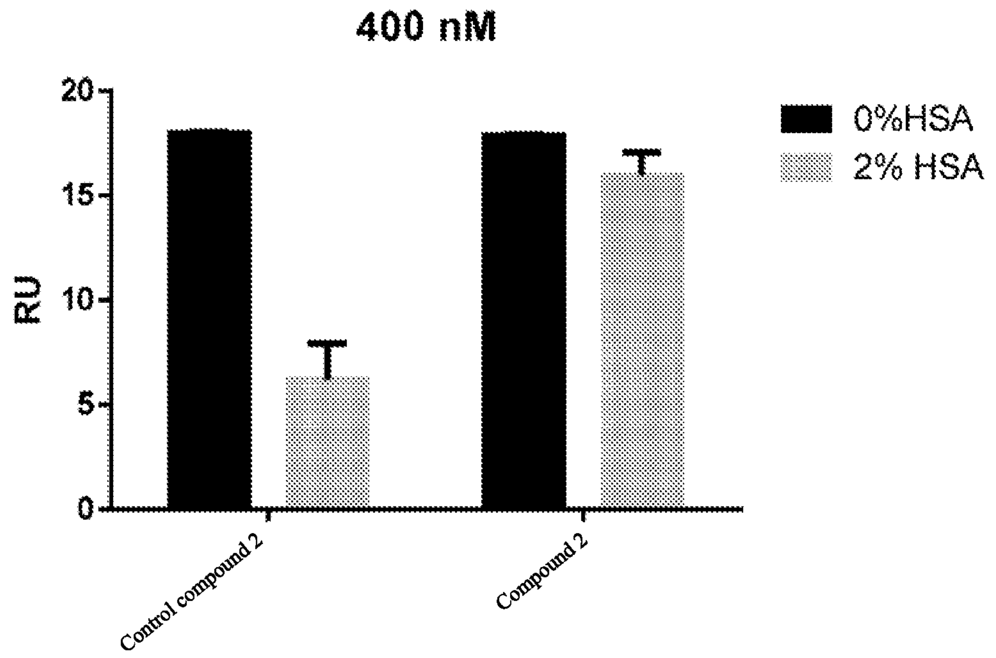
FIG. 23 shows the receptor binding capability of compound of Example 2 in the present invention and control compound 2 in the presence of 2% HSA and 0% HSA.

FIG. 23 shows the receptor binding capability of compound 2 and control compound 2 in the presence of 2% HSA (simulating physiological conditions) relative to 0% HSA. It can be seen from FIG. 23 that compound 2 has significantly improved receptor binding capability relative to control compound 2 in the presence of 2% HSA, and the effect of albumin on the receptor binding capability of compound 2 disclosed herein is significantly lower than on that of control compound 2.

This indicates that in the presence of albumin, the insulin derivatives disclosed herein, e.g., compound 2, have surprisingly and significantly improved receptor binding capability relative to control compound 2; that is, the effect of albumin on the receptor binding capability of the insulin derivatives disclosed herein is significantly lower than on that of control compound 2.

Example 47

Receptor Binding Capability of Insulin Derivatives Disclosed Herein

This test was intended to demonstrate the binding capability of the insulin derivatives disclosed herein to the insulin receptor.

The insulin derivative compound 15 disclosed herein and the control compound 5 were tested for binding capability to IRA in the absence of human serum albumin (HSA) and in the presence of 2% HSA in a manner similar to that described in Example 46, except that the sample concentration of compound 15 and that of control compound 5 were both 12800 nM and 25600 nM for the two conditions. The test results are shown in FIGS. 24*a* and 24*b*.

Figure 24A:
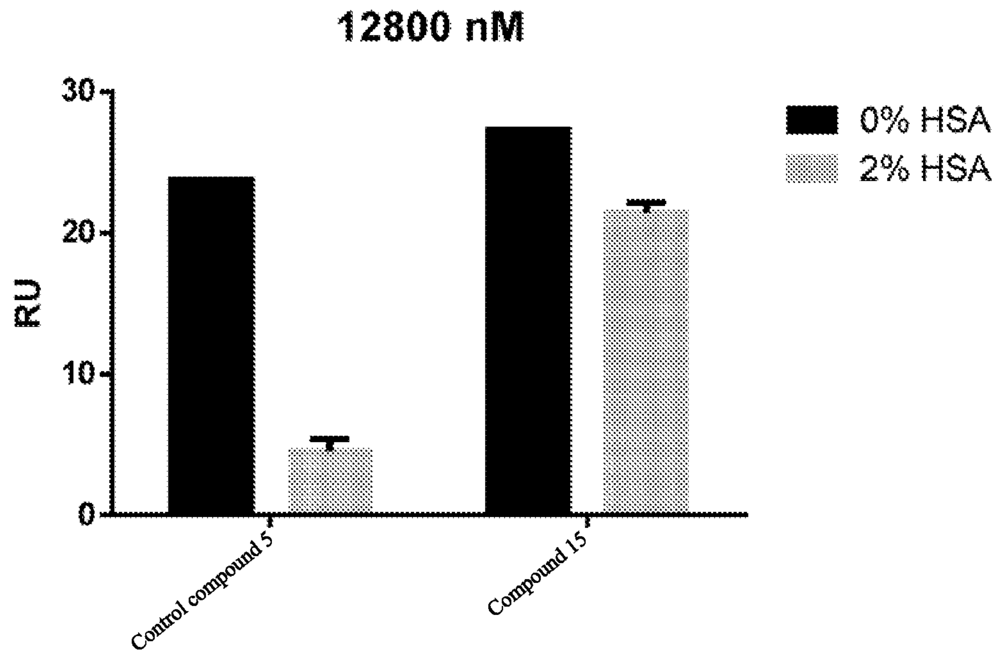
FIG. 24*a* shows the receptor binding capability of compound of Example 17 and control compound 5 in the present invention at a sample concentration of 12800 nM in the presence of 2% HSA and 0% HSA.
Figure 24B:
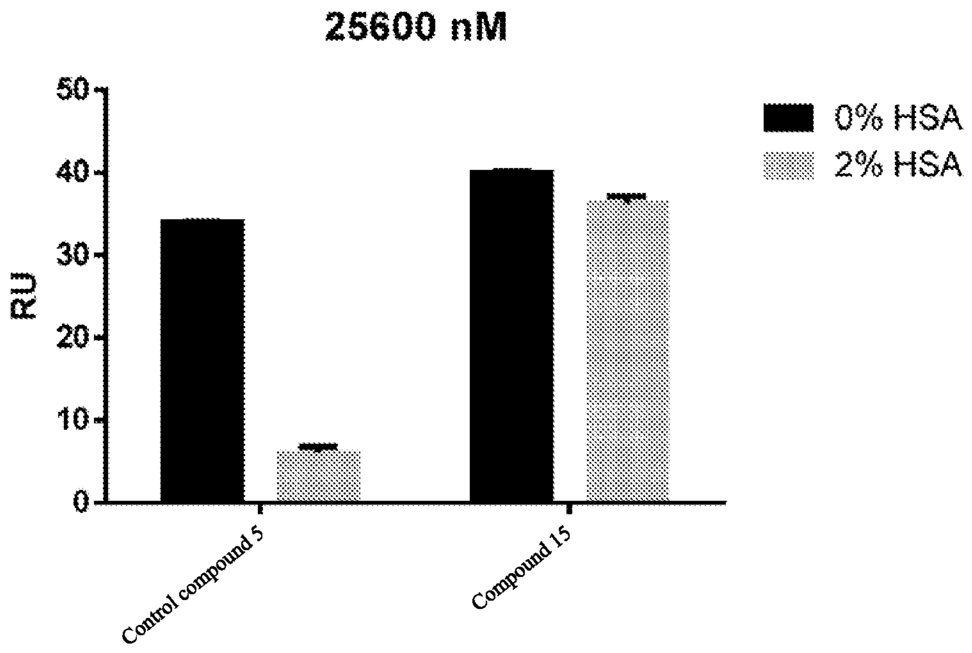
FIG. 24*b* shows the receptor binding capability of compound of Example 17 in the present invention and control compound 5 at a sample concentration of 25600 nM in the presence of 2% HSA and 0% HSA.

FIGS. 24*a* and 24*b* show the receptor binding capability of compound 15 and control compound 5 in the presence of 2% HSA (simulating physiological conditions) relative to 0% HSA. It can be seen from FIGS. 24*a* and 24*b* that compound 15 has surprisingly and significantly improved receptor binding capability relative to control compound 5 in the presence of 2% HSA, and the effect of albumin on the receptor binding capability of the insulin derivative compound 15 disclosed herein is significantly lower than on that of control compound 5.

Example 48

Receptor Binding Capability of Insulin Derivatives Disclosed Herein

This test was intended to demonstrate the binding capability of the insulin derivatives disclosed herein to the insulin receptor.

The insulin derivative compound 17 disclosed herein and the control compound 2 were tested for binding capability to IRA in the absence of human serum albumin (HSA) and in the presence of 2% HSA in a manner similar to that described in Example 46. The test results are shown in FIG. 25.

Figure 25:
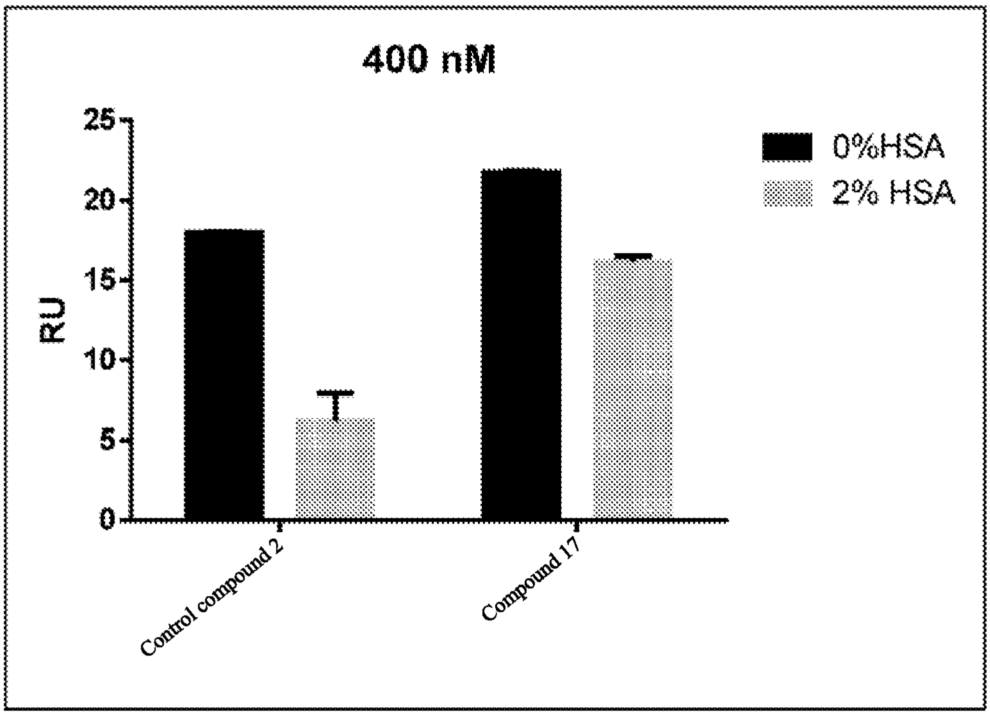
FIG. 25 shows the receptor binding capability of compound of Example 41 in the present invention and control compound 2 in the presence of 2% HSA and 0% HSA.

FIG. 25 shows the receptor binding capability of compound 17 and control compound 2 in the presence of 2% HSA (simulating physiological conditions) relative to 0% HSA. It can be seen from FIG. 25 that compound 17 has significantly improved receptor binding capability relative to control compound 2 in the presence of 2% HSA, and the effect of albumin on the receptor binding capability of the insulin derivative compound 17 disclosed herein is significantly lower than on that of control compound 2.

This indicates that the insulin derivatives disclosed herein, e.g., compound 17, have surprisingly and significantly improved receptor binding capability relative to control compound 2 in the presence of albumin; that is, the effect of albumin on the receptor binding capability of the insulin derivatives disclosed herein is significantly lower than on that of control compound 2.

Example 49

Receptor Binding Capability of Insulin Derivatives Disclosed Herein

This test was intended to demonstrate the binding capability of the insulin derivatives disclosed herein to the insulin receptor.

The insulin derivatives compound 16 and compound 18 disclosed herein and the control compound 5 were tested for binding capability to IRA in the absence of human serum albumin (HSA) and in the presence of 2% HSA in a manner similar to that described in Example 46, except that the sample concentration of compound 16, that of compound 18 and that of control compound 5 were all 12800 nM and 25600 nM for the two conditions. The test results are shown in FIGS. 26*a* and 26*b*.

Figure 26A:
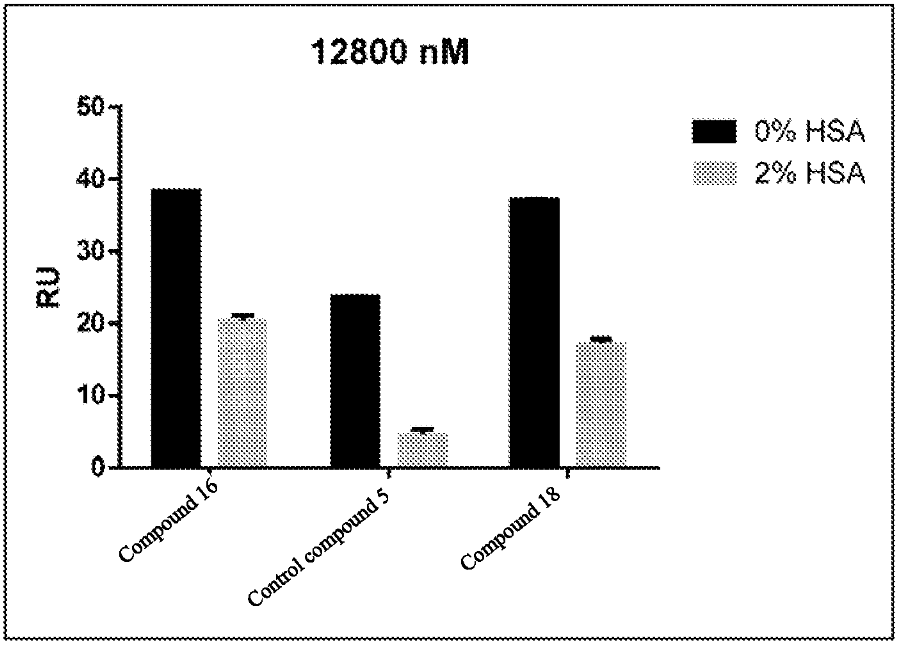
FIG. 26*a* shows the receptor binding capability of compound of Example 18, compound of Example 42 in the present invention and control compound 5 at a sample concentration of 12800 nM in the presence of 2% HSA and 0% HSA.
Figure 26B:
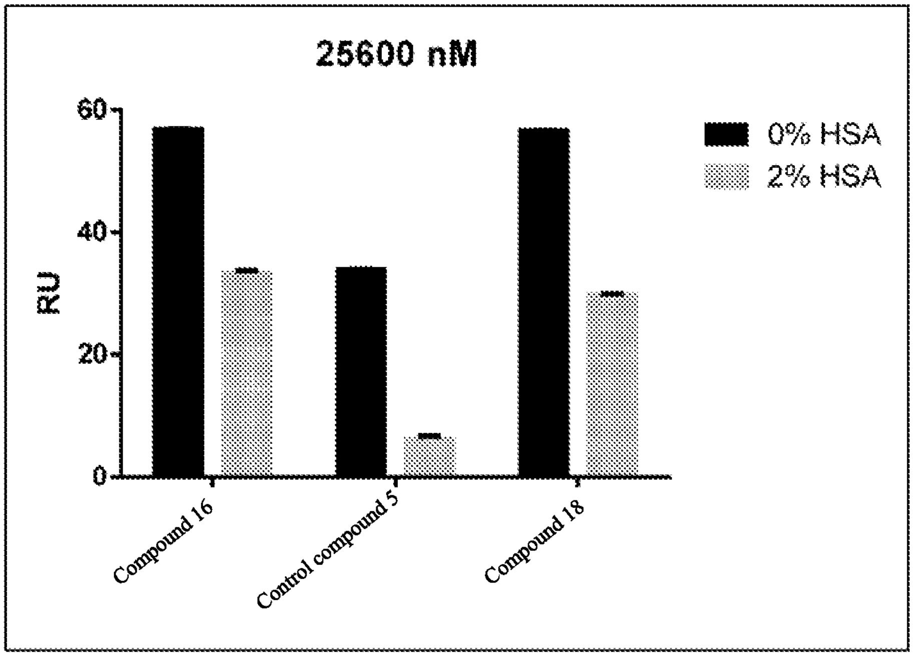
FIG. 26*b* shows the receptor binding capability of compound of Example 18 and compound of Example 42 in the present invention and control compound 5 at a sample concentration of 25600 nM in the presence of 2% HSA and 0% HSA.

FIGS. 26*a* and 26*b* show the receptor binding capability of compound 16, compound 18 and control compound 5 in the presence of 2% HSA (simulating physiological conditions) relative to 0% HSA.

It can be seen from FIGS. 26*a* and 26*b* that compound 16 and compound 18 have surprisingly and significantly improved receptor binding capability relative to control compound 5 in the presence of 2% HSA, and the effect of albumin on the receptor binding capability of the insulin derivatives disclosed herein is significantly lower than on that of control compound 5.

The present invention has been illustrated by the above examples, but it should be understood that the above examples are for illustrative and descriptive purposes only and are not intended to limit the present invention to the scope of the described examples. Furthermore, it will be understood by those skilled in the art that the present invention is not limited to the examples described above, and that many variations and modifications can be made in accordance with the teachings of the present invention, all of which fall within the scope of the present invention as claimed. The protection scope of the present invention is defined by the appended claims and equivalents thereof.

SEQUENCE LISTING

SEQ ID NO 1:
A chain of desB30 human insulin:
Gly Ile Val Glu Gln Cys Cys Thr Ser Ile Cys Ser Leu Tyr Gln Leu Glu Asn Tyr Cys Asn SEQ ID NO 2:
B chain of desB30 human insulin:
Phe Val Asn Gln His Leu Cys Gly Ser His Leu Val Glu Ala Leu Tyr Leu Val Cys Gly Glu Arg Gly Phe Phe Tyr Thr Pro Lys SEQ ID NO 3:
A chain of A14E, B16H, B25H, desB30 human insulin:
Gly Ile Val Glu Gln Cys Cys Thr Ser Ile Cys Ser Leu Glu Gln Leu Glu Asn Tyr Cys Asn SEQ ID NO 4:
B chain of A14E, B16H, B25H, desB30 human insulin:
Phe Val Asn Gln His Leu Cys Gly Ser His Leu Val Glu Ala Leu His Leu Val Cys Gly Glu Arg Gly Phe His Tyr Thr Pro Lys SEQ ID NO 5:
A chain of A14E, B16E, B25H, desB30 human insulin:
Gly Ile Val Glu Gln Cys Cys Thr Ser Ile Cys Ser Leu Glu Gln Leu Glu Asn Tyr Cys Asn SEQ ID NO 6:
B chain of A14E, B16E, B25H, desB30 human insulin:
Phe Val Asn Gln His Leu Cys Gly Ser His Leu Val Glu Ala Leu Glu Leu Val Cys Gly Glu Arg Gly Phe His Tyr Thr Pro Lys SEQ ID NO 7:
A chain of human insulin:
Gly Ile Val Glu Gln Cys Cys Thr Ser Ile Cys Ser Leu Tyr Gln Leu Glu Asn Tyr Cys Asn SEQ ID NO 8:
B chain of human insulin:
Phe Val Asn Gln His Leu Cys Gly Ser His Leu Val Glu Ala Leu Tyr Leu Val Cys Gly Glu Arg Gly Phe Phe Tyr Thr Pro Lys Thr SEQ ID NO 9:
A chain of A21G human insulin:
Gly Ile Val Glu Gln Cys Cys Thr Ser Ile Cys Ser Leu Tyr Gln Leu Glu Asn Tyr Cys Gly SEQ ID NO 10:
B chain of A21G human insulin:
Phe Val Asn Gln His Leu Cys Gly Ser His Leu Val Glu Ala Leu Tyr Leu Val Cys Gly Glu Arg Gly Phe Phe Tyr Thr Pro Lys Thr SEQ ID NO 11:
A chain of A21G, desB30 human insulin:
Gly Ile Val Glu Gln Cys Cys Thr Ser Ile Cys Ser Leu Tyr Gln Leu Glu Asn Tyr Cys Gly SEQ ID NO 12:
B chain of A21G, desB30 human insulin:
Phe Val Asn Gln His Leu Cys Gly Ser His Leu Val Glu Ala Leu Tyr Leu Val Cys Gly Glu Arg Gly Phe Phe Tyr Thr Pro Lys SEQ ID NO 13:
A chain of B28D human insulin:
Gly Ile Val Glu Gln Cys Cys Thr Ser Ile Cys Ser Leu Tyr Gln Leu Glu Asn Tyr Cys Asn SEQ ID NO 14:
B chain of B28D human insulin:
Phe Val Asn Gln His Leu Cys Gly Ser His Leu Val Glu Ala Leu Tyr Leu Val Cys Gly Glu Arg Gly Phe Phe Tyr Thr Asp Lys Thr SEQ ID NO 15:
GLP-1-(7-37) peptide
His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly SEQ ID NO 16:
[Gly8, Arg34]GLP-1-(7-37) peptide -continued His Gly Glu Gly Thr Phe Thr Ser Asp Val Ser Ser Tyr Leu Glu Gly Gln Ala Ala Lys Glu Phe Ile Ala Trp Leu Val Arg Gly Arg Gly SEQ ID NO 17:
[Arg34]GLP-1-(7-37) peptide
His Ala Glu Gly Thr Phe Thr Ser Asp Val Ser Ser Tyr Leu Glu Gly Gln Ala Ala Lys Glu Phe Ile Ala Trp Leu Val Arg Gly Arg Gly

---

The invention claimed is:

1. An insulin derivative, wherein the insulin derivative is A14E, B16H, B25H, B29K(N(ε)-eicosanedioyl-γGlu-6×OEG), desB30 human insulin; or A14E, B16H, B25H, B29K(N(ε)-docosanedioyl-γGlu-6×OEG), desB30 human insulin.

2. An insulin derivative, having the following structure:

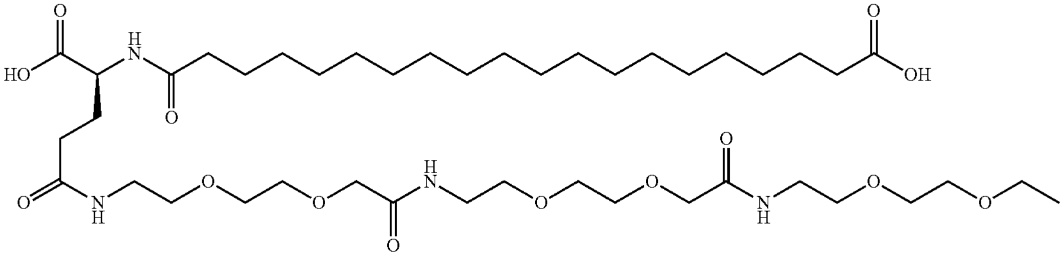

-continued

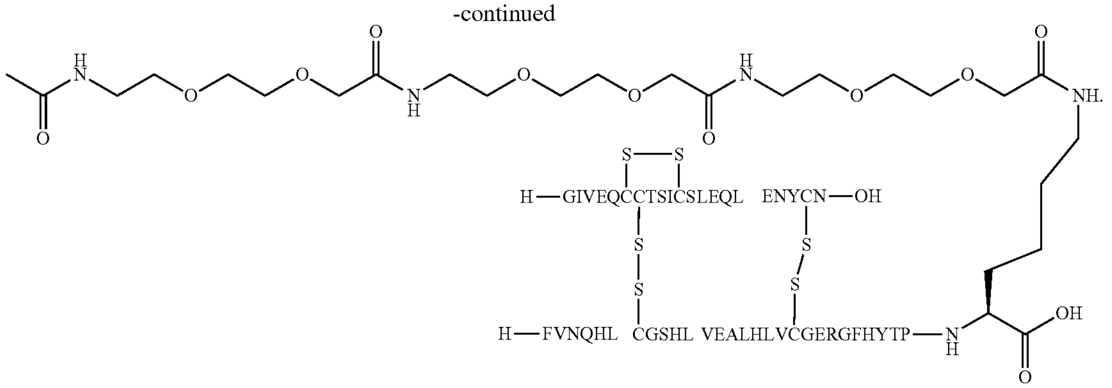

3. A pharmaceutical composition, comprising the insulin derivative according to claim 2, and one or more pharmaceutically acceptable excipients.

4. A method for treating diabetes, hyperglycemia, and/or impaired glucose tolerance, comprising administering to a subject in need thereof a therapeutically effective amount of the insulin derivative according to claim 2.

5. A pharmaceutical composition, comprising the insulin derivative according to claim 1, and one or more pharmaceutically acceptable excipients.

6. A method for treating diabetes, hyperglycemia, and/or impaired glucose tolerance, comprising administering to a subject in need thereof a therapeutically effective amount of the insulin derivative according to claim 1.

7. An insulin derivative, having the following structure:

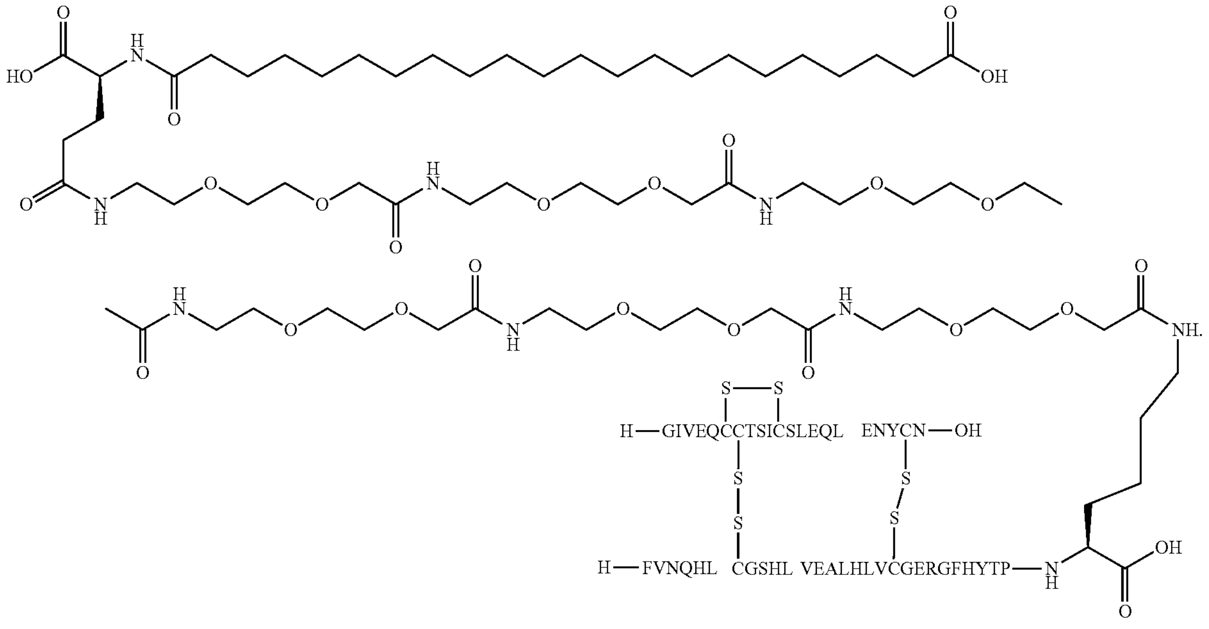

8. A pharmaceutical composition, comprising the insulin derivative according to claim 7, and one or more pharmaceutically acceptable excipients.

9. A method for treating diabetes, hyperglycemia, and/or impaired glucose tolerance, comprising administering to a subject in need thereof a therapeutically effective amount of the insulin derivative according to claim 7.

* * * * *